(12) United States Patent
Williams et al.

(10) Patent No.: US 6,806,267 B1
(45) Date of Patent: Oct. 19, 2004

(54) APOPTOSIS-INDUCING COMPOUNDS

(75) Inventors: David Clive Williams, Dublin (IE); Daniela M. Zisterer, Dublin (IE); Vito Nacci, Siena (IT); Giuseppe Campiani, Siena (IT)

(73) Assignees: The Universita'di Siena (IT); The Provost, Fellows and Scholars of the College of the Holy and Undivided Trinity of Queen Elizabeth Near Dublin (IE)

( * ) Notice: Subject to any disclaimer, the term of this patent is extended or adjusted under 35 U.S.C. 154(b) by 0 days.

(21) Appl. No.: 09/506,362

(22) Filed: Feb. 16, 2000

Related U.S. Application Data

(63) Continuation-in-part of application No. PCT/IE99/00030, filed on May 6, 1999.

(30) Foreign Application Priority Data

May 6, 1998 (IE) .................................................. 980344

(51) Int. Cl.$^7$ .................... A01K 31/553; A01K 31/554; C07D 513/04; C07D 513/14
(52) U.S. Cl. .................. 514/211.12; 540/488; 540/546; 540/547; 540/548; 514/211.1; 514/211.09
(58) Field of Search .................. 514/211.12, 211.1, 514/211.09; 540/488, 546, 547, 548

(56) References Cited

U.S. PATENT DOCUMENTS 4,898,861 A    2/1990   Morgan et al. ............. 514/221

OTHER PUBLICATIONS

McKie, "The Observer", Jun. 10, 2001.*
Daretta et al, Annual Reports in Medicinal Chemistry, vol. 31, pp 241–248 (1996).*
C. Crocker et al., *Anticancer Research*, 16:1259–1264 (1996).
T. Hirsch et al., *Experimental Cell Research*, 241:426–434 (1998).
D. Zisterer et al., *Biochemical Pharmacology*, 55:397–403 (1998).
I. Fiorini et al., *J. Med. Chem.*, 37:1427–1438 (1994).
G. Campiani et al., *J. Med. Chem.*, 39:2922–2938 (1996).
G. Campiani et al., *J. Med. Chem.*, 39:3435–3450 (1996).
A. Gorman et al., *Journal of Neurochemistry*, 53(3):849–855 (1989).
M. Pawlikowski et al., *Acta. Neurol. Scand.*, 77:231–233 (1988).
J. Kunert–Radek et al., *Neuroendocrinology*, 59:92–96 (1994).
T. Shaw, "Peripheral Benzodiazepine Receptor as a Target for Cancer Treatment", Proceedings of the 88$^{th}$ Annual Meeting of the American Association for Cancer Research, San Diego, Apr. 12–16, 1997, vol. 38, p. 602.
PCT International Search Report dated Mar. 11, 1999.
G. Campiani et al., *Eur. J. Med. Chem.*, 32:241–251 (1997).

* cited by examiner

*Primary Examiner*—John M Ford
(74) *Attorney, Agent, or Firm*—Peter F. Corless; Christine C. O'Day; Edwards & Angell, LLP

(57) ABSTRACT

The present invention relates to pyrrolobenzoxazepines, pyrrolobenzthiazepines and related compounds having the ability to induce apoptosis, to pharmaceutical compositions comprising these compounds and to their use as anti-tumour agents.

10 Claims, 37 Drawing Sheets

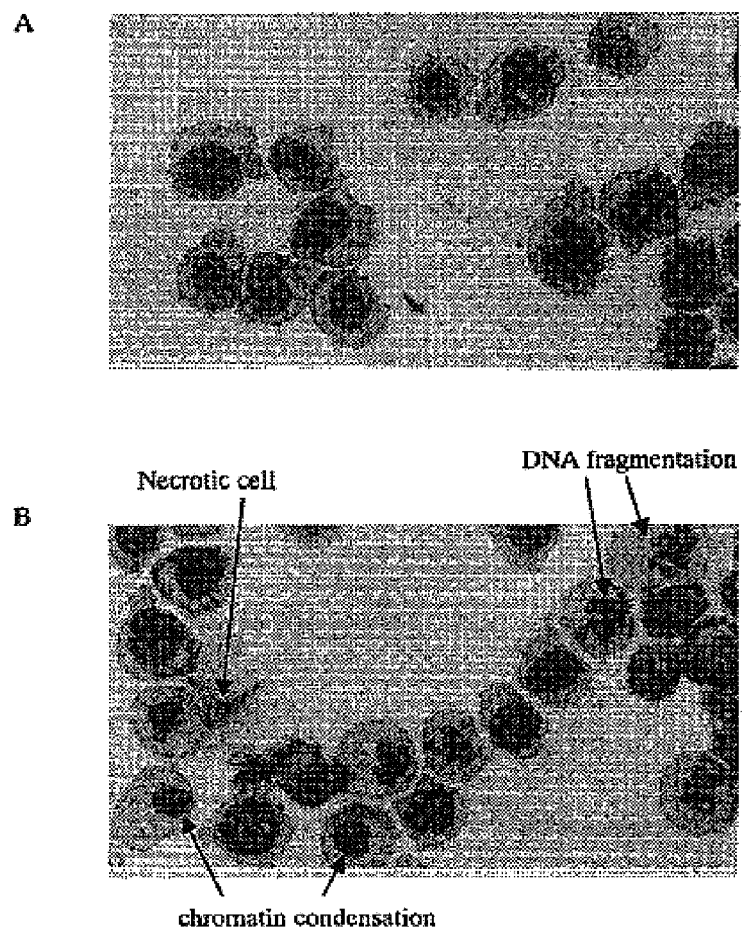

Fig. 1 Morphological features of HL-60 cells undergoing apoptosis following treatment with PBOX-6.

Microscopic analysis of HL-60 cells was performed on cytospin samples. Vehicle (1% ethanol) treated cells (A) are characterised by a continuous plasma membrane and an intact nucleus. PBOX-6 treated cells (B) display the morphological features of apoptosis, which includes chromatin condensation and DNA fragmentation.

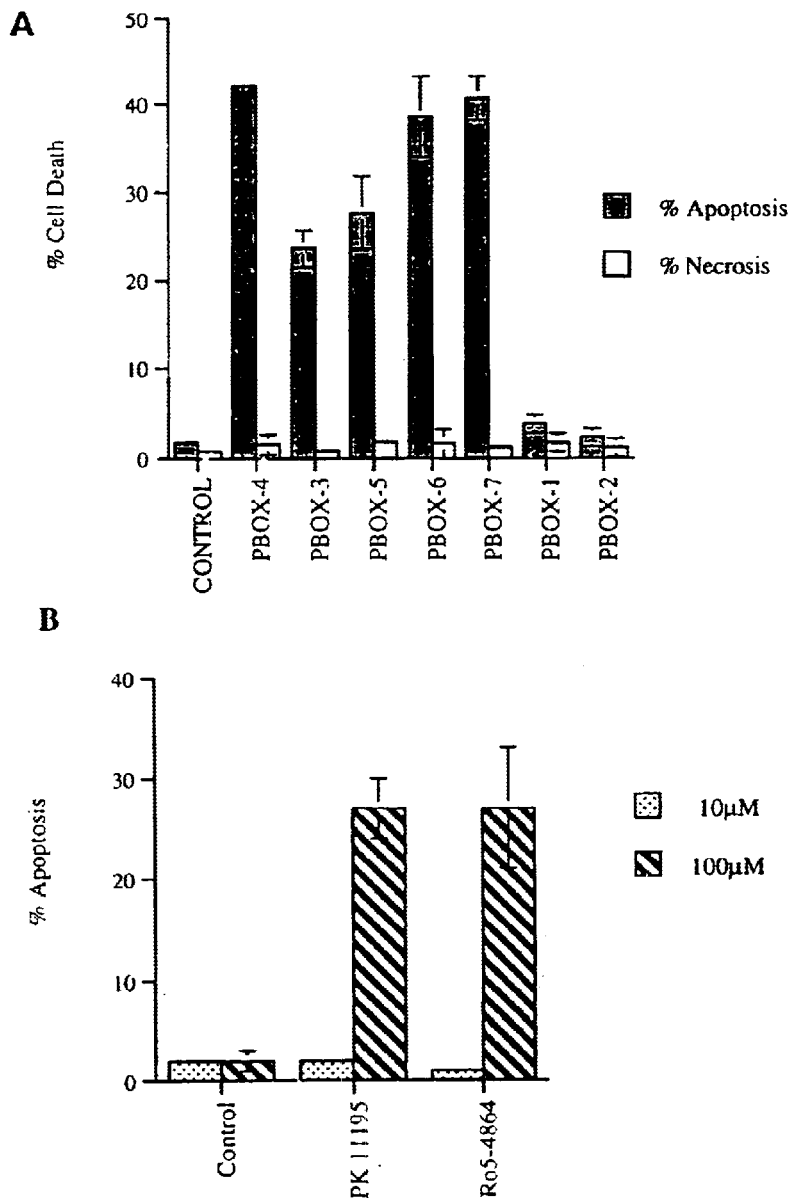

Fig. 2. Some pyrrolo-1,5-benzoxazepines and other PBR ligands induce apoptosis in HL 60 cells.
HL 60 cells were seeded at a density of $3 \times 10^5$ cells/ml and were incubated with either (A), one of the indicated PBOX drugs, each at a final concentration of 10μM or (B), PK 11195 or Ro5-4864 at a concentration of either 10μM or 100μM. The control wells in each case contained 1% (v/v). After 16h the percent apoptosis and necrosis was determined by cytospinning and staining the cells using the RapiDiff kit as described in the Methods section. Values represent the means ± SEM for three separate experiments.

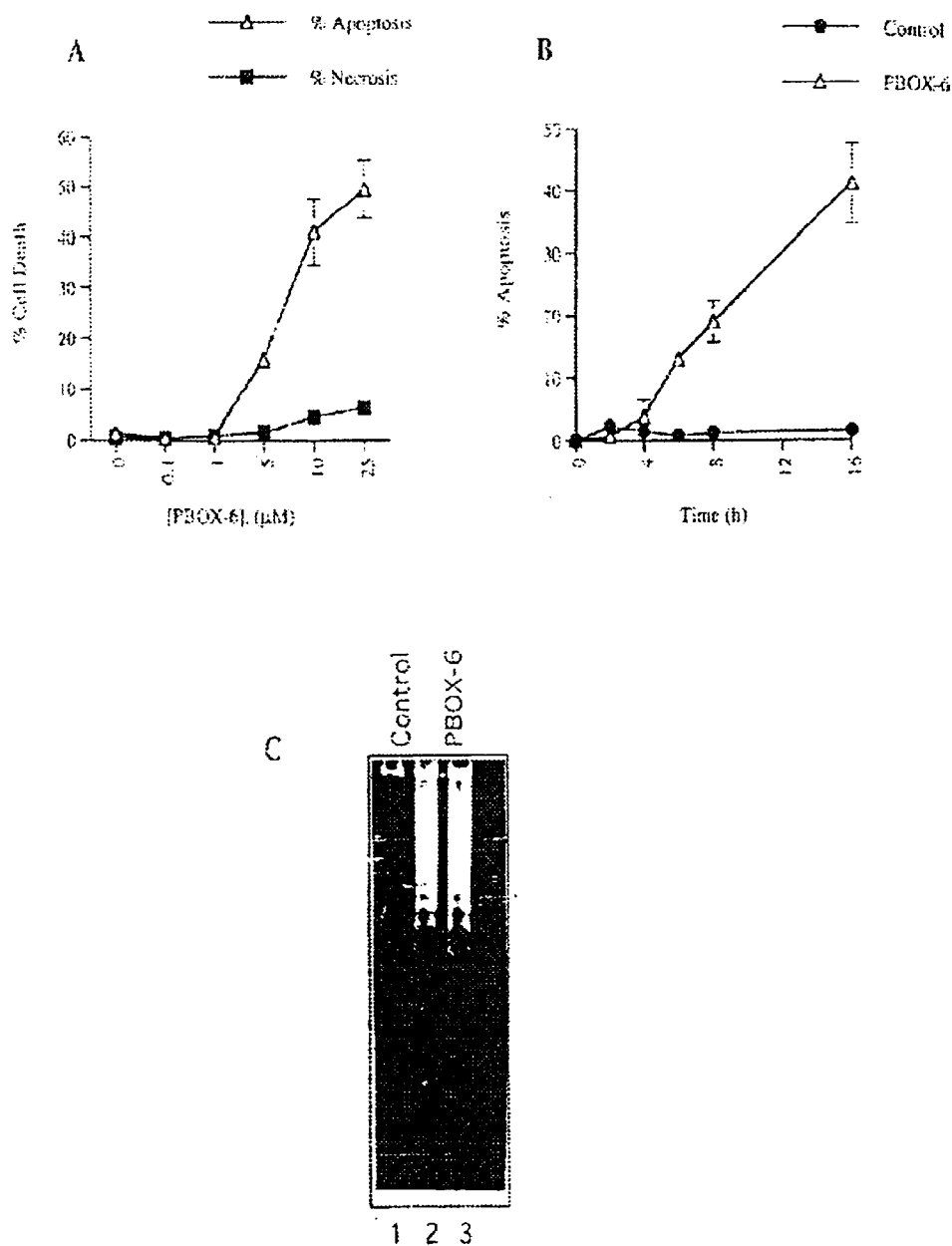

Fig. 3. PBOX-6-induced apoptosis in HL-60 cells is dose- and time-dependent and results in DNA fragmentation.

HL-60 cells were seeded at a density of 3 x $10^5$ cells/ml and were treated with either (A) a range (0-50μM) of concentrations of PBOX-6 for 16 hours or (B) one concentration of PBOX-6 (10μM) for a period of 2, 4, 6, 8 and 16 hours. The percent apoptosis and necrosis was determined by cytospinning and staining the cells using the RapiDiff kit as described in the Methods section. Values represent the mean +/- SEM for three separate experiments. (C) DNA isolated from HL-60 cells, treated for 24 hours either with control (0.5% (v/v) ethanol) or PBOX-6 (10μM) in duplicate, was analysed by gel electrophoresis.

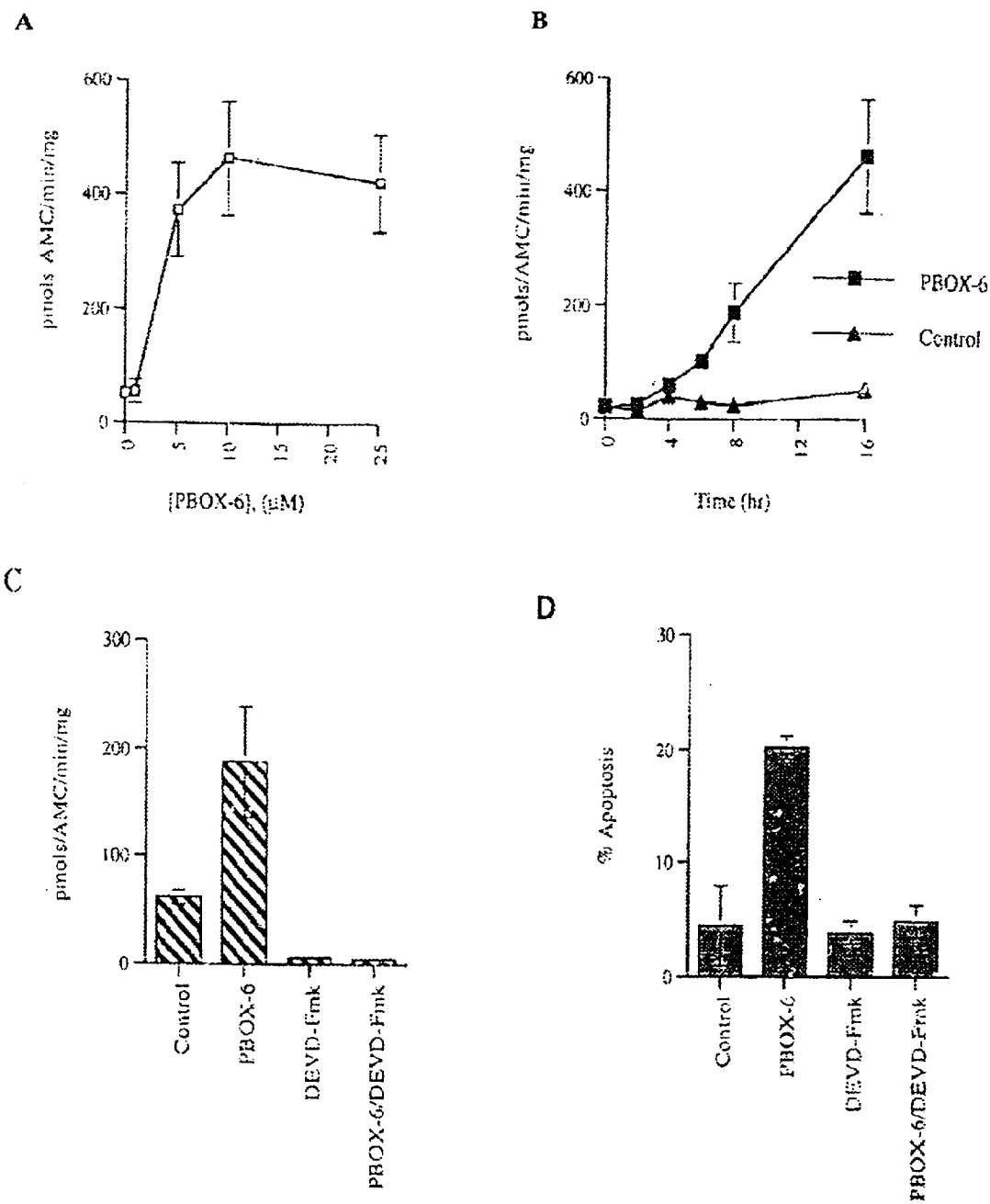

Fig. 4. PBOX-6 induces apoptosis through activation of caspase-3-like proteases. HL-60 cells were seeded at a density of 3 x $10^5$ cells/ml and were treated with either (A) a range (0-50μM) of concentrations of PBOX-6 for 16 hours or (B) one concentration of PBOX-6 (10μM) for a period of 2, 4, 6, 8 and 16 hours or (C and D) pretreated with z-DEVD-fmk (200μM) for 1 h followed by treatment with PBOX-6 for a further 8h. Cytosolic extracts were prepared and assayed for caspase-3-like protease activity as described in the Methods section. The percent apoptosis and necrosis was determined by cytospinning and staining the cells using the RapiDiff kit. Values represent the mean +/- SEM of three separate experiments.

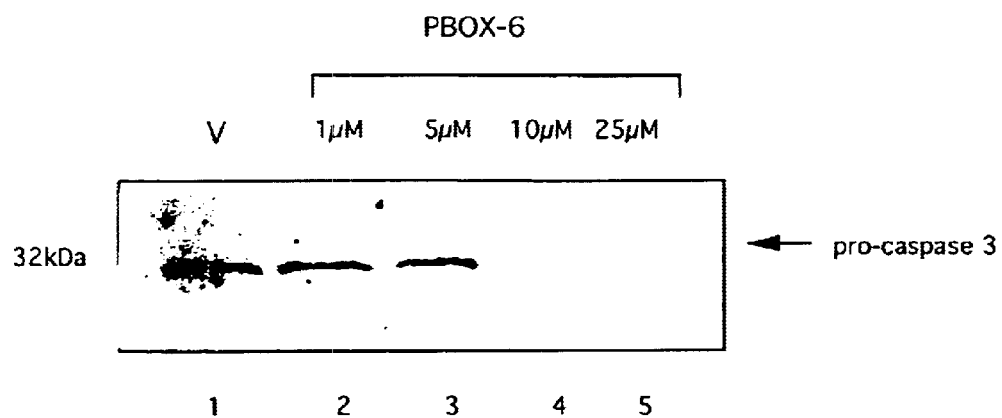
Fig. 5. Disappearance of pro-caspase 3 in HL-60 cells in response to PBOX-6 treatment.
Extracts from HL-60 cells were prepared, treated with either vehicle (ethanol) or a range of concentrations (1μM, 5μM, 10μM and 25μM) of PBOX-6 for 16 h. Samples (30μg of protein) were resolved by SDS-PAGE and probed for pro-caspase 3. Results are representative of at least two separate experiments. V, vehicle.

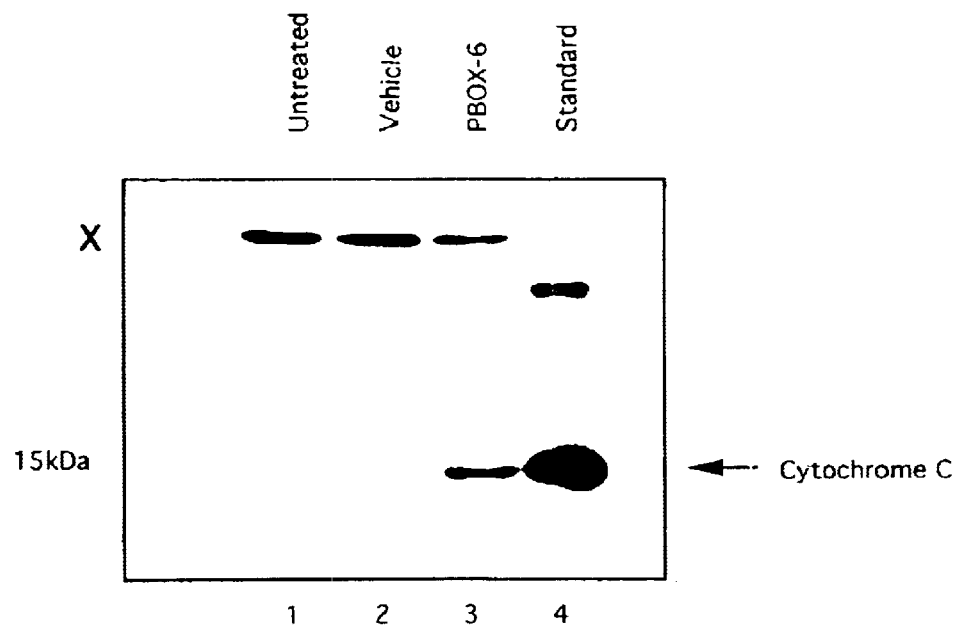

Fig. 6. Accumulation of Cytochrome C in response to PBOX-6.
Cytosols from HL-60 cells, were prepared as described in Methods section treated with either control (untreated), vehicle (ethanol) or PBOX-6 (10µM) for 16 h. Samples (30µg of protein) were resolved by SDS-PAGE and probed for Cytochrome C as described in the Methods section. The arrow denotes the position of Cytochrome C, horse Cytochrome C being used as a standard. The upper band in lane 4 is due to a dimer of the standard Cytochrome C sample. The X denotes a protein band that cross-reacted with the antibody as previously described (Liu et al., 1996). Results are representative of at least two separate experiments.

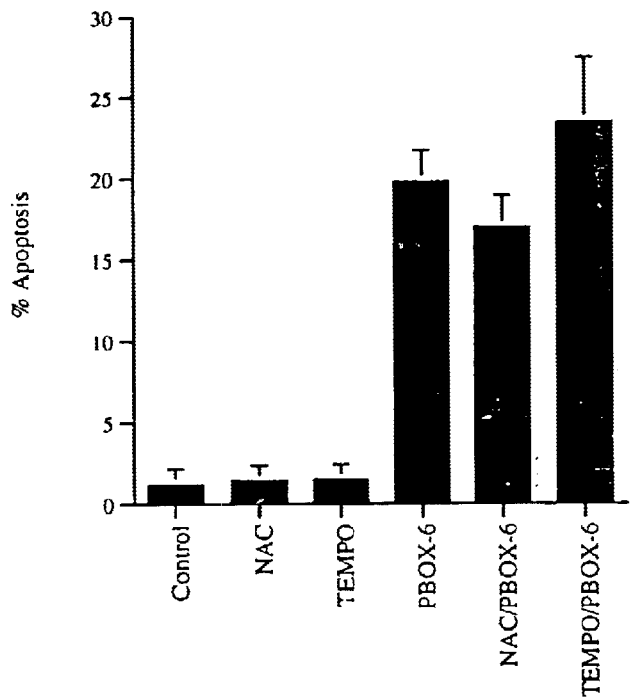

Fig. 7. N-acetylcysteine or TEMPO pre-treatment does not protect HL-60 cells against PBOX-6-induced apoptosis.
HL-60 cells were seeded at a density of $3 \times 10^5$ cells/ml, and were pre-treated with either N-acetylcysteine (NAC) (5mM) or TEMPO (1μM) for 30 min followed by treatment with PBOX-6 for a further 8h. Percent apoptosis was determined by cytospinning and staining the cells using the RapiDiff kit as described in the Methods section. Values represent the means ± range of two separate experiments.

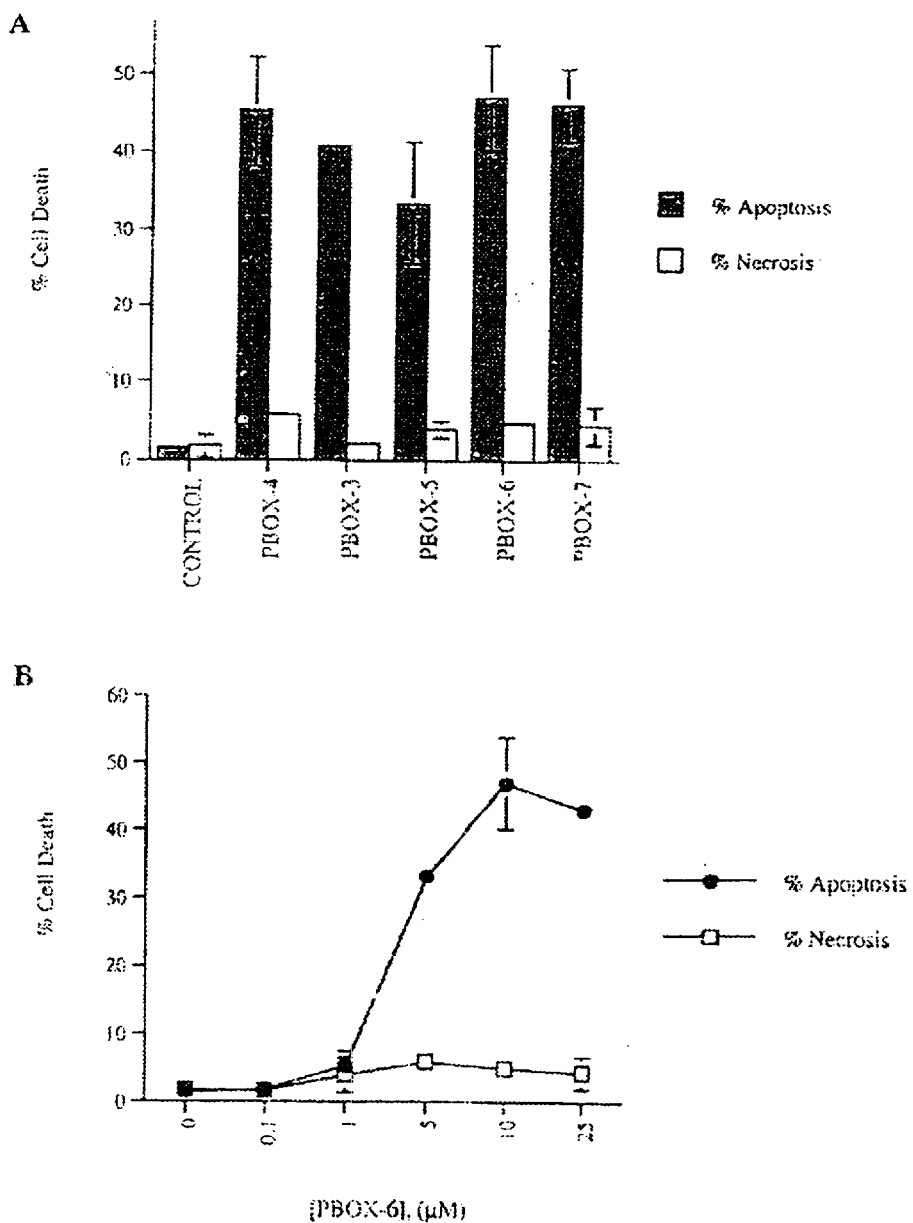

Fig. 8. Pyrrolo-1,5-benzoxazepines induce apoptosis in Jurkat cells.
Jurkat cells were seeded at a density of $3 \times 10^5$ cells/ml and were incubated with (A) either one of the indicated PBOX drugs, each at a final concentration of 10μM or (B) a range of concentrations of PBOX-6. The control wells in each case contained 0.5% (v/v) ethanol. After 16h the percent apoptosis and necrosis was determined by cytospinning and staining the cells using the RapiDiff kit as described in the Methods section. Values represent the mean +/- SEM for three separate experiments.

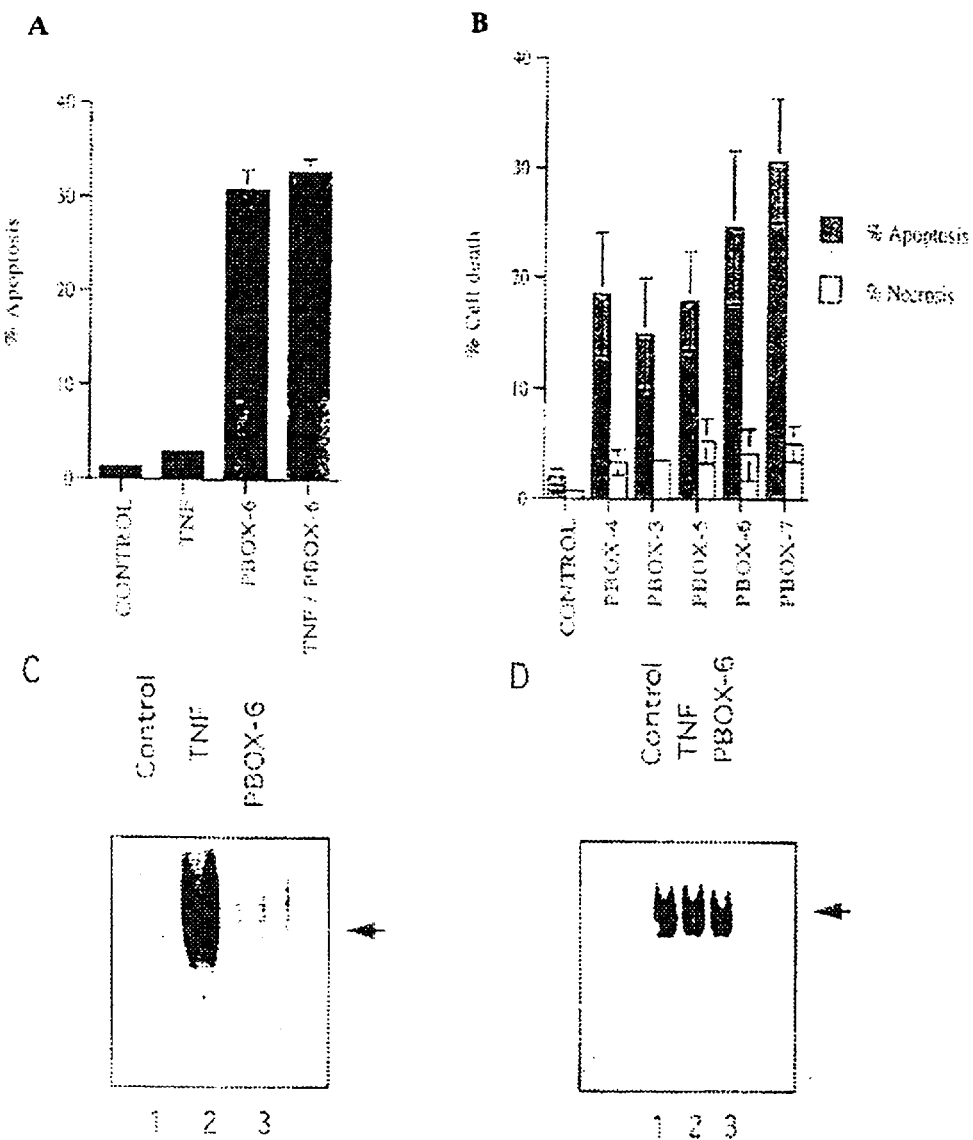

Fig. 9. Lack of involvement of NFκB in pyrrolobenzoxazepine-induced apoptosis. (A) HL-60 cells were seeded at a density of 3 x 10⁵ cells/ml, and were pre-treated with TNFα (10ng/ml) for 1h followed by treatment with PBOX-6 for a further 16h. The control wells in each case contained 0.5% (v/v) ethanol. Values represent the mean +/- SEM of three separate experiments. (B) Same as in (A) but with Hut-78 cells incubated with either one of the indicated PBOX drugs, each at a final concentration of 10μM. Nuclear extracts (2μg) were prepared from (C) HL-60 cells treated either with control (0.5% (v/v) ethanol), TNFα (10ng/ml) or PBOX-6 (10μM) for 16 hours or (D) Same as in (C) but with Hut-78 cells. NFκB activity was then measured by EMSA described in the Methods section. The arrowhead represents NFκB-DNA. Results are representative of at least two separate experiments.

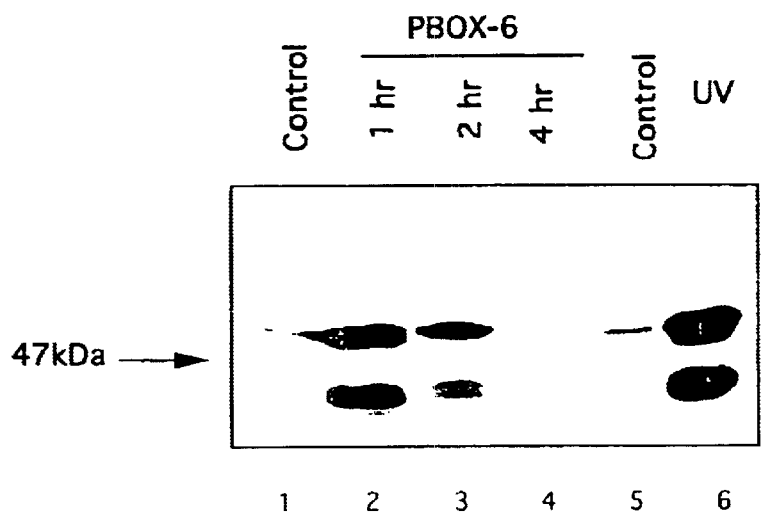

Fig. 10. PBOX-6 induces transient activation of JNK in HL-60 cells.
HL-60 cells were treated with either control (ethanol) or PBOX-6 for 1,2 or 4 hr. A positive control for JNK activation was also set up by exposing the cells to UV light for 2 min followed by a 1 hr incubation at 37C. Cytosolic extracts were then prepared and samples (30μg of protein) were resolved by SDS-PAGE and probed for activated phosphorylated JNK. The two bands refer to the two JNK isoforms present (JNK 1 and JNK2, 45kDa and 54kDa respectively). Results are representative of at least two separate experiments.

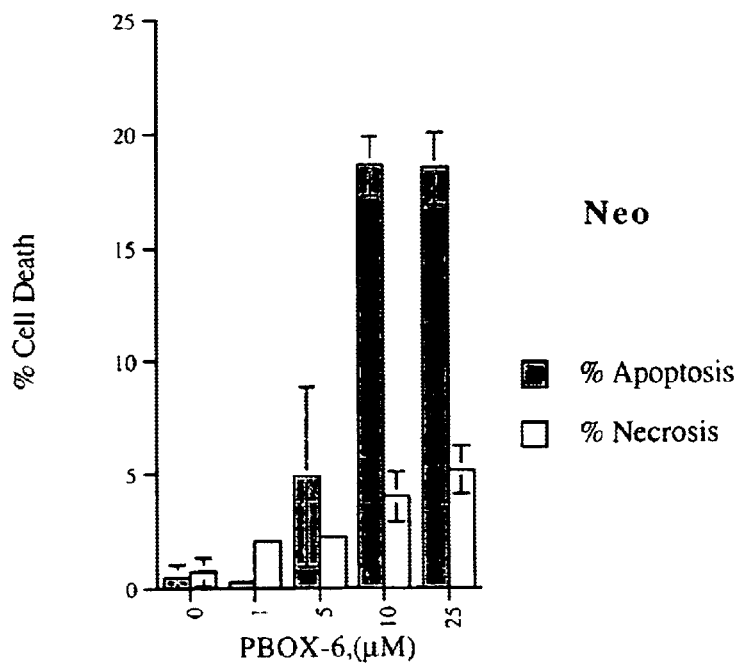

Fig. 11. PBOX-6 induces apoptosis in normal (neo) CEM cells.
CEM cells were seeded at a density of 3 x 10⁵ cells/ml and were incubated with a range of concentrations of PBOX-6. The control wells in each case contained 0.5% (v/v) ethanol. After 16h the percent apoptosis and necrosis was determined by cytospinning and staining the cells using the RapiDiff kit as described in the Methods section. Values represent the means ± SEM for three separate experiments.

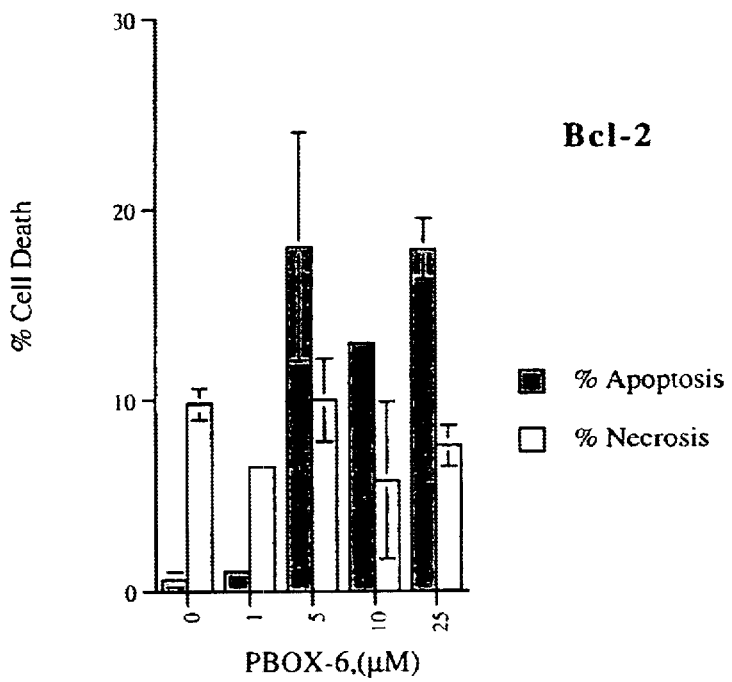

Fig. 12. PBOX-6 induces apoptosis in Bcl-2 overexpressed CEM cells.
CEM cells, overexpressed with Bcl-2, were seeded at a density of $3 \times 10^5$ cells/ml and were incubated with a range of concentrations of PBOX-6. The control wells in each case contained 0.5% (v/v) ethanol. After 16h the percent apoptosis and necrosis was determined by cytospinning and staining the cells using the RapiDiff kit as described in the Methods section. Values represent the means ± SEM for three separate experiments.

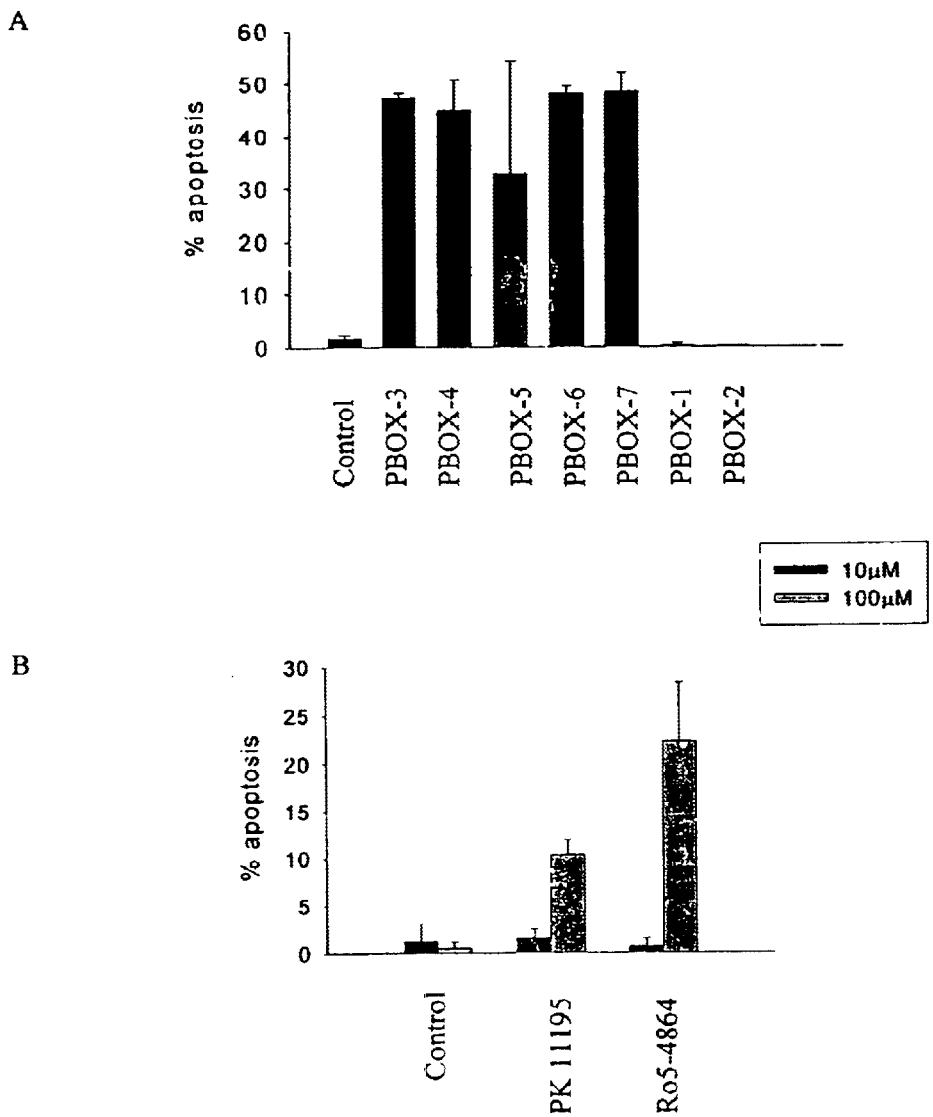

Fig. 13 Some pyrrolo-1,5-benzoxazepines and other PBR ligands induce apoptosis in K562 cells.

K562 cells were seeded at $3 \times 10^5$ cells per ml and treated with (A) the indicated PBOX compound (10μM) for 16 hours or (B), PK 11195 or Ro5-4864 at either 10μM or 100μM. In each case a control was set up which contained 1% ethanol (v/v). Percent apoptosis was determined by cytospinning an aliquot (200μl) onto a glass slide and staining the cells using the RapiDiff kit. Values represent the mean +/- the range of 2 separate experiments.

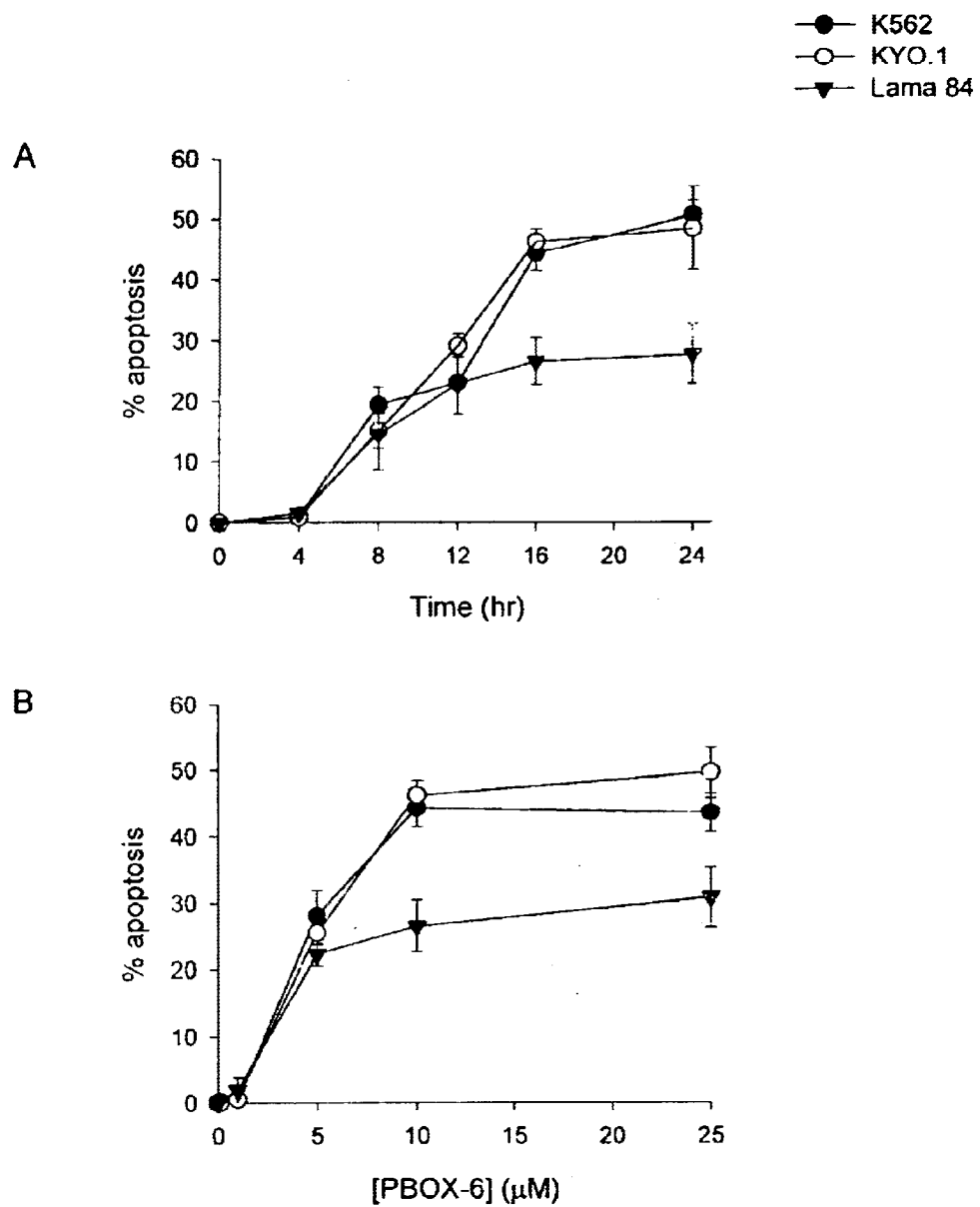

Fig. 14 PBOX-6 induced apoptosis in CML cells is time and dose-dependent.

CML cells were seeded at $3 \times 10^5$ cells per ml and were treated with (A) PBOX-6 (10μM) for a period of 4, 8, 12, 16 and 24 hours or (B) a range (0-25μM) concentrations of PBOX-6 for 16 hours, The percent apoptosis was determined by cytospinning and staining cells with the RapiDiff kit. Values represent the mean +/- SEM of 3 separate experiments.

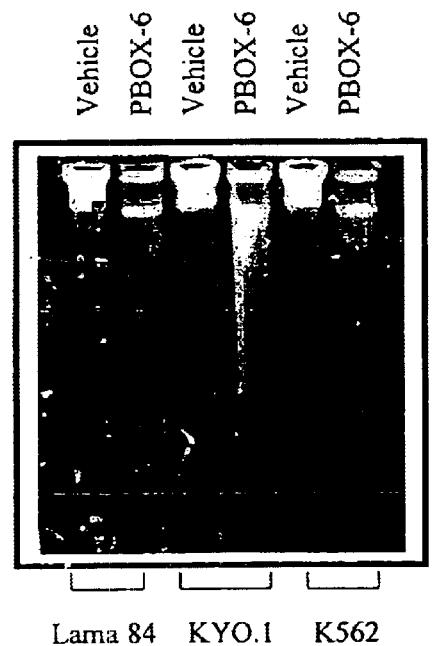
Fig. 15 PBOX-6 induces internucleosomal DNA fragmentation in CML cells.
Cells (1x10⁷) were treated with either vehicle (1% ethanol) or PBOX-6 (10μM) for 48 hours and DNA (45μl) was resolved on an agarose gel (1.5%). DNA ladders were visible under UV light. Results are representative of at least 2 separate experiments.

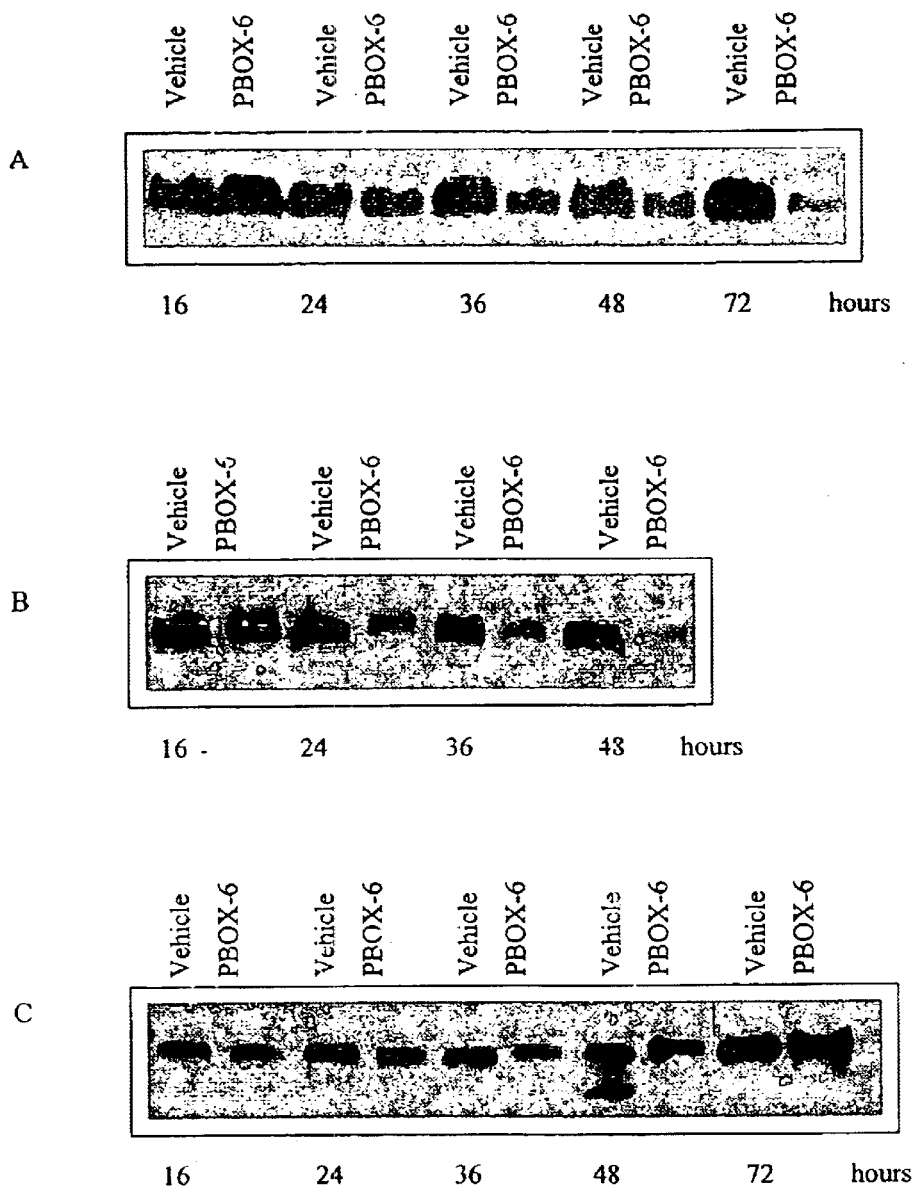

Fig. 16 Downregulation of BCR-abl in K562 and KYO.1, but not in Lama 84 cells in response to PBOX-6 treatment.

Cytosolic extracts were prepared from (A) K562 (B) KYO.1 and (C) Lama 84 cells following treatment with either vehicle (1% ethanol) or PBOX-6 (10μM) for 16, 24, 36, 48 and 72 hours. Protein (40μg) was resolved by SDS-PAGE and probed with anti-c-abl antibody. Results are representative of at least two separate experiments.

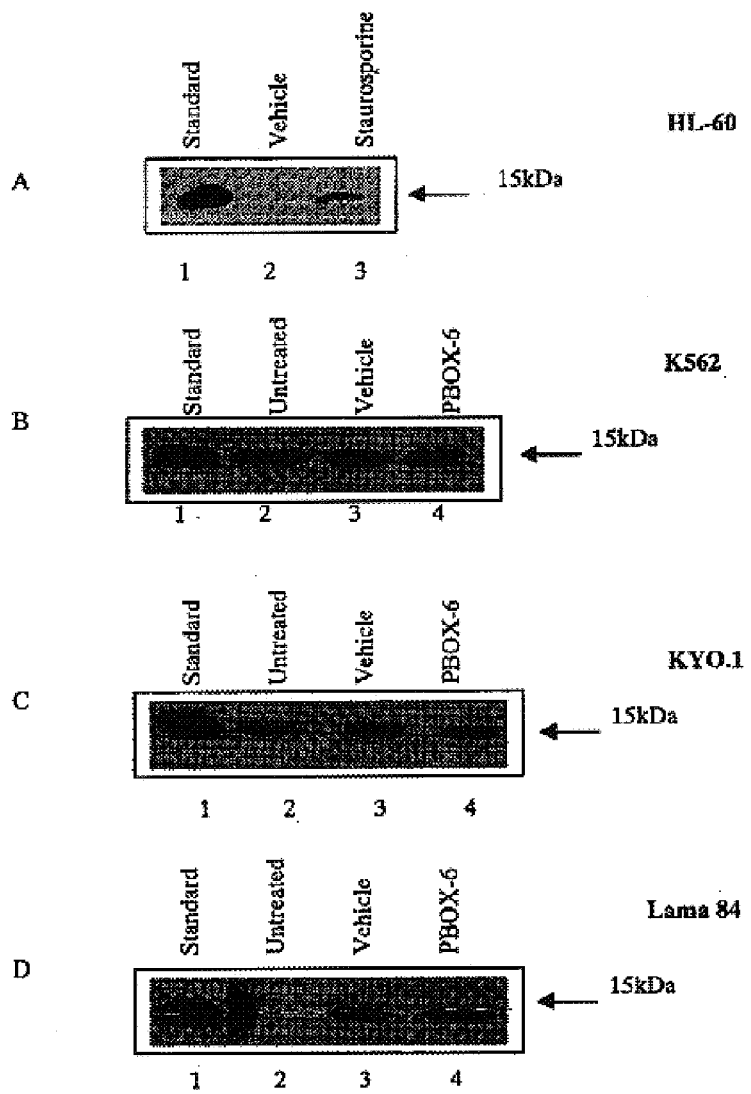

Fig. 17 Cytochrome C western blotting

Cytosolic extracts were prepared from HL-60 cells (A) which were treated with either (lane 2-3), vehicle (0.1% DMSO) or staurosporine (1μM) for 6 hours. K562 (B), KYO.1 (C) and Lama 84 cells (D) were treated with either (lane 2-4) control (untreated), vehicle (1% ethanol) or PBOX-6 (10μM) for 16 hours. Protein (30μg) was resolved by SDS-PAGE and probed for cytochrome C. Horse Cytochrome C was used as a standard in each case (lane 1). Results are representative of at least 2 separate experiments.

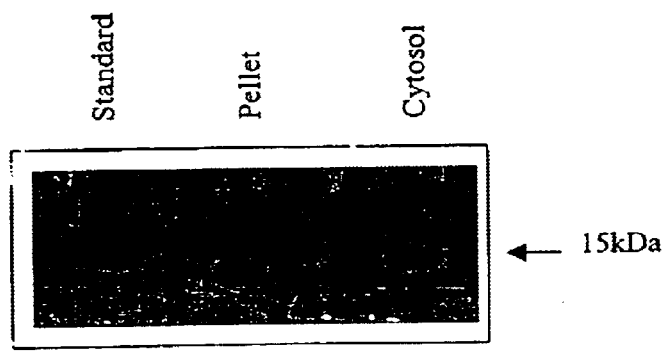

Fig. 18 Cytochrome C is not all non-specifically released from Mitochondria during sample preparation.

Cytosolic extracts from untreated K562 cells were prepared and the remaining pellet was solubilised in 100μl of buffer and incubated on ice for 30 min. Samples were centrifuged and the resulting superantant was removed. Protein (50μg) from the solubilised pellet (lane 2) and from the cytosol (lane 3) were resolved by SDS-PAGE and probed with anti-cytochrome C. Horse cytochrome C was used as a standard (lane 1).

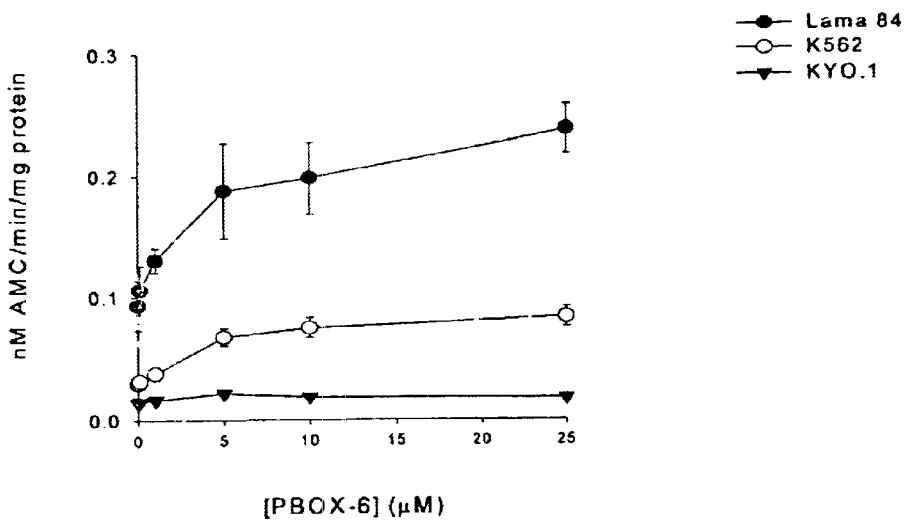

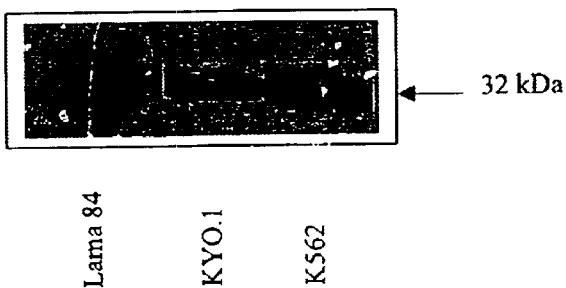

Fig. 19 Activation of caspase 3 in K562 and lama 84 but not KYO.1 cells in response to PBOX-6 treatment.

In (A) CML cells were seeded at $5 \times 10^6$ cell per sample and treated with a range (0-25µM) of PBOX-6 concentrations for 16 hours. Cytosolic extracts were prepared and enzyme extracts (100µg) were incubated with substrate (20µM) in a total volume of 3 ml. All values represent the mean +/- SEM of three separate experiments. In (B) cytosolic extracts from $6 \times 10^6$ untreated CML cells were prepared and protein (45µg) was resolved by SDS-PAGE before probing with anti-caspase 3 antibody. Results are representative of 2 separate experiments

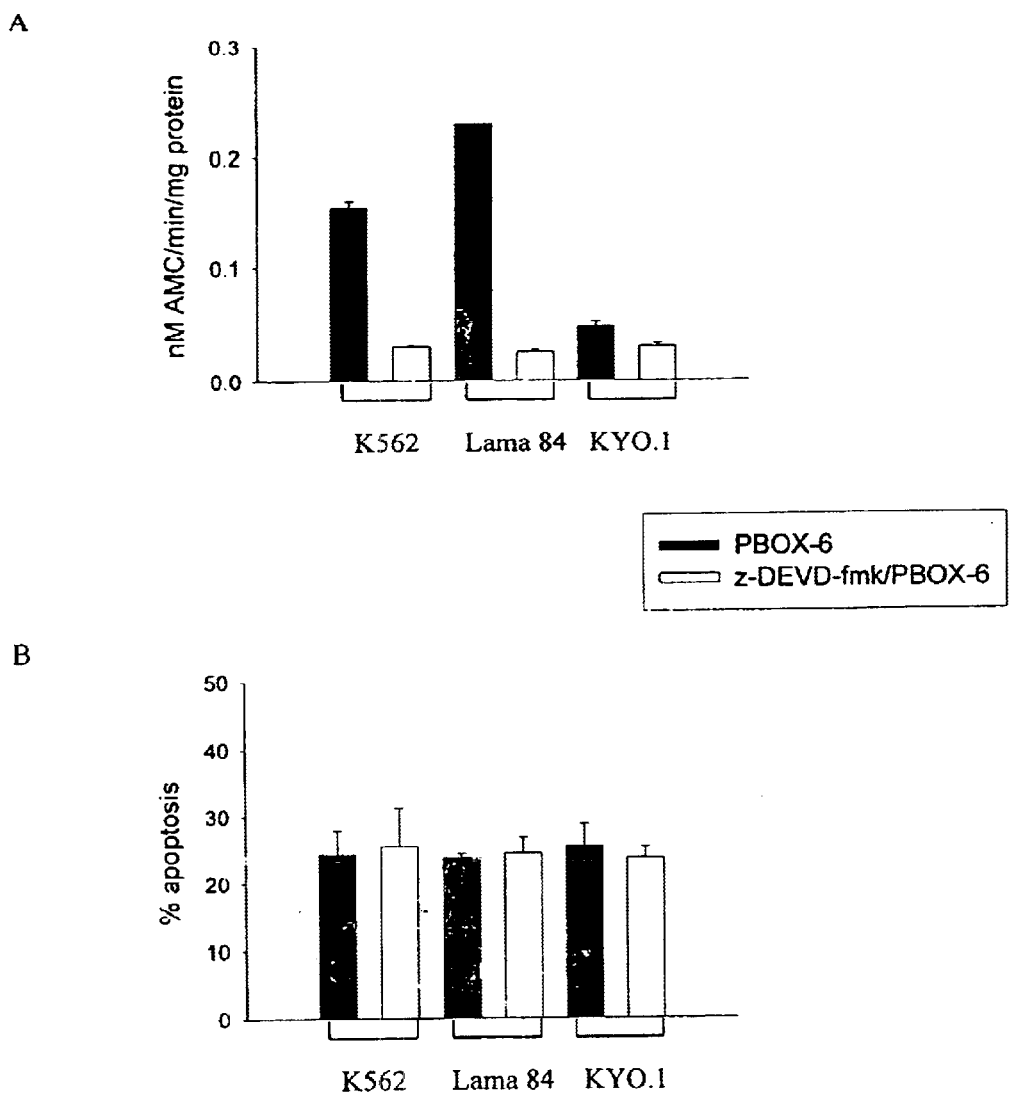

Fig. 20 Caspase 3 inhibitor, z-DEVD-fmk, fails to protect against PBOX-6 induced apoptosis in CML cells.

CML cells were seeded at (A) $5 \times 10^6$ cells per ml and treated with PBOX-6 (10μM) for 16 hours. Cytosolic extracts were prepared and enzyme extracts (100μg) were incubated with or without z-DEVD-fmk for 1 hour at room temperature prior to the addition of caspase 3 substrate (20μM). CML cells were seeded at (B) $3 \times 10^5$ cells per ml and pretreated with z-DEVD-fmk for 1 hour prior to treatment with PBOX-6 (10μM) for a further 8 hours. Percent apoptosis was determined by RapiDiff staining. Values represent the mean +/- SEM of 3 separate experiments.

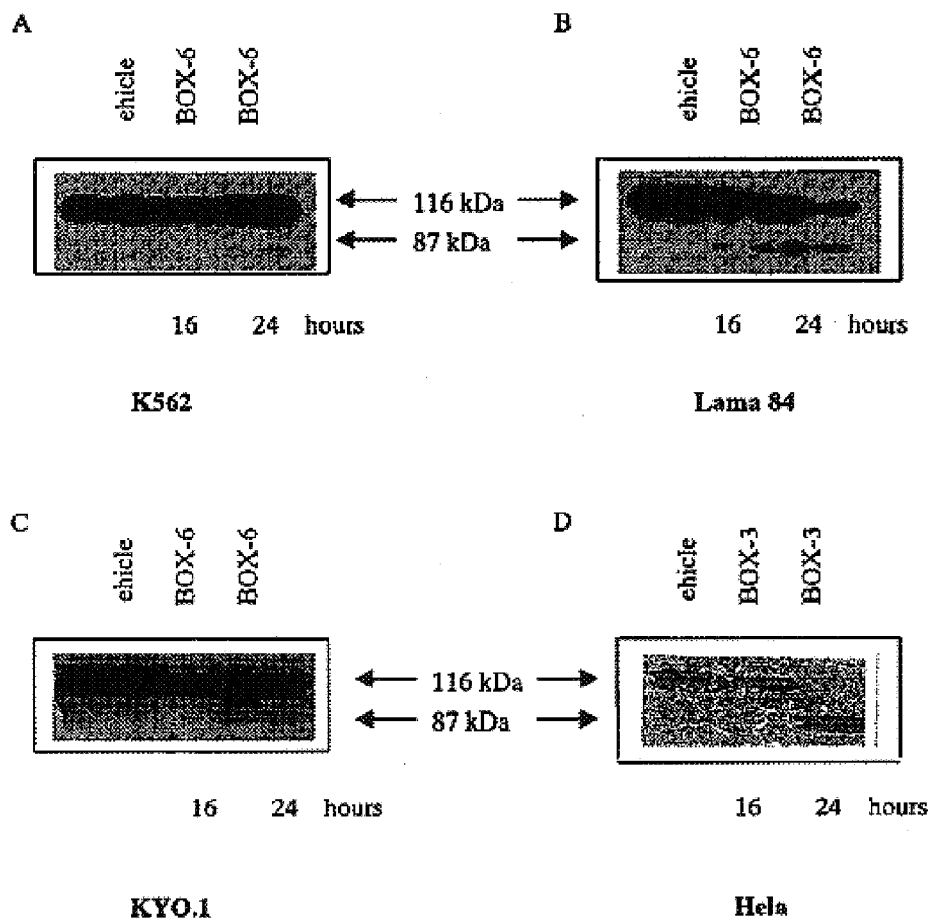

Fig. 21 Induction of PARP cleavage in CML and Hela cells following treatment with PBOX-6 and PBOX-3

Whole cell extracts from K562 (A), Lama 84 (B), and KYO.1 (C) and Hela cells (D) were prepared following treatment with either PBOX-6 (10μM) for 16 and 24 hours (A, B, and C) or PBOX-3 (10μM) for 48 hours (D). In each case a vehicle treated control was set up containing 1% ethanol. Samples were resolved by SDS-PAGE and probed with anti-PARP antibody. Results are representative of at least 2 experiments.

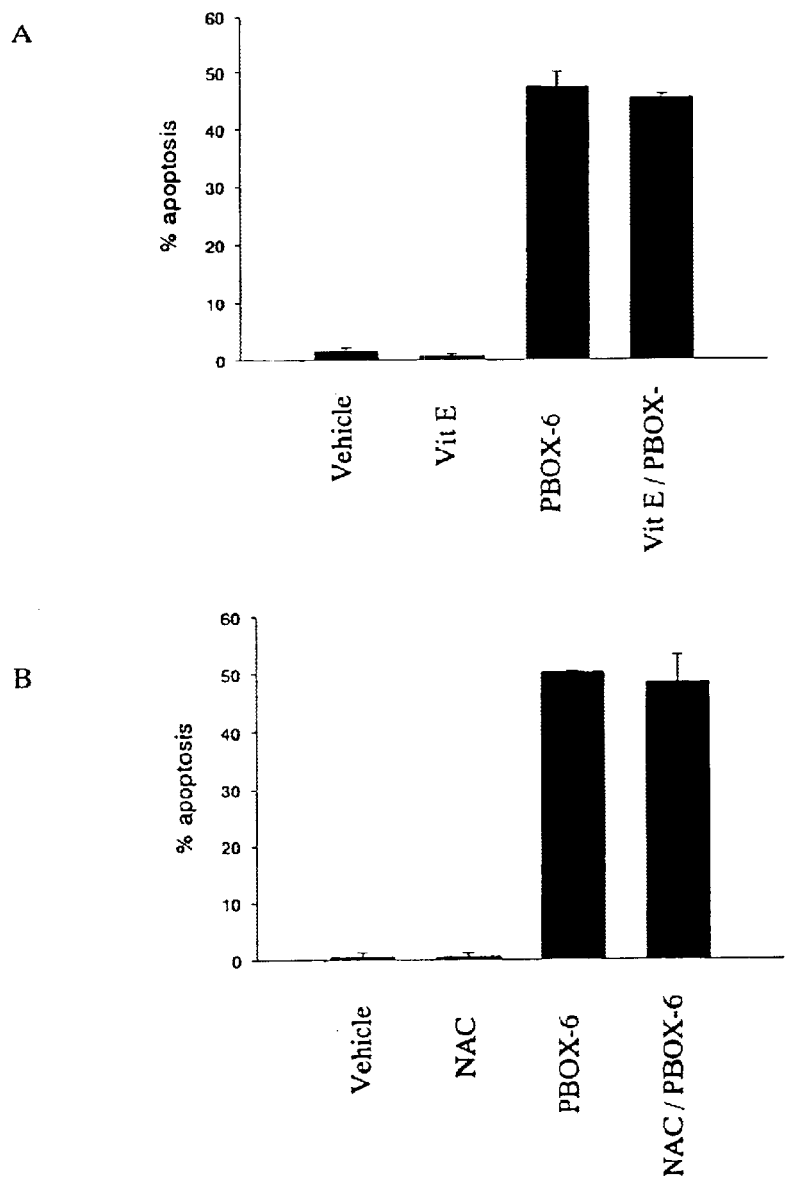

Fig. 22 Antioxidants fail to protect against PBOX-6-induced apoptosis in K562 cells. K562 cells were seeded at $3 \times 10^5$ cells per ml and treated with (A) either vehicle (1% PBS, 0.1% ethanol), Vitamin E (100μM) for 40 hours, PBOX-6 (10μM) for 16 hours or a pretreatment of Vitamin E for 24 hours followed by PBOX-6 for a further 16 hours. In (B) cells were treated with either vehicle (25mM Tris, 0.1% ethanol), N-Acetylcysteine (NAC) (5mM) for 17 hour, or a pretreatment of NAC for 1 hour followed by PBOX-6 for a further 16 hours. Percent apoptosis was determined by RapiDiff staining. Results represent the mean +/- SEM of 3 separate experiments.

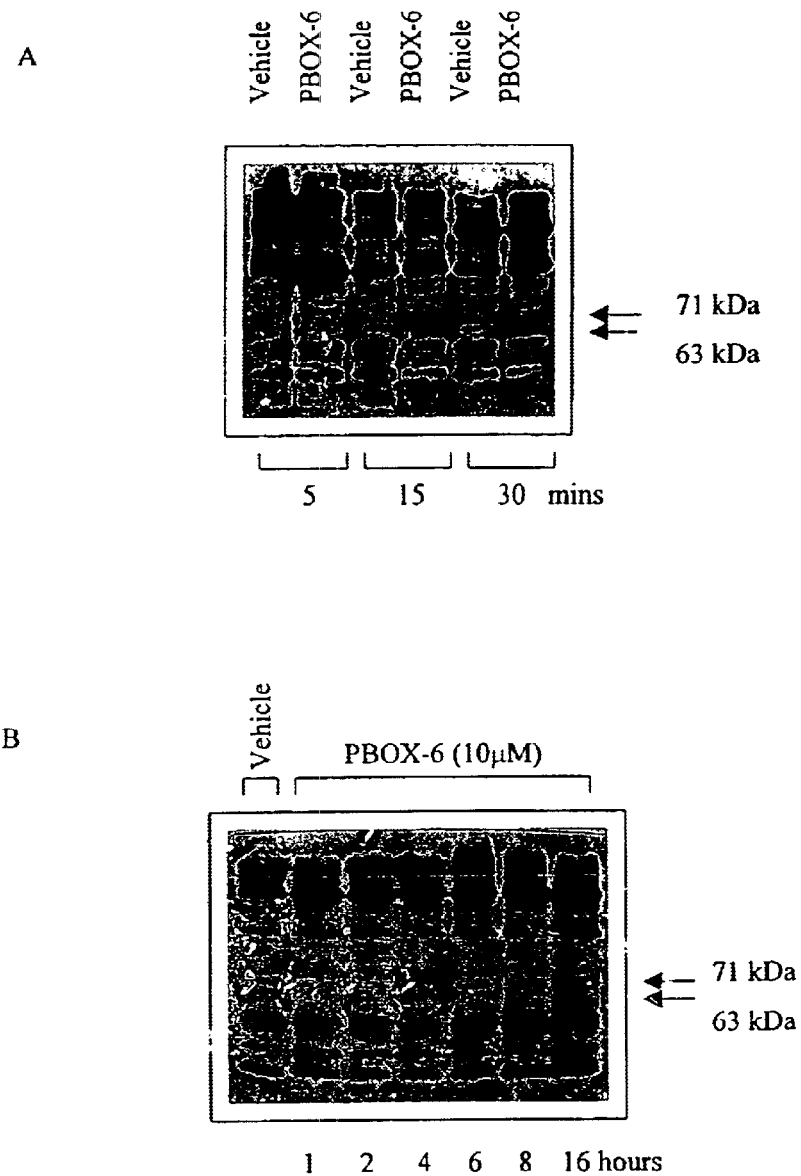
Fig. 23 PBOX-6 alters the tyrosine phosphorylation status of proteins in K562 cells.
K562 cells (5x10$^6$) were treated with vehicle (1% ethanol) or PBOX-6 (10μM) for either (A) 5, 15 and 30 min or (B) 1, 2, 4, 6, 8, and 16 hours. Cytosolic extracts were prepared and protein (40μg) was resolved by SDS-PAGE and probed with anti-phosphotyrosine antibody. Results are representative of at least 2 experiments.

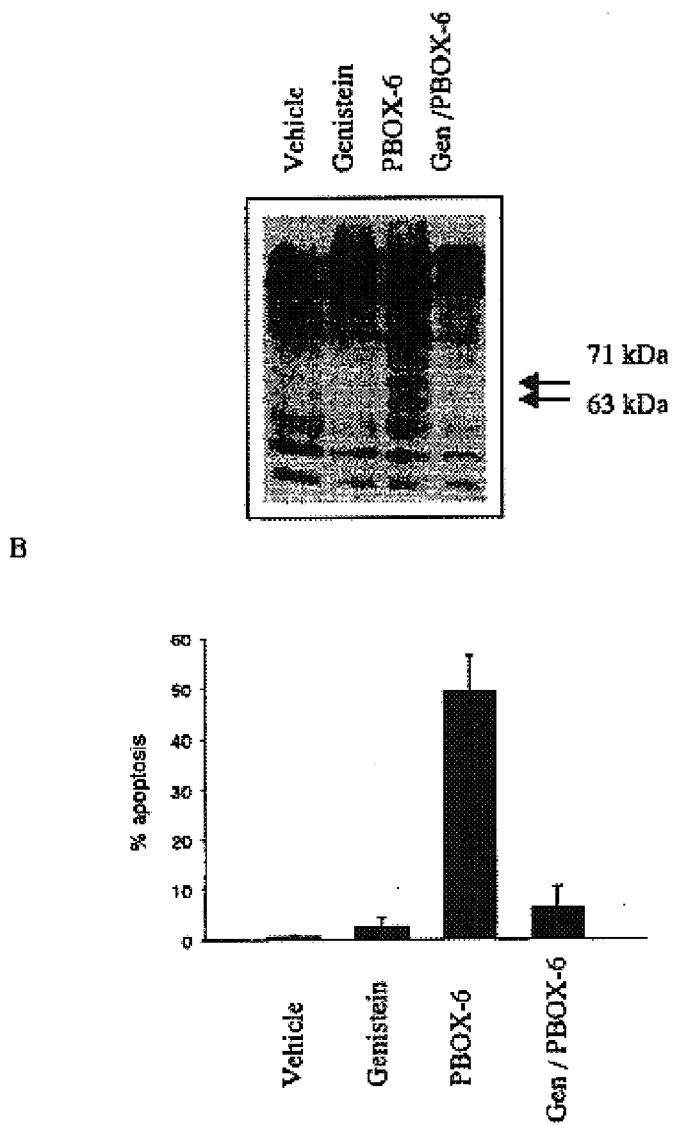

Fig. 24 Pretreatment of K562 cells with the tyrosine kinase inhibitor, Genistein, prevents protein tyrosine phosphorylation and inhibits apoptosis induced by PBOX-6. K562 cells were seeded at (A) $5 \times 10^6$ cells per sample or (B) $3 \times 10^5$ cells per ml and pretreated with genistein (100μM) for 1 hour prior to treatment with PBOX-6 (10μM) for a further 16 hours. In (A) cytosolic extracts were prepared as described in Section 2.10. Protein (40μg) was resolved by SDS-PAGE and probed with anti-phosphotyrosine antibody Results are representative of at least 3 experiments. In (B) percent apoptosis was determined by RapiDiff staining. Results represent the mean +/- SEM of 3 separate experiments.

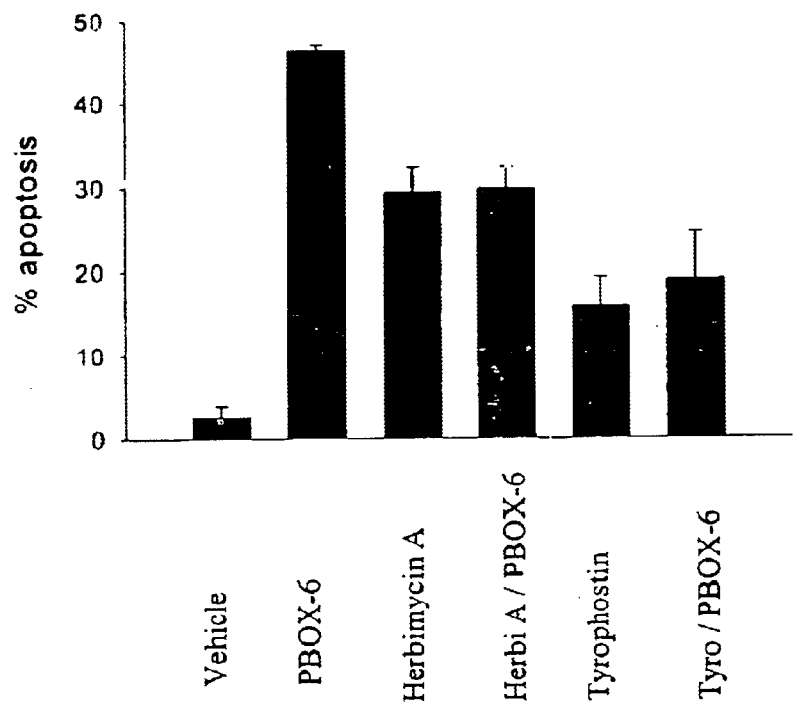

Fig. 25 Herbimycin A and Tyrophostin reduce, but do not completely inhibit, PBOX-6 induced apoptosis in K562 cells.

Cells were seeded at $3 \times 10^5$ cells per ml and were pretreated with either Herbimycin A (5µM) or Tyrophostin (200µM) for 1 hour prior to treatment with PBOX-6 (10µM) for a further 16 hours. Percent apoptosis was determined by cytospinning the cells onto a slide and staining with the RapiDiff kit. Results represent the mean +/- SEM of 3 separate experiments.

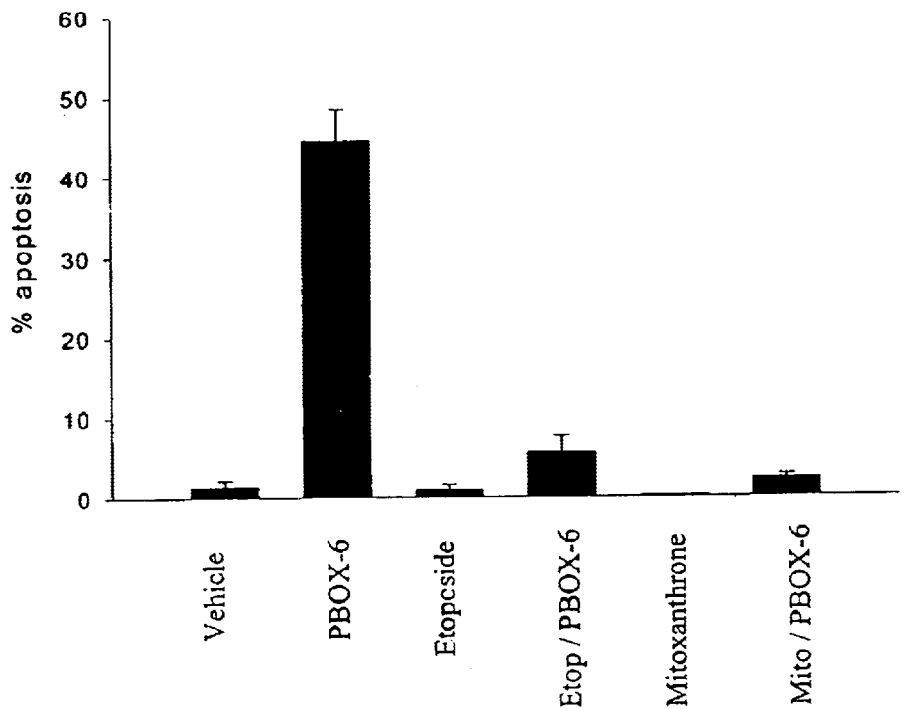

Fig. 26 Etoposide and mitoxanthrone pretreatment of K562 cells protects against PBOX-6 induced apoptosis.

K562 cells were seeded at a density of $3 \times 10^5$ cells per ml and pretreated with either etoposide (50μM) or mitoxanthrone (500nM), for 1 hour, before treating with PBOX-6 (10μM) for a further 16 hours. Percent apoptosis was determined by RapiDiff staining. Values represent the mean +/- SEM of 3 separate experiments.

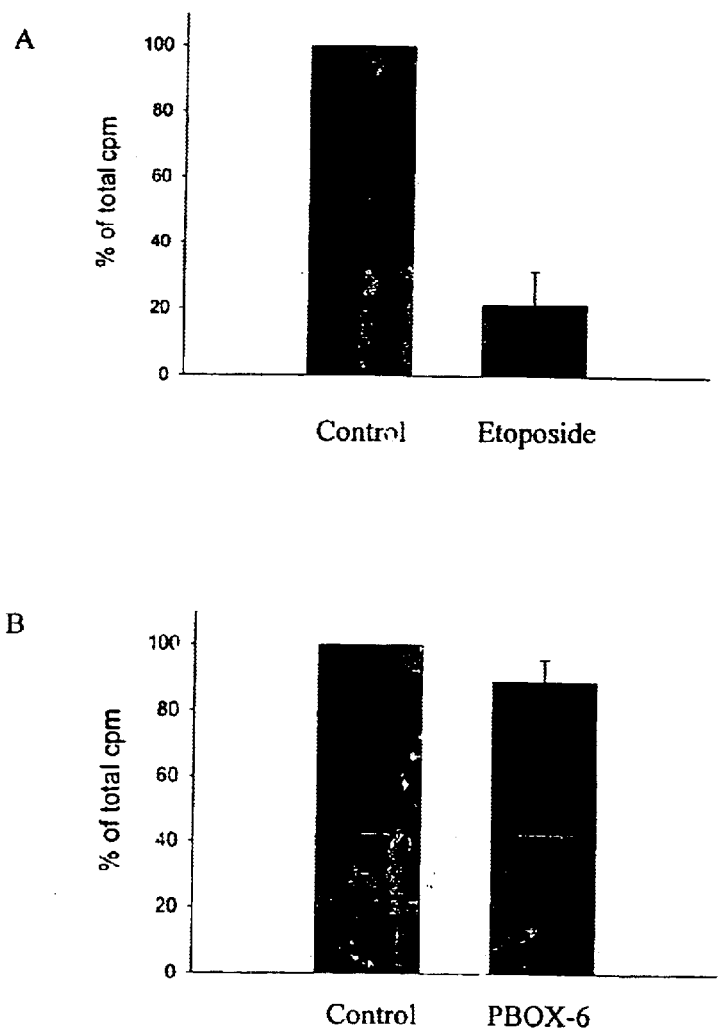

Fig. 27 PBOX-6 does not induce DNA strand breaks in K562 cells.

Jurkat cells (A) were treated with vehicle (0.1% ethanol:DMSO (1:1)) or etoposide (2.5µM) for 1 hour and K562 cells (B) were treated with vehicle (1% ethanol) or PBOX-6 (10µM) for 3 hours. Cells were lysed on filters and eluted overnight at 0.05ml/min using an alkaline solution. Results represent the mean +/- SEM of 3 separate experiments. Student's t-test was carried out using the Instat programme.

$p < 0.01$ ; etoposide when compared to control $p = 0.2148$ ; PBOX-6 when compared to control

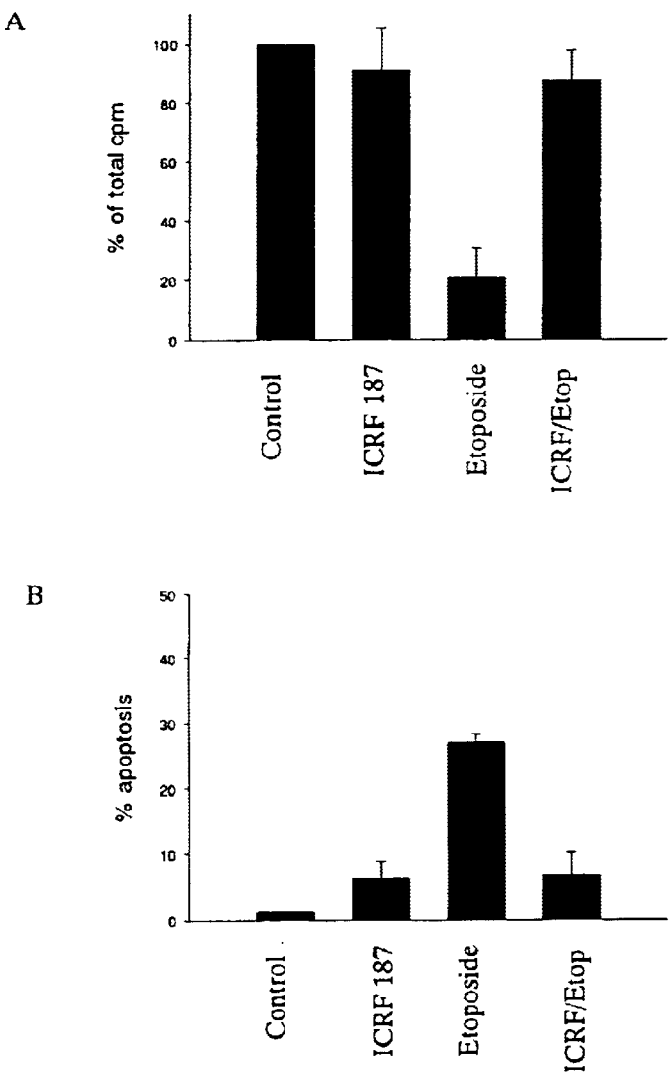

Fig. 28 Pretreatment of Jurkat cells with ICRF 187 inhibits etoposide induced DNA strand breaks and protects against apoptosis.

Jurkat cells were either set up as outlined in Section 1.11 (A) or seeded at $3x10^5$ cells per ml (B) and treated with (A) control (0.1% ethanol:DMSO (1:1)), ICRF 187 (200μM) for 1hour, etoposide (2.5μM) for 1 hour or a pretreatment of ICRF 187 for 1 hour prior to treatment with etoposide for a further hour. Cells were lysed onto filters and eluted overnight. In (B) cells were treated with either vehicle (0.1% ethanol:DMSO (1;1)), ICRF 187 (200μM) for 17 hours, etoposide (2.5μM) for 16 hours or a pretreatment of ICRF 187 for 1 hour followed by etoposide for a further 16 hours. Percent apoptosis was determined by RapiDiff staining. Values represent the mean +/- range of 2 separate experiments.

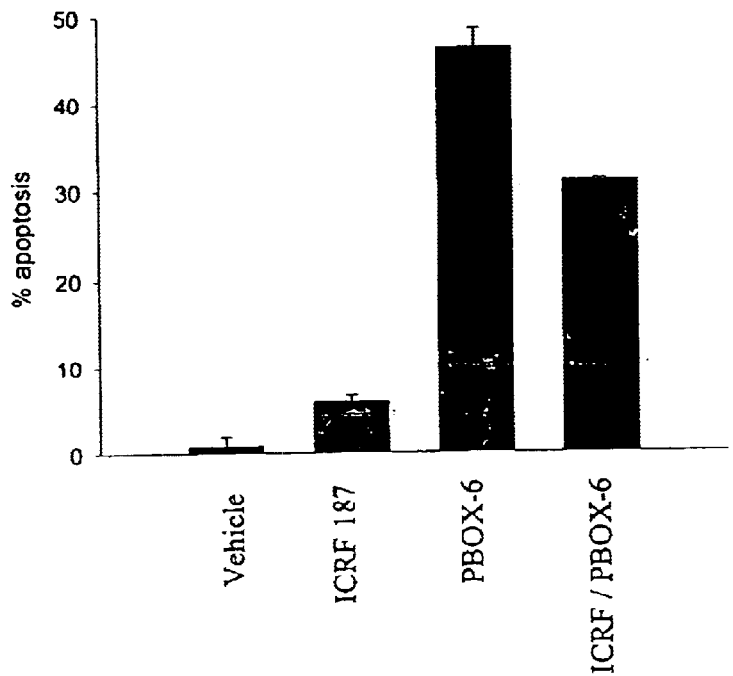

Fig. 29 Pretreatment of K562 cells with ICRF 187 reduces the level of apoptosis induced by PBOX-6.

K562 cells were seeded at $3\times10^5$ cells per ml and treated with either vehicle (1% ethanol), ICRF 187 (200μM) for 17 hours, PBOX-6 (10μM) for 16 hours or a pretreatment of ICRF 187 for 1 hour prior to treatment with PBOX-6 for a further 16 hours. Percent apoptosis was determined by RapiDiff staining. Results are representative of at least 2 separate experiments

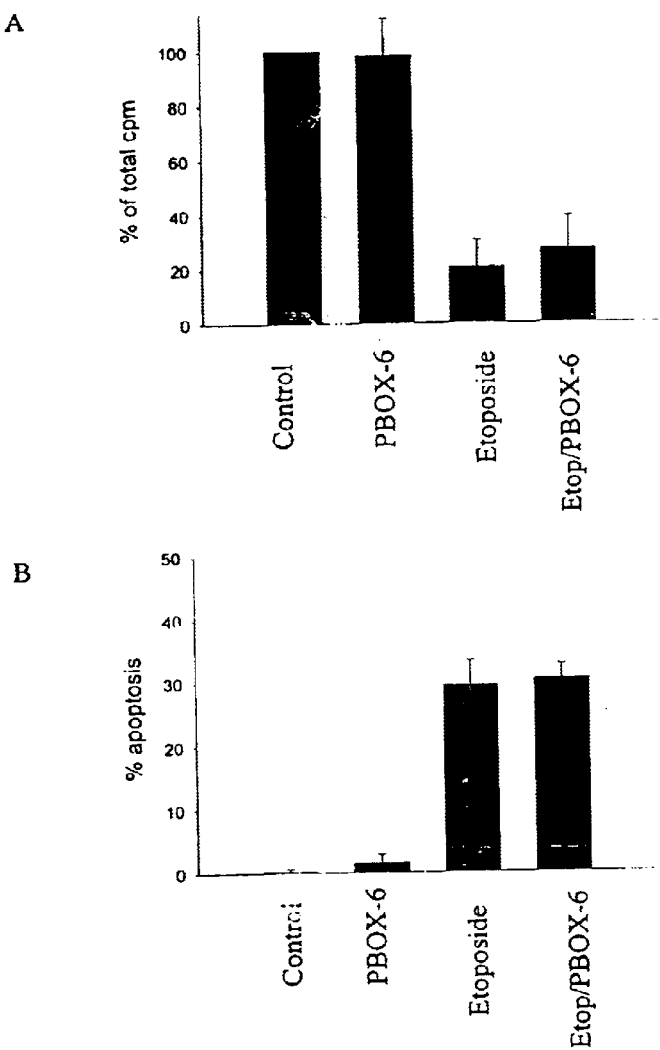

Fig. 30 Pretreatment of Jurkat cells with PBOX-6 failed to protect against DNA strand breaks or apoptosis induced by etoposide.

Jurkat cells were either set up as outlined for alkaline elution (A) or seeded at $3 \times 10^5$ cells per ml (B) and treated with (A) vehicle (1% ethanol, 0.1% DMSO), PBOX-6 (10μM) for 3 hours, etoposide (2.5μM) for 1 hour or a pretreatment of PBOX-6 (0.5μM) for 1 hour followed by etoposide for a further hour. Cells were lysed onto filters and eluted overnight. In (B) cells were treated with vehicle (1% ethanol, 0.1% DMSO), PBOX-6 (0.5μM) for 17 hours, etoposide (2.5μM) for 16 hours or a pretreatment of PBOX-6 for 1 hour followed by etoposide for a further 16 hours. Percent apoptosis was determined by RapiDiff staining. Values represent the mean +/- SEM of 3 separate experiments.

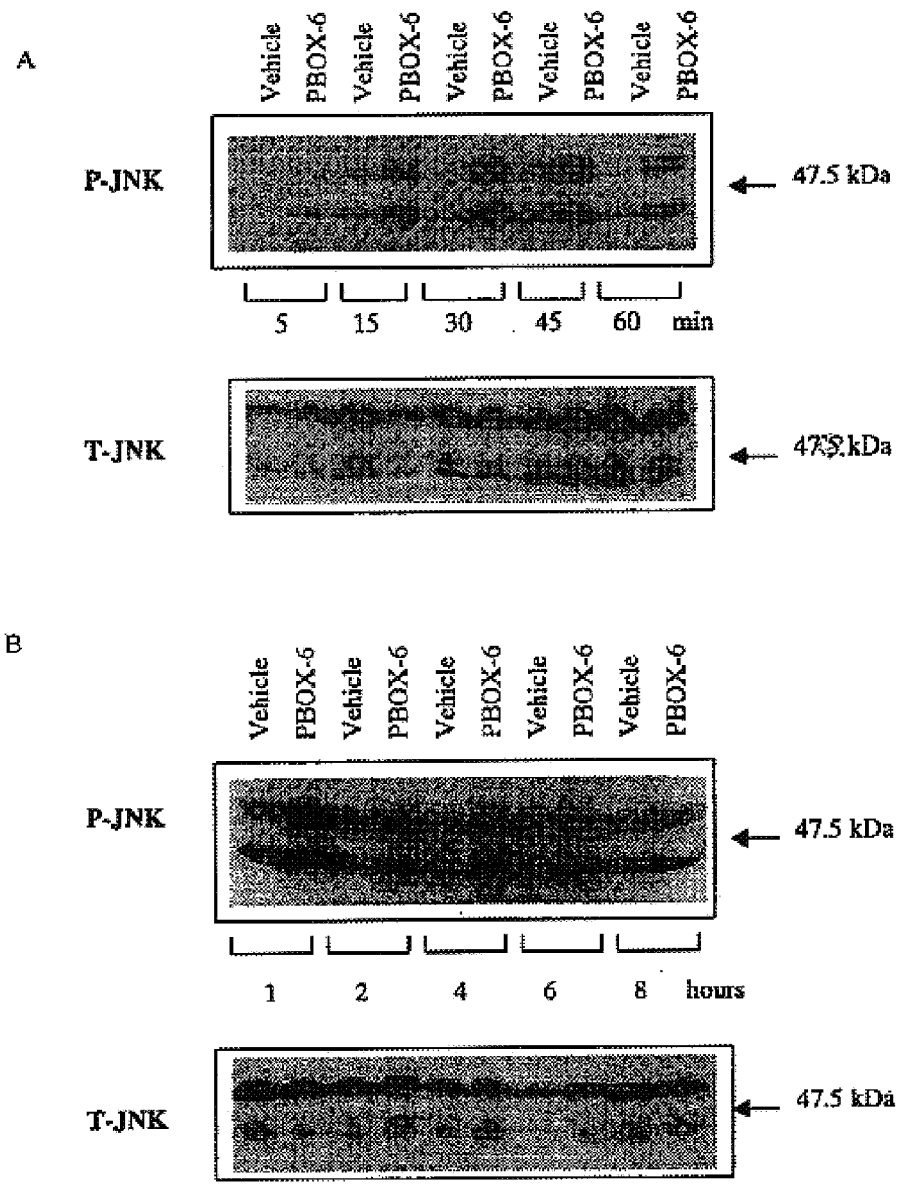

Fig. 31 PBOX-6 induces transient activation of JNK in K562 cells.

K562 cells were seeded at $6 \times 10^6$ cells per sample and treated with either vehicle (1% ethanol) or PBOX-6 (10μM) for (A) 5, 15, 30, 45 and 60 min, or (B) 1, 2, 4 6 and 8 hours. Whole cell extracts were prepared and protein (40μg) was resolved by SDS-PAGE. Blots were probed with anti-JNK phospho antibody an were then stripped and re-probed with anti-JNK total as a loading control. Results are representative of two separate experiments.

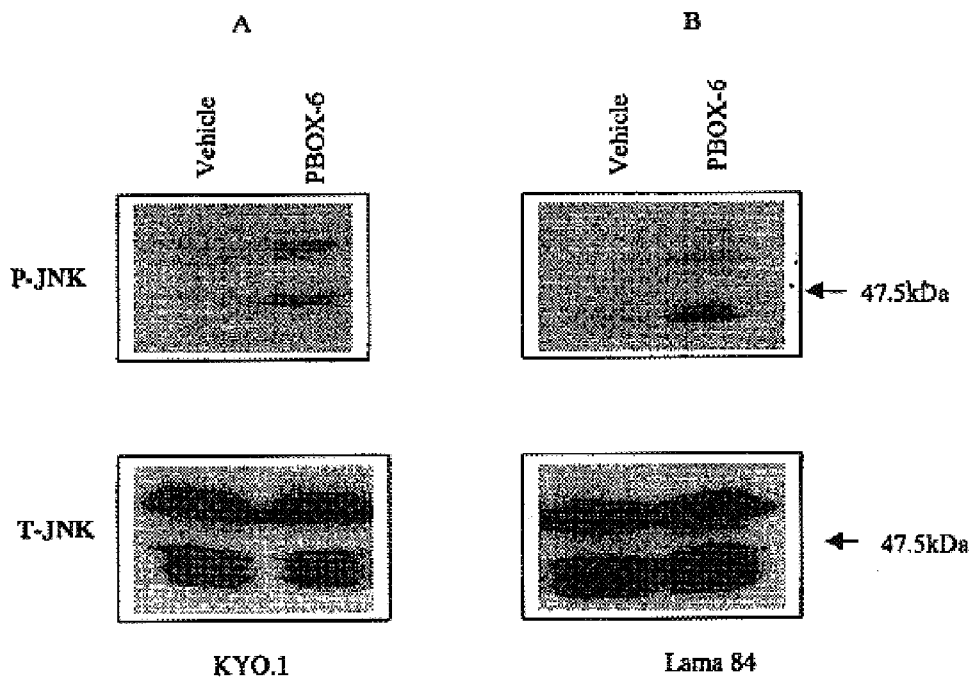

Fig. 32 PBOX-6 induces activation of JNK in KYO.1 and Lama 84 cells.

KYO.1 (A) and Lama 84 cells (B) were seeded at $6 \times 10^6$ cells per sample and treated with either vehicle (1% ethanol) or PBOX-6 (10μM) for 45 minutes. Whole cell extracts were prepared and protein (50μg) was resolved by SDS-PAGE. Blots were incubated with anti-JNK phospho antibody and then stripped and re-probed with anti-JNK total antibody as a loading control. Results are representative of two separate

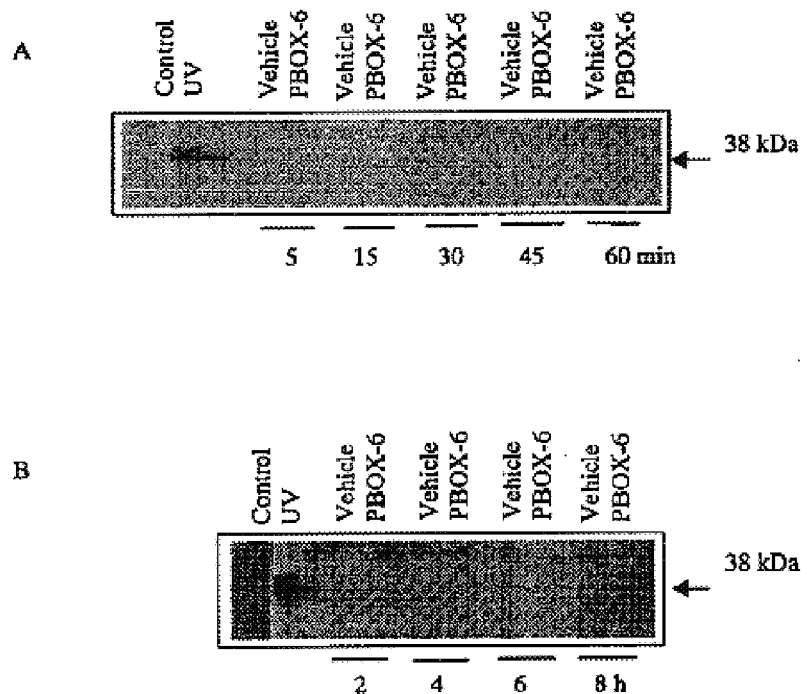

Fig. 33 Lack of activation of p38 in K562 cells in response to PBOX-6.
Cells were seeded at 6x10^6 cells/flask and Jurkat cells (lanes 1-2) were UV irradiated for 2 min and incubated at 37°C for a further 2h. K562 cells (lanes 3-12) were treated with vehicle (1% (v/v) ethanol) or PBOX-6 (10μM) for either (A) 5, 15, 30, 45 and 60 min or (B) 2, 4, 6 and 8h. Whole cell extracts were prepared and equal amounts of protein were resolved by SDS-PAGE and probed with a phospho-specific p38 antibody. Results are representative of two separate experiments.

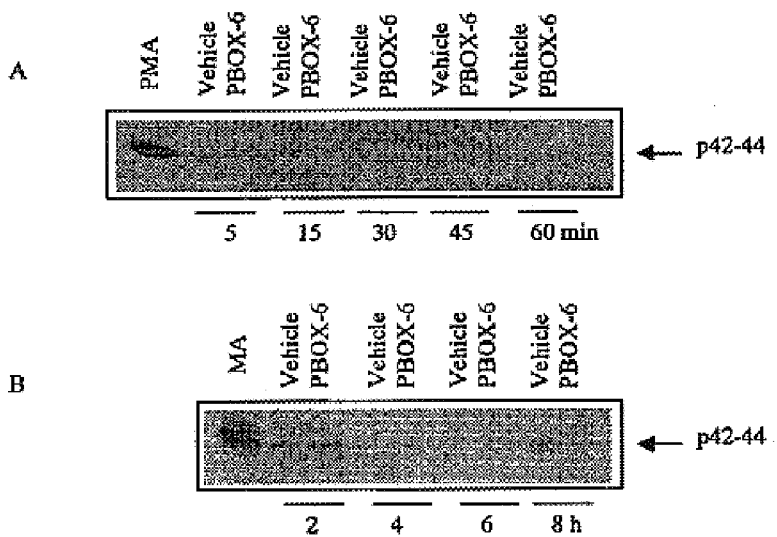

Fig. 34 Lack of activation of p42-44 in K562 cells in response to PBOX-6

K562 cells were seeded at $5 \times 10^6$ cells/flask and treated with PMA (100nM) for 30 min (lane 1) as a positive control or vehicle (1% (v/v) ethanol) or PBOX-6 (10μM) for (A) 5, 15, 30, 45 and 60 min (lanes 2-11) or (B) 2, 4, 6 and 8h (lanes 2-11). Whole cell extracts were prepared and equal amounts of protein (50μg) was resolved by SDS-PAGE and probed with a phospho-specific p42-44 antibody. Results are representative of two separate experiments.

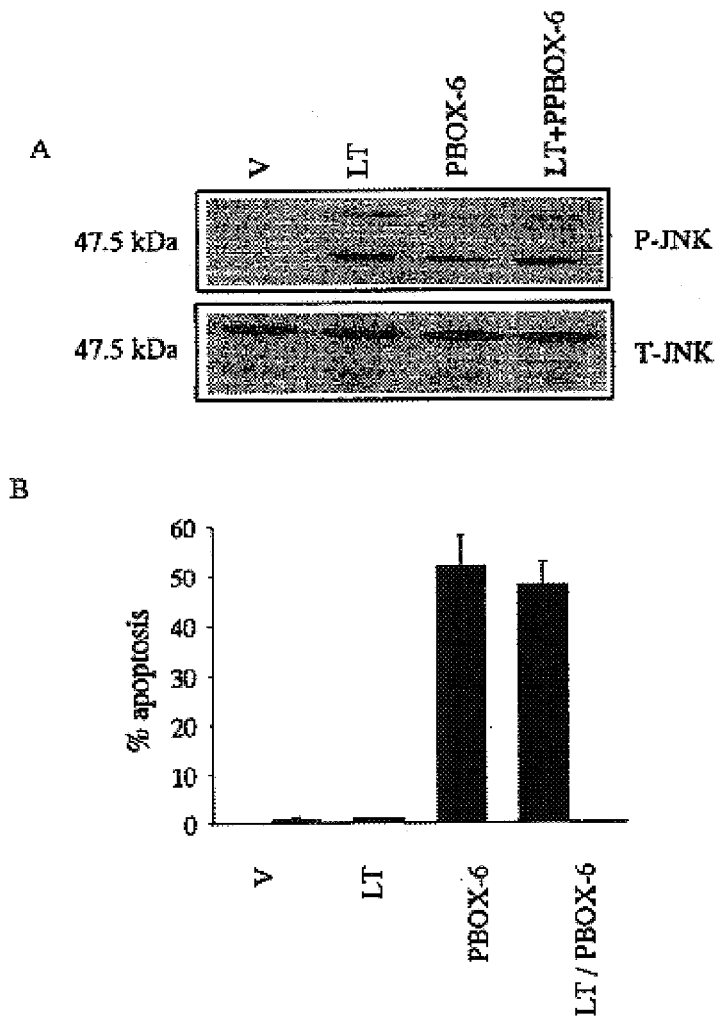

Fig. 35 Pretreatment of K562 cells with an inhibitor of Rac 1, Lethal toxin, failed to protect against PBOX-6 induced JNK activation and apoptosis.

K562 cells were seeded at either (A) 6x10$^6$ cells per sample or (B) 3x10$^5$ cells per m and pretreated with either (A) lethal toxin (500ng/ml) for 3 hours followed by PBOX-6 (10μM) for a further 45 mins. Protein (50μg) was resolved by SDS-PAGE and probe with anti-JNK-phospho antibody. Blots were stripped and re-probed with anti-JNK tota antibody as a loading control. In (B) cells were pretreated with lethal toxin (500ng/ml for 1 hour prior to treatment with PBOX-6 (10μM) for a further 16 hours. Cells were spun onto a slide and percent apoptosis was determined using RapiDiff staining. Results are representative of 2 separate experiments.

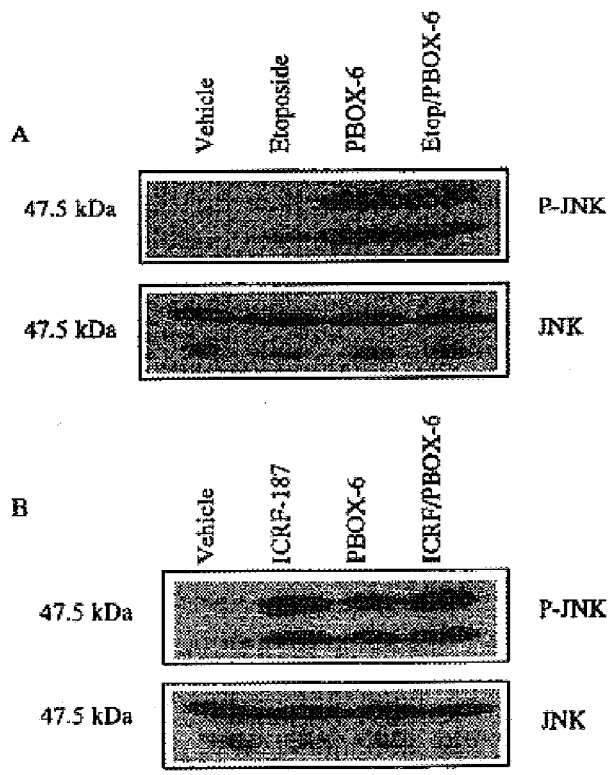

Fig. 36. Activation of JNK lies upstream of a requirement for Topo II in the pathway by which PBOX-6 induces apoptosis in K562 cells.

K562 cells were seeded at $6 \times 10^6$ cells per sample and pretreated with either (A) etoposide (50μM) or (B) ICRF 187 (200μM) for 1 hour prior to treatment with PBOX-6 (10μM) for a further 45 min. Whole cell extracts were prepared and protein (50μg) was resolved by SDS-PAGE. Blots were probed with anti-JNK phospho antibody, stripped and re-probed with anti-JNK total antibody as a loading control. Results are representative of at least two separate experiments.

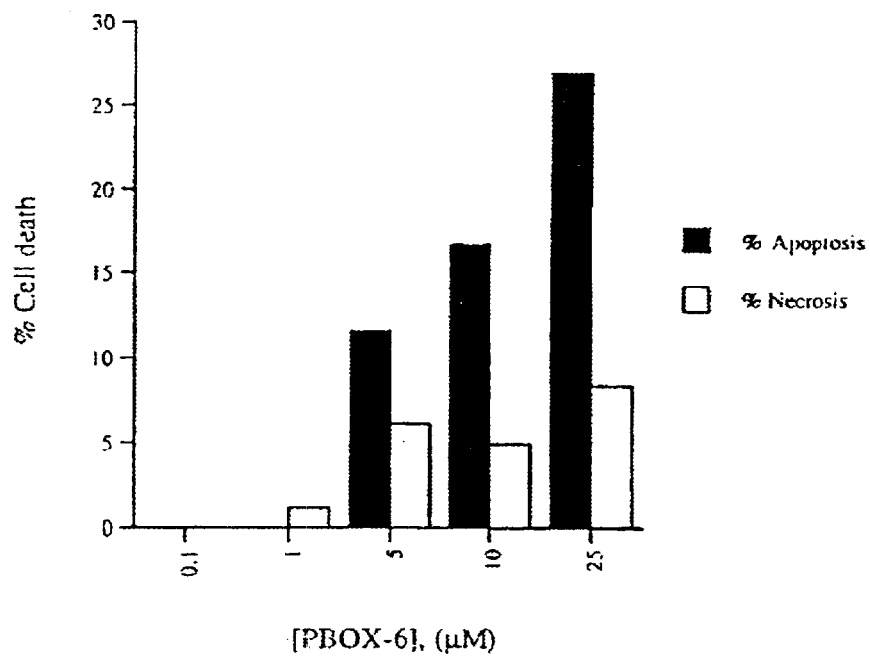

Fig. 37 PBOX-6 induces apoptosis in MCF-7 cells.

MCF-7 cells were seeded at a density of $6 \times 10^6$ cells/ml and were incubated with a range of concentrations of PBOX-6. The control wells in each case contained 0.5% (v/v) ethanol. After 24h the percent apoptosis was determined by cytospinning the cells onto a glass slide and staining them using the RapiDiff kit as described in the Methods section

APOPTOSIS-INDUCING COMPOUNDS

This application is a continuation in part of PCT/IE99/00030 filed May 6, 1999.

The present invention relates to pyrrolobenzoxazepines, pyrrolobenzthiazepines and related compounds having the ability to induce apoptosis, to pharmaceutical compositions comprising these compounds and to their use as anti-tumour agents.

BACKGROUND TO THE INVENTION

Benzodiazepines such as Valium are amongst the most highly prescribed drugs due to their anxiolytic, relaxant and sedative effects. Target-specific binding of benzodiazepines has been observed in many tissues and cell types and can be separated pharmacologically into two classes (see Table 1). The first and more widely studied of the two are the "central-type" binding sites located in brain which mediate the clinical effects of the benzodiazepines. These "central-type" sites are associated with the neuronal postsynaptic gamma-aminobutyric acid receptor which regulates Cl$^-$ flux (Costa and Guidotti, 1979). Benzodiazepines also bind to another distinct binding site (Braestrup and Squires, 1977; Schoemaker et al., 1981) found in the membranes of many mammalian tissues: heart, kidneys, lungs, adrenals, blood platelets and also the brain, termed the peripheral-type benzodiazepine receptor (PBR).

Apoptotic cell death can be induced by a variety of drugs with diverse chemical structure and different mechanism of action. Among the list of apoptosis inducing agents are a wide range of anti-cancer drugs including camptothecin, etoposide and the anthracycline antibiotics daunorubicin and doxorubicin. Although the mechanism of anti-tumour action of some of these drugs has not been fully elucidated, they ultimately activate the event of apoptosis in cells. All of the above anti-cancer drugs have previously been shown to induce apoptosis in cancerous cells derived from the haemopoietic system such as HL-60 and Jurkat cells. Any novel drugs that can also induce apoptosis in similar model cell lines may have potential as anti-cancer agents. One major problem in cancer chemotherapy is inherent or acquired resistance. Chronic myeloid leukaemia (CML) is associated with drug resistance, and although anti-cancer agents such as hydroxyurea appear to contain the disease during its chronic phase, progression to a fatal blast crisis is inevitable. Resistance to anti-cancer agents in CML has been suggested to be via suppression of apoptosis. It would therefore be useful to develop novel drugs that overcome this apoptosis suppression in CML cell lines.

DESCRIPTION OF THE PRIOR ART

The exact function of the PBR is unclear although PBR specific ligands such as Ro5-4864 (4'-chlorodiazepam) and PK11195 (1-(2-chlorophenyl)-1,3-dihydro-1-methyl-propyl)isoquinoline carboxamide) have been shown to elicit a wide variety of effects including alteration in cardiac action potentials and calcium channels, alterations of protooncogene expression modulation of steroidogenesis and alteration of immune function (Zisterer & Williams, 1997 for review). There have been many reports that benzodiazepines affect cell growth and differentiation in a number of cell types. These include induction of differentiation of Friend erythroleukemia cells (Wang et al., 1984a) and inhibition of cell proliferation (Wang et al., 1984b; Gorman et al., 1989; Ikezaki and Black, 1990; Camins et al., 1995). However, because of the high concentrations of PBR ligands necessary to elicit these antiproliferative effects and the demonstration of similar effects in cell lines which lack the PBR (Gorman et al., 1989), it could be concluded that these antiproliferative effects seem unrelated to a specific interaction of these drugs with this receptor.

Recently a novel series of high affinity PBR ligands based on a pyrrolobenzoxazepine skeleton, classified here as PBOX compounds, have been synthesised (Campiani et al., 1996). A recent study (Zisterer et al., 1998) has demonstrated that three of these novel PBR ligands, PBOX 1, 2 and 21 along with the classically used PBR ligands PK 11195 and Ro5-4864 were found to inhibit at micromolar concentrations and in a dose-dependent manner, the proliferation of rat C6 glioma and human 132 1 N1 astrocytoma, without being cytotoxic. This antiproliferative effect was found to be mediated by arrest in the G1 phase of the cell cycle.

The present inventors have, while examining the effect of PK 11195, Ro5-4864 and some PBOX compounds on the proliferation of the human cancer cell lines, Jurkat (leukaemic T cell lymphoblast), HL-60 (promyelocytic leukaemia) HUT 78 (T cell leukemia), LAMA, KYO.1 and K562 cells which are all CML (chronic myeloid lymphoma) cells, Hela (cervix carcinoma), CEM (T lymphoblastoid) cells and MCF-7 (human breast carcinoma) cells, determined that these PBR ligands induce apoptosis, with various potencies, in the nine cell lines. Apoptosis is a cell suicide mechanism invoked in disparate situations, both physiological and pathological, to ablate unwanted, damaged, or potentially neoplastic cells. Apoptosis is classically defined by a characteristic set of morphological changes in the cell, including membrane blebbing, cell shrinkage, chromatin condensation, DNA fragmentation and eventual formation of membrane-bound apoptotic bodies. Although a number of reports have identified agents that are capable of inducing apoptosis in a variety of cells and tissues, the mechanisms responsible for the activation of the apoptosis process are poorly understood.

BRIEF DESCRIPTION OF THE DRAWINGS

FIG. 1 shows morphological features of HL-60 cells undergoing apoptosis following treatment with PBox-6;

FIG. 2 shows the percentage of apoptosis induced in HL 60 cells by some pyrrolo-1,5benzoxazepines and other PBR ligands;

FIG. 3 shows that PBox-6-induced apoptosis in HL60 cells is dose- and time-dependent and results in DNA fragmentation;

FIG. 4 shows that PBox-6 induces apoptosis through acitvation of caspase 3-like proteases;

FIG. 5 shows the disappearance of pro-caspase 3 in HL-60 cells in response to PBox-6 treatment;

FIG. 6 shows the accumulation of Cytochrome C in response to PBox-6;

FIG. 7 illustrates that N-acetylcysteine or TEMPO pretreatment does not protect HL-60 cells against PBox-6 induced apoptosis;

FIG. 8 shows the induction of apoptosis in Jurkat cells by pyrrolo-1,5-benzoxazepines;

FIG. 9 illustrates the lack of involvement of NFκB in pyrrolobenzoxazepine-induced apoptosis;

FIG. 10 illustrates that PBox-6 induces transient activation of JNK in HL-60 cells;

FIG. 11 shows that PBox-6 induces apoptosis in normal (neo) CEM cells;

FIG. 12 shows that PBox induces apoptosis in Bcl-2 overexpressed CEM cells;

FIG. 13 shows the induction of apoptosis in K562 cells by some pyrrolo-1,5-benzoxazepines and other PBR ligands;

FIG. 14 shows that PBox-6 induced apoptosis in CML cells is time and dose-dependent;

FIG. 15 shows PBox-6 induces internucleosomal DNA fragmentation in CML cells;

FIG. 16 shows the downregulation of BCR-abl in K562 and KYO.1, but not in Lama 84 cells in response to PBox-6 treatment;

FIG. 17 shows the results of Cytochrome C western blotting to analyse the effect of PBox-6 on accumulation of Cytochrome C in the cystol;

FIG. 18 shows Cytochrome C is not all non-specifically released from Mitochondria during sample preparation;

FIG. 19 shows activation of caspase 3 in K562 and Lama 84 but not KYO.1 cells in response to PBox-6 treatment;

FIG. 20 shows that caspase 3 inhibitor, z-DEVD-fmk, fails to protect against PBox-6 induced apoptosis in CML cells;

FIG. 21 shows the induction of PARP cleavage in CML and Hela cells following treatment with PBox-6 and PBox-3;

FIG. 22 shows that antioxidants fail to protect against PBox-6 induced apoptosis in K562 cells;

FIG. 23 shows that PBox-6 alters the tyrosine phosphorylation status of proteins in K562 cells;

FIG. 24 shows that pre-treatment of K562 cells with the tyrosine kinase inhibitor, Genistein, prevents protein tyrosine phosphorylation and inhibits apoptosis induced by PBox-6;

FIG. 25 shows that Herbimycin A and Tyrophostin reduce, but do not completely inhibit, PBox-6 induced apoptosis in K562 cells;

FIG. 26 shows that Etoposide and mitoxanthrone pre-treatment of K562 cells protects against PBox-6 induced apoptosis;

FIG. 27 shows that PBox-6 does not induce DNA strand break in K562 cells;

FIG. 28 shows that pre-treatment of Jurkat cells with ICRF 187 inhibits etoposide induced DNA strand breaks and protects against apoptosis;

FIG. 29 shows that pre-treatment of K562 cells with ICRF 187 reduces the level of apoptosis induced by PBox-6;

FIG. 30 shows that pre-treatment of Jurkat cells with PBox-6 failed to protect against DNA strand breaks or apoptosis induced by etoposide;

FIG. 31 shows PBox-6 induces transient activation of JNK in K562 cells;

FIG. 32 shows PBox-6 induces activation of JNK in KYO.1 and Lama 84 cells;

FIG. 33 shows lack of activation of p38 in K562 cells in response to PBox-6;

FIG. 34 shows lack of activation of p42-44 iin K562 cells in response to PBox-6;

FIG. 35 shows pre-treatment of K562 cells with an inhibitor of Rac 1, lethal toxin, failed to protect against PBox-6 induced JNK activation and apoptosis;

FIG. 36 shows that activation of JNK lies upstream of a requirement for Topo II in the pathway by which PBox-6 induces apoptosis in K562 cells; and FIG. 37 shows PBox-6 induces apoptosis in MCF-7 cells.

SUMMARY OF THE INVENTION

According to the present invention there is provided a pharmaceutical composition comprising an apoptosis-inducing amount of a compound having the general formula (I):

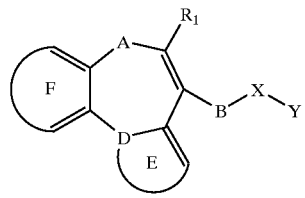

wherein:

(i) $R_1$ represents unsubstituted straight chain $C_1$–$C_{10}$, or branched $C_1$–$C_{10}$ alkyl or unsubstituted $C_3$–$C_{10}$ cycloalkyl; or straight chain or branched $C_{1-10}$ alkyl substituted with one or more of F, Br, Cl, I, $F_3C$, MeO, EtO; or $C_3$–$C_{10}$ cycloalkyl substituted with one or more of F, Br, Cl, I, $F_3C$, MeO, EtO, or unsubstituted straight chain, or branched $C_2$–$C_{10}$ alkenyl or unsubstituted $C_3$–$C_{10}$ cycloalkenyl; or straight chain or branched $C_2$–$C_{10}$ alkenyl substituted with one or more of F, Br, Cl, I, $F_3C$, MeO, EtO; or $C_2$–$C_{10}$ cycloalkenyl substituted with one or more of F, Br, Cl, I, $F_3C$, MeO, EtO;

or an unsubstituted $C_6$–$C_{20}$ aryl group or a $C_6$–$C_{20}$ aryl group substituted with one or more of F, Br, Cl, I, $F_3C$, MeO, EtO, phenyl, phenoxy, $CH_2$ phenyl, naphthyl; and (ii) A represents N, O, S or the group $CH_2$; and (iii) B represents O, or the group $CH_2$; and (iv) D represents N and (v) the cyclic group labelled E is taken together with D to form a pyrrole, imidazole or indole ring or a pyrrole ring substituted with a methyl, chloryl or formyl group preferably at the 2-position;

and the group formed by E and D together is optionally substituted or further substituted by one or more of the substituents F, Br, Cl, I, $F_3C$, MeO, EtO and wherein the cyclic group labelled F represents:

an unsubstituted $C_6$–$C_{20}$ aryl group or a $C_6$–$C_{20}$ aryl group substituted with one or more of F, Br, Cl, I, $F_3C$, MeO, EtO; and wherein (vi) X represents a group C=O, C=S, P=O or $CH_2$; and when X is P=O, $R_2$ and $R_3$ are independently MeO or EtO, (vii) and wherein Y represents the group

wherein $R_2$ and $R_3$ are independently hydrogen; or unsubstituted straight chain $C_1$–$C_{10}$, or branched $C_1$–$C_{10}$ alkyl or unsubstituted $C_3$–$C_{10}$ cycloalkyl, or straight chain or branched $C_1$–$C_{10}$ alkyl substituted with one or more of F, Br, Cl, I, $F_3C$, MeO, EtO; or $C_3$–$C_{10}$ cycloalkyl substituted with one or more of Cl, $N(Me)_2$, Br, $N(C_1$–$C_3$ alkyl$)_n$ where n=1 or 2; or unsubstituted straight chain, or branched $C_2$–$C_{10}$ alkenyl; or unsubstituted $C_3$–$C_{10}$ cycloalkenyl, or straight chain or branched $C_2$–$C_{10}$ alkenyl substituted with one or more Cl, N(Me)$_2$, Br, N(C$_1$–C$_3$ alkyl), where n=1 or 2; or C$_2$–C$_{10}$ cycloalkenyl substituted with one or more Cl, N(Me)$_2$, Br, N(C$_1$–C$_3$)$_n$ where n=1 or 2; or R$_2$ and R$_3$ can be taken together with the nitrogen atom to which they are bonded to form a heterocycle optionally containing one or more other heteroatoms selected from O, N or S and optionally substituted by C$_1$–C$_4$ alkyl, methyl, F, Br, Cl, I, F$_3$C, MeO or EtO; or Y represents the group

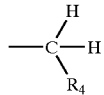

wherein R$_4$ is C$_1$–C$_{13}$ alkyl;

and R$_4$ is optionally substituted with F, Br, Cl, I, F$_3$C, MeO, EtO; or

Y is unsubstituted straight chain C$_1$–C$_{10}$, or branched C$_1$–C$_{10}$ alkyl or unsubstituted C$_3$–C$_{10}$ cycloalkyl, or straight chain or branched C$_1$–C$_{10}$ alkyl substituted with one or more of F, Br, Cl, I, F$_3$C, MeO, EtO; or C$_3$–C$_{10}$ cycloalkyl substituted with one or more of Cl, N(Me)$_2$, Br, N(C$_1$–C$_3$ alkyl)$_n$, where n=1 or 2; or unsubstituted straight chain, or branched C$_2$–C$_{10}$ alkenyl; or unsubstituted C$_3$–C$_{10}$ cycloalkenyl, or straight chain or branched C$_2$–C$_{10}$ alkenyl substituted with one or more Cl, N(Me)$_2$, Br, N(C$_1$–C$_3$alkyl) where n=1 or 2; or C$_2$–C$_{10}$ cycloalkenyl substituted with one or more Cl, N(Me)$_2$, Br, N(C$_1$–C$_3$)n where n=1 or 2.

Suitably R$_1$ is an unsubstituted phenyl group; or phenyl substituted by one or more of F, Br, Cl, I, F$_3$C, MeO, EtO, phenyl, phenoxy, CH$_2$ phenyl; or unsubstituted naphthyl; or naphthyl substituted with one or more of F, Br, Cl, I, F$_3$C, MeO, EtO; and if substituted the naphthyl group preferably being substituted at the 1- or 2-position or at both positions; or an unsubstituted five or six membered heterocyclic group with at least one hetero atom and wherein the, or each heteroatom is selected from N, O or S; or a five or six membered heterocyclic group with at least one heteroatom and wherein the or each heteroatom is selected from N, O, S, the heterocyclic group being substituted with one or more of F, Br, Cl, I, F$_3$C, MeO, EtO and preferably the heterocyclic group being selected from 2- and 3-pyridine, pyrrole, or thiophene.

Suitably F is an unsubstituted phenyl group or phenyl substituted by one or more of F, Br, Cl, I, F$_3$C, MeO, EtO, or unsubstituted naphthyl or naphthyl substituted with one or more of F, Br, Cl, I, F$_3$C, MeO, EtO, or a 5 or 6 membered heterocyclic group, with at least one heteroatom and wherein the or each heteroatom is selected from O, N or S; or a 5 or 6 membered heterocyclic group with at least one heteroatom and wherein the or each heteroatom is selected from O, N or S and which is substituted with one or more C$_1$–C$_4$ alkyl chains F, Br, Cl, I, F$_3$C, MeO, EtO and preferably the heterocyclic group being selected from 2- and 3-pyridine, pyrrole, or thiophene.

Particularly preferred are compounds in which R$_1$ and/or F represent a naphthyl group.

Also preferred are compounds in which R$_1$ represents straight chain or branched C$_2$–C$_{10}$ alkyl, substituted or unsubstituted C$_3$–C$_4$ cycloalkyl, C$_3$–C$_7$ cycloalkyl, C$_5$–C$_7$ cycloalkenyl which may or may not be substituted, substituted or unsubstituted C$_6$–C$_{14}$ aryl. Also preferred are compounds in which the cyclic group F represents a substituted or unsubstituted C$_6$–C$_{14}$ aryl group.

Also preferred are compounds in which Y represents a branched C$_2$–C$_{10}$ alkyl group, a C$_3$–C$_7$ cycloalkyl group, a substituted or unsubstituted C$_5$–C$_7$ cycloalkenyl group.

Preferred aryl groups include biphenyl or phenyl substituted by C$_1$–C$_4$ alkyl, methyl F, Br, Cl, I, F$_3$C, MeO or EtO;

Most preferred compositions are those containing compounds selected from those having the formulae:
PBOX-1, PBOX-2, PBOX-3, (Formerly NF182, 213, 223, respectively), PBOX-4, PBOX-5 (Formerly NF224), PBOX-6, PBOX-7, PBOX-8(Formerly PC3), PBOX-9 (Formerly PC4), PBOX-10, PBOX-11, PBOX-12, PBOX-13, PBOX-14, PBOX-15, PBOX-16, PBOX-17, PBOX-18, PBOX-19, PBOX-20, PBOX-21 (Formerly NF262), PBOX-22, PBOX-23, PBOX-24(Formerly NF212), PBOX-25(Formerly NF267), PBOX-26 (Formerly NF297), PBOX-27(Formerly NF299), PBOX-28, PBOX-29, PBOX-30, PBOX-31 (Formerly NF240), PBOX-32(Formerly NF199), PBOX-33 (Formerly NF149), PBOX-34(Formerly NF181), PBOX-35 (Formerly NF260), PBOX-36(Formerly NF268), PBOX-37(Formerly NF278), PBOX-38(Formerly NF198), PBOX-39(Formerly NF307), PBOX-40(Formerly NF312), PBOX-41 (Formerly NF317), PBOX-42, PBOX-43, PBOX-44, PBOX-45, PBOX-46, PBOX-47, PBOX-48, PBOX-49, PBOX-50, PBOX-51, PBOX-52, PBOX-53(Formerly NF318), PBOX-54(Formerly NF346), PBOX-55(Formerly PC 1), PBOX-56(Formerly PC2), PBOX-57(Formerly PC5), PBOX-58(Formerly PC6), PBOX-59, PBOX-60(Formerly PC11), PBOX-61 (Formerly NF359), PBOX-62(Formerly NF361), PBOX-63(Formerly NF379), PBOX-64 as defined herein.

Particularly preferred are the compositions containing compounds selected PBOX-3, -4, -5, -6, -7, -8, -9, -12, -24, -25, -26, -27, -28, and -30 as defined herein.

The invention also relates to the use of compounds of formula I defined above as an active pharmaceutical substance and also use of these compounds in the preparation of a medicament for the treatment of tumours or other cancerous conditions, as well as the use of the compounds in methods of medical treatment of humans or animals.

The invention also provides novel compounds namely the compounds: PBOX-4, -6, -7, -38, -36, -59, -37, -39, -40, -41, -53, -54, -61, -9, -57, -58, -59, -64, -10, -11, -12, -13, -60, -15, -16, -17, -18, -19, or -20 as defined herein.

The invention also relates to the use of any of the above-defined compounds in the preparation of a medicament for the treatment of tumours or other cancerous conditions, such as CML (chronic myeloid leukaemia), AML, in AIDS-related lymphomas (such as Karpowski's sarcoma, a sub-cutaneous lymphoma) and to their use as apoptotic agents in the treatment of cancers generally.

The invention also provides a method for the synthesis of products with the above mentioned formulae which can be performed following already known methodologies. Starting from the appropriate 2-hydroxyarylamines, the pyrrole or the indole rings are introduced by standard methods. Alkylation of the hydroxy groups with suitable aryl or alkyl acetic acid ethyl esters followed by saponification provides the corresponding acids which are cyclized under Friedel-Crafts conditions. The ketones thus obtained are funnctionalized prior transformation in the corresponding potassium enolates (B=oxygen). On the other hand, for products with B=CH$_2$, the ketones are transformed in the corresponding enol triflates which, after exposure to carbon monoxide, in the presence of Pd (0), and alcohols or amines, leads to esters and amides. Esters are reduced to alcohols, transformed to the corresponding nitrites, and transformed to the (thio)ester or (thio)amides.

DETAILED DESCRIPTION OF THE INVENTION

The methods are described in Campiani et al, 1996a and 1996b. In greater detail the methods are as follows:

Synthesis 1a

The compounds represented by the general formula (I) according to the present invention wherein A is sulfur can be obtained for example starting from pyrrolyl(indolyl)phenyl (heteroaryl)disulfides, in turn prepared by the appropriate precursors by standard procedure. Reductive alkylation by means of sodium borohydride and α-bromoaryl(heteroaryl, alkyl or alkenyl)acetic acid ethyl esters. After hydrolysis to the corresponding acid intermediates, intramolecular cyclization by exposure of the acids to phosphorus pentachloride can provide the thiazepinones. The reaction proceeds in the temperature range of 25 to 85° C. for 12 to 30 hours in anhydrous, polar aprotic solvents. Oxidation with methachloroperbenzoic acid at 0° C. provided the corresponding sulphoxides Treatment of the corresponding potassium enolates (reaction can be performed at 25° C. for 2 to 5 hours) of thiazepinones with selected acyl chlorides and dialkyl or dialkenylcarbamoyl chlorides or mesylchloride can yield the desired compounds. Potassium enolates can be also treated with triphosgene and the resulting acyl chloride can be aminated with different amines. The reaction is generally conducted in tetrahydrofuran at 25° C. for 12 to 48 hours.

Synthesis 1b

The compounds represented by the general formula (I) according to the present invention wherein A is oxygen can be obtained for example starting from 1-(2-hydroxyaryl)pyrroles, 1-(hydroxyheteroaryl)pyrroles or the corresponding indoles by O-alkylation by means of a-bromoaryl (heteroaryl, alkyl or alkenyl)acetic acid ethyl esters. The reaction is conducted generally in the presence of a base such as potassium carbonate in N,N-dimethylformamide as solvent or with sodium hydride in anhydrous tetrahydrofuran at 25 to 50° C. for 10 to 30 hours. After hydrolysis to the corresponding acid intermediates, intramolecular cyclization by exposure of the acids to phosphorus pentachloride, in presence or not of tin(IV) chloride, can provide the oxazepinones. The reaction proceeds in the temperature range of 25 to 85° C. for 12 to 30 hours in anhydrous, polar aprotic solvents. Treatment of the corresponding potassium enolates (reaction can be performed at 25° C. for 2 to 5 hours by means of potassium hydride) of oxazepinones with selected acyl chlorides and dialkyl or dialkenylcarbamnoyl chlorides can yield the desired compounds. Potassium enolates can be also treated with triphosgene and the resulting acyl chloride can be aminated with different amines. The reaction is generally conducted in tetrahydrofuran at 25° C. for 12 to 48 hours.

Synthesis 1c

The compounds represented by the general formula (I) above according to the present invention wherein A is methylene can be obtained for example starting from substituted 2-aminobenzoic esters or corresponding heteroaromatic analogues. After construction of the indole or pyrrole ring by standard procedure by using the amino group, the ester function can be reduced by means of lithium aluminum hydride to the corresponding alcohol (reaction can be performed in anhydrous ethyl ether or tetrahydrofurane at 25 to 40° C. for 1 to 3 hours), which can be oxidized to aldehyde with $MnO_2$ (reaction time 2 to 6 hours). This latter by Wittig reaction performed by using ylides obtained by reacting triphenylphosphine with the appropriate α-bromoaryl (heteroaryl, alkyl or alkenyl)acetic acid ethyl esters, can be transformed to an ester the hydrolysis of which affords the acid intermediate. The Wittig reaction is conducted generally in anhydrous tetrahydrofuran at 25 to 50° C. for 1 to 3 hours while the hydrolysis is conducted at 25° C. for 2 to 5 hours in ethanol/tetrahydrofuran mixture in presence of sodium hydroxide. Phosphorus pentachloride catalyzed cyclization, in presence or not of tin(IV) chloride, provide the azepinones. The reaction proceeds in the temperature range of 25 to 85° C. for 12 to 30 hours in anhydrous, polar aprotic solvents. These latter azepinones can be hydrogenated, and the subsequent treatment of the corresponding potassium enolates (reaction can be performed at 25° C. for 2 to 5 hours by means of potassium hydride) of azepinones with selected acyl chlorides and dialkyl or dialkenylcarbamoyl chlorides yields the desired compounds. Potassium enolates can be also treated with triphosgene and the resulting acyl chloride can be aminated with different amines. The reaction is generally conducted in tetrahydrofuran at 25° C. for 12 to 48 hours.

Synthesis 1d

The compounds represented by the general formula (I) according to the present invention wherein A is nitrogen can be obtained for example starting from pyrrolyl(indolyl)phenyl(heteroaryl)amines, in turn prepared by the appropriate precursors by standard procedure. Transformation of the free amino function to $NHCOCF_3$ (the reaction is conducted generally in presence of trifluoroacetic anhydride in a basic solvent such as pyridine at 25° C. for 2 to 10 hours) followed by insertion of an acyl group in the pyrrole or indole ring by standard Friedel-Crafts reaction using suitable α-bromoacyl chlorides provides α-bromoketone intermediates that can be cyclized and de-protected in the presence of a base such as sodium hydride or potassium carbonate in tetrahydrofuran or N,N-dimethylformamide, or hexamethylphosphoramide obtaining diazepinones. The reaction proceeds in the temperature range of 20 to 100° C. for 1 to 30 hours. Treatment of the corresponding potassium enolates (reaction can be performed at 25° C. for 2 to 5 hours) of diazepinones with selected acyl chlorides and dialkyl or dialkenylcarbamoyl chlorides can yield the desired diazepines. Potassium enolates can be also treated with triphosgene and the resulting acyl chloride can be aminated with different amines. The reaction is generally conducted in tetrahq2ydrofuran at 25° C. for 12 to 48 hours.

Synthesis 2

The heterocyclic compounds represented by the following general formula according to the present invention wherein X is Cl, R' is a 2-propenyl chain, A is oxygen, and Y is a methyl or a dimethylamino group, wherein X is CH, R' is a 1-naphthyl or a 2-naphthyl group, A is sulfur and Y is a methyl or a dimethylamino group, wherein X is CH, A is a $CH_2$, R' is a phenyl or a 1-naphthyl or a 2-naphthyl group, and Y is a methyl or a dimethylamino group, and wherein X is nitrogen, A is oxygen, R' is a phenyl or a 1-naphthyl or a 2-naphthyl group, and Y is a methyl or a dimethylamino group and wherein X is CH, A is oxygen, R' is a phenyl or a 1-naphthyl or a 2-naphthyl group, and Y is a methyl or a dimethylamino group, can be produced by the following methods.

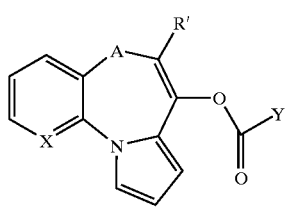
(II)

Synthesis 2a

The compounds wherein X is CH, R' is a 2-propenyl chain, A is oxygen, and Y is a methyl or a dimethylamino group can be obtained by O-alkylation of 1-(2-hydroxyphenyl)pyrrole by means of α-bromo-3-pentenoic acid ethyl ester. The reaction is conducted generally in the presence of a base (sodium hydride) in anhydrous tetrahydrofuran at 25° C. for 15 hours. After hydrolysis of the ester to the corresponding acid intermediate, intramolecular cyclization by exposure of the acid to phosphorus pentachloride, in presence of tin(IV) chloride, can provide the pyrrolobenzoxazepinone. The reaction proceeds at the temperature of 85° C. for 12 hours in anhydrous polar solvent. Treatment of the corresponding potassium enolates (reaction can be performed at 25° C. for 2 hours by means of potassium hydride) of the pyrrolobenzoxazepinone with acetyl chloride or and dimethylcarbamoyl chloride can yield the desired compounds. The reaction is generally conducted in tetrahydrofuran at 25° C. for 12 to 48 hours.

Synthesis 2b

The compounds wherein X is CH, R' is a 1-naphthyl or a 2-naphthyl group, A is sulfur and Y is a methyl or a dimethylamino group can be obtained starting from pyrrolylphenyidisulfide, in turn prepared by the appropriate amine precursor by standard procedure. Reductive alkylation by means of sodium borohydride and α-bromo-2-naphthylacetic acid ethyl esters or α-bromo-1-naphthylacetic acid ethyl esters and subsequent hydrolysis to the corresponding acid intermediate, followed by intramolecular phosphorus pentachloride catalyzed cyclization can provide the pyrrolobenzothiazepinone. The reaction proceeds in the temperature range of 25 to 85° C. for 12 hours in anhydrous, polar aprotic solvent. Treatment of the corresponding potassium enolates (reaction can be performed at 25° C. for 2 hours) of the thiazepinone with acetyl chloride and dimethylcarbamoyl chloride yields the desired compound. The reaction can be conducted in tetrahydrofluran at 25° C. for 30 hours.

Synthesis 2c

The compounds wherein X is CH, A is a CH$_2$, R' is a phenyl or a 1-naphthyl or a 2-naphthyl group, and Y is a methyl or a dimethylamino group can be obtained for example starting from antranilic acid ethyl ester. After construction of the pyrrole ring by a Clauson-Kaas reaction, the ester fuinction can be reduced by means of lithium aluminum hydride to the corresponding benzyl alcohol (reaction can be performed in anhydrous tetrahydrofurane at 25° C. for 3 hours), which can be oxidized to aldehyde with MnO$_2$ (reaction time 6 hours). This latter by Wittig reaction performed by using ylides obtained by reacting triphenylphosphine with α-bromo-α-(aryl)acetic acid ethyl esters, can be transformed to an ester derivative the hydrolysis of which affords the acid intermediate. The Wittig reaction is conducted generally in anhydrous tetrahydrofuran at 25 to 50° C. for 1 to 3 hours while the hydrolysis is conducted at 25° C. for 2 to 5 hours in ethanol/tetrahydrofuran mixture in presence of sodium hydroxide. Phosphorus pentachloride catalyzed cyclization provides the pyrrolobenzoazepinone. The reaction proceeds in the temperature range of 25 to 85° C. for 12 to 30 hours in anhydrous, polar aprotic solvents. After hydrogenation of the double bond (H$_2$ and Pd/C), and the subsequent treatment of the corresponding potassium enolates (reaction can be performed at 25° C. for 2 to 5 hours by means of potassium hydride) with acetyl chloride or dimethylcarbarnoyl chloride yields the desired compounds. The reaction is generally conducted in tetrahydrofuran at 25° C. for 15 hours.

Synthesis 2d

The compounds wherein X is nitrogen, A is oxygen, R is a phenyl or a 1-naphthyl or a 2-naphthyl group, and Y is a methyl or a dimethylamino group can be prepared starting from 3-hydroxy-2-pyrroliypyridine, in turn prepared by a Clauson-Kaas reaction on the corresponding amine. O-alkylation of the pyrrolyl derivative performed with α-bromo-α-(phenyl)acetic acid ethyl ester or with α-bromo-α-(1(2)-naphthyl)acetic acid ethyl ester in presence of sodium hydride in tetrahydrofuran can provide an ester intermediate which can be hydrolysed, and subjected to a phosphorus pentachloride catalyzed cyclization to obtain the key pyrrolopyridooxazepinone. The reaction can be conducted in 1,2-dichloroethane at 25° C. for 15 hours. The reaction of the potassium enolate (reaction can be performed at 25° C. for 2 to 5 hours by means of potassium hydride) of the pyrrolopyridooxazepinone with acetyl chloride or dimethylcarbamoyl chloride can yield the desired compounds. The reaction is generally conducted in tetrahydrofuran at 25° C. for 15 hours.

Synthesis 2e

The compounds wherein X is CH, A is oxygen, R is a phenyl or a 1-naphthyl or a 2-naphthyl group, and Y is a methyl or a dimethyl amino group can be prepared starting from 1-(2-hydroxyphenyl)pyrrole, in turn prepared by a Clauson-Kaas reaction on the corresponding aniline O-alkylation of the pyrrolyl derivative performed with α-bromo-α-phenyl)acetic acid ethyl ester or with α-bromo-(1(2)-naphthyl)acetic acid ethyl ester in presence of sodium hydride in tetrahydrofuran can provide an ester intermediate which can be hydrolysed, and subjected to a phosphorus pentachloride catalyzed cyclization to obtain the key pyrrolopyridooxazepinone. The reaction can be conducted in 1,2-dichloroethane at 25° C. for 15 hours. The reaction of the potassium enolate (reaction can be performed at 25° C. for 2 to 5 hours by means of potassium hydride) of the pyrrolobenzoxazepinone with acetyl chloride or dimethylcarbamoyl chloride can yield the desired compounds. The reaction is generally conducted in tetrahydrofuran at 25° C. for 20 hours.

Synthesis 3

Compounds PBOX-7, -14, -25, -26, -27, -28, -29, -30, -35, -36, -37, -38, -39, -40, -41, -42, -43, -44, -45, -46, -47, -48, -49, -50, -51, -52, -53, -54, -59, -61, -62, -63, and -64 belong to the thiazepine and oxazepine series and are synthesized following synthetic strategies already described above.

Next, specific examples of the derivatives of the present invention are shown. The present invention will be explained in more detail below by way of examples, however is in no way restricted to these examples.

Examples of the pyrido-fused and benzo-fused series:

EXAMPLE 1

1-(3-Hydroxy-2-pyridyl)pyrrole

To a solution of 2-amino-3-hydroxypyridine (7.5 g, 68.1 mmol) in 250 mL of glacial acetic acid, heated at 95–100°

C., was added 2,5-dimethoxytetrahydrofuran (9.0 g, 68.1 mmol) in glacial acetic acid (20 mL). The mixture was stirred for 30 min, the solvent was removed in vacuo, and the residue was extracted with EtOAc. The organic layers were washed with 5% $NaHCO_3$ solution and brine, dried, and evaporated. The crude product was purified by silica-gel column chromatography using dichloromethane/ethyl acetate (8:2) as eluant. Fractions containing the product were combined, dried, and recrystallized by ethyl ether to give analytically pure tide compound (4.7 g) as white prisms: IR (KBr) 2928 $cm^{-1}$; $^1$H NMR ($CD_3OD$) d 6.08 (m, 2 H), 6.96 (dd, 1H, J=7.9, 4.6 Hz), 7.21 (d, 1 H, J=7.9 Hz ), 7.42 (m, 2 H), 7.75 (d, 1H, J=4.6 Hz). Anal. ($C_9H_8N_2O$) C,H,N.

EXAMPLE 2

(±)-a-[3-[2-(1H-Pyrrol-1-yl)pyridyl]oxy] phenylacetic Acid Ethyl Ester

Sodium hydride (347 mg, 14.4 mmol) was added to a solution of 1-(3-hydroxy-2-pyridyl)pyrrole (2.1 g, 13.1 mmol) in anhydrous THF at room temperature. The reaction mixture was stirred for 1 h at room temperature, and then a solution of ethyl α-bromophenylacetate (3.1 g, 13.1 mmol) in anhydrous THF (20 mL) was added dropwise. After 16 h at RT, the solvent was removed in vacuo, and the residue was taken up in dichloromethane. The organic layer was washed with brine, dried and concentrated. The residue was purified by flash chromatography (dichloromethane/hexane 2:1), to give the title compound as a colorless oil: IR (neat) 1748 $cm^{-1}$; $^1$H NMR ($CDCl_3$) d 8.08 (d, 1 H, J=4.8 HZ), 7.82 (m, 2 H), 7.53 (m, 2 H), 7.38–7.41 (m, 3 H), 7.20 (d, 1 H, J=8.1 Hz), 7.02 (dd, 1 H, J=8.1, 4.8 Hz), 6.34 (m, 2 H), 5.63 (s, 1 H), 4.20 (m, 2 H), 1.22 (t, 3 H, J=7.1 Hz). Anal. ($C_{19}H_{18}N_2O_3$) C,H,N.

EXAMPLE 3

(±)-a-[3-[2-(1H-Pyrrol-1-yl)pyridyl]oxy] phenylacetic Acid

The ester (±)-a-[3-[2-(1H-Pyrrol-1-yl)pyridyl]oxy] phenylacetic Acid Ethyl Ester (1.0 g, 31 mmol) was dissolved in 10 mL of EtOH and 5% aqueous NaOH was added. The reaction mixture was stirred at room temperature for 17 h, concentrated, and acidified with 1N HCl. The aqueous phase was extracted with EtOAc, and the organic layer was washed with brine, dried, and concentrated. The residue was recrystallized to give the title compound as colorless prisms: IR (nujol) 1745 $cm^{-1}$; $^1$H NMR ($CDCl_3$) d 8.11 (d, 1 H, J=4.7 Hz), 7.73 (m, 2 H), 7.53 (m, 2 H), 7.40 (m, 3 H), 7.23 (d,1 H, J=8.1 Hz), 7.04 (dd, 1 H, J=8.1, 4.7 Hz), 6.35 (m, 2 H), 5.64 (s, 1 H) Anal. ($C_{17}H_{14}N_2O_3$) C,H,N.

EXAMPLE 4

(±)-6-Phenylpyrrolo[1,2-d]pyrido[3,2-b][1,4] oxazepin-7(6H)-one

Phosphorus pentachloride (0.55 g, 2.3 mmol) was added to a solution of (±)-a-[3-[2-(1H-Pyrrol-1-yl)pyridyl]oxy] phenylacetic Acid (0.64 g, 2.1 mmol) within 20 min. The reaction mixture was stirred at room temperature for 5 h, and then was poured into crushed ice, basified with 10% NaOH solution, and extracted with chloroform. The organic layers were washed with brine, dried and evaporated. The residue was purified by flash chromatography (dichloromethane) and recrystallized (hexane). The title compound was obtained as colorless prisms: IR (nujol): 1741 $cm^{-1}$; $^1$H NMR ($CDCl_3$) d 8.23 (d, 1 H, J=4.7 Hz), 7.59 (m, 1 H), 8.06 (m, 1 H), 7.28–7.36 (m, 6 H), 7.10 (dd, 1 H, J=8.1, 4.7 Hz), 6.54 (m, 1 H), 5.66 (s, 1 H) Anal. ($C_{17}H_{12}N_2O_2$) C,H,N.

EXAMPLE 5

(±)-α-[[2-(1H-Pyrrol-1-yl)phenyl]oxy]-p-tolylacetic Acid Ethyl Ester

Sodium hydride (90 mg, 3.9 mmol) was added to a solution of 1-(2-hydroxyphenyl)pyrrole (0.41 g, 2.5 mmol) in anhydrous THF (5 mL) at RT. The reaction mixture was stirred for 1 h at RT, and then a solution of ethyl α-bromo-p-tolylacetate (1.0 g, 3.9 mmol) in anhydrous THF (5 mL) was added dropwise. After 12 h at RT, the solvent was removed in vacuo, and the residue was taken up in dichloromethane. The organic layers were washed with brine, dried, and evaporated. The residue was purified by chromatography (toluene) to give 0.46 g of the title compound as a colorless oil; IR (neat): 1734 $cm^{-1}$; $^1$H NMR($CDCl_3$) d 1.16 (t, 3 H, J=7.0 Hz), 2.33 (s, 3 H), 4.13 (q, 2 H, J=7.0 Hz), 5.48 (s, 1H), 6.31 (m, 2 H), 6.95–7.40 (m, 10 H).

EXAMPLE 6

(±)-a-[[2-(1H-Pyrrol-1-yl)phenyl]oxy]-p-tolylacetic Acid

The (±)-a-[[2-(1H-Pyrrol-1-yl)phenyl]oxy]-p-tolylacetic Acid Ethyl Ester (0.78 g, 2.3 mmol) was dissolved in 26 mL of EtOH/THF mixture (1:1), and 5% aqueous NaOH (22.4 mL) was slowly added. The reaction mixture was stirred at RT for 3 h, concentrated, and acidified with 4N HCl until pH 3–4. The suspension was extracted with EtOAc and the organic phase was washed with brine, dried, and concentrated. The residue was crystallized to give the acid (0.67 g) as colorless prisms. IR (KBr): 1730 $cm^{-1}$; $^1$H NMR ($CDCl_3$) d 2.32 (s, 3 H), 5.45 (s, 1H), 6.33 (m, 2 H), 6.90–7.35 (m, 10 H).

EXAMPLE 7

(±)-6-p-Tolylpyrrolo[2,1-d][1,5]benzoxazepin-7 (6H)-one

Phosphorus pentachloride (0.4 g, 1.92 mmol) was added to a solution of (±)-a-[[2-(1H-Pyrrol-1-yl)phenyl]oxy]-p-tolylacetic Acid (0.58 g, 1.89 mmol) in dry 1,2-dichloroethane (8.5 mL) within 20 min. The reaction mixture was stirred at RT for 5 h, then was poured into crushed ice, basified with 10% NaOH solution, and extracted with chloroform. The organic layers were washed with brine, dried and evaporated. The residue was chromatographed (dichloromethane and hexane 2:1) and recrystallized to yield 300 mg of the oxazepinone as colorless prisms; IR ($CHCl_3$) 1640 $cm^{-1}$; $^1$H NMR ($CDCl_3$) d 2.31 (s, 3 H), 5.50 (s, 1 H), 6.48 (m, 1 H), 7.0–7.40 (m, 10 H).

EXAMPLE 8

(±)-α-[[2-(1H-Pyrrol-1-yl)phenyl]oxy]-(1-naphthyl) acetic Acid Ethyl Ester

Sodium hydride (90 mg, 3.9 mmol) was added to a solution of 1-(2-hydroxyphenyl)pyrrole (0.4 g, 2.5 mmol) in anhydrous THF (5 mL) at rt. The reaction mixture was stirred for 1 h at rt, and then a solution of ethyl α-bromo-α-(1-naphtyl)acetate (1.0 g, 4.0 mmol) in anhydrous THF (5 mL) was added dropwise. After 12 h at rt, the solvent was removed in vacuo, and the residue was taken up in dichloromethane. The organic layers were washed with brine, dried, and evaporated. The residue was purified by chromatography (toluene) to give 0.46 g of the title compound as a colorless oil; IR (neat): 1734 cm$^{-1}$; $^1$H NMR (CDCl$_3$) δ 1.10 (t, 3 H, J=7.0 Hz), 4.10 (m, 2 H,), 6.15 (s, 1 H), 6.30 (m, 2 H), 6.35–8.25 (m, 13 H).

EXAMPLE 9

(±)-α-[[2-(1H-Pyrrol-1-yl)phenyl]oxy]-(1-naphthyl) acetic Acid

The (±)-α-[[2(1 H-Pyrrol-1-yl)phenyl]oxy]-(1-naphtyl) acetic Acid Ethyl Ester (0.78 g, 2.1 mmol) was dissolved in 26 mL of EtOH/THF mixture (1:1), and 5% aqueous NaOH (22.4 mL) was slowly added. The reaction mixture was stirred at rt for 3 h, concentrated, and acidified with 4N HCl until pH 3–4. The suspension was extracted with EtOAc and the organic phase was washed with brine, dried, and concentrated. The residue was crystallized to give the desired acid (0.67 g) as colorless prisms. IR (KBr): 1730 cm$^{-1}$; $^1$H NMR (CDCl$_3$) δ 5.50 (s, 1 H), 6.10 (s, 1 H), 6.32 (m, 2 H), 6.92–7.15 (m, 4 H), 7.21–7.60 (m, 6 H), 7.84 (m 2 H), 8.15 (m, 1 H).

EXAMPLE 10

(±)-6(1-Naphthyl)pyrrolo[2,1-d][1,5]benzoxazepin-7 (6H)-one

Phosphorus pentachloride (0.4 g, 1.92 mmol) was added to a solution of (±)-α-[[2-(1H-Pyrrol-1-yl)phenyl]oxy]-(1-naphthyl)acetic Acid (0.58 g, 1.68 mmol) in dry 1,2-dichloroethane (8.5 mL) within 20 min. The reaction mixture was stirred at rt for 5 h, then was poured into crushed ice, basified with 10% NaOH solution, and extracted with chloroform. The organic layers were washed with brine, dried and evaporated. The residue was chromatographed (dichloromethane and hexanes 2:1) and recrystallized to yield 300 mg of the oxazepinone as colorless prisms; IR (CHCl$_3$) 1640 cm$^{-1}$; $^1$H NMR (CDCl$_3$) δ 6.27 (s, 1 H), 6.55 (m, 1 H), 6.76 (dd, 1 H, J=9.0 Hz), 6.95 (m, 1 H) 7.09–7.63 (m, 10 H), 8.23 (m, 1 H).

EXAMPLE 11

1-[2-(α-Ethoxycarbonyl-p-methoxybenzyl) thiophenyl]pyrrole

To a solution of sodium (0.46 g, 0.02 g-atom) in 25 mL of anhydrous ethanol, a solution of 1-(2-mercaptophenyl) pyrrole (3.5 g, 0.02 mol) in 8 mL of anhydrous ethanol was added dropwise and the mixture was allowed to stirr for 1 h. After evaporation of the solvent the residue was dissolved in anhydrous tetrahydrofuran (25 mL) and ethyl α-bromo-p-methoxyphenylacetate (5.5 g, 0.02 mol) was slowly added. The reaction mixture was heated at 60° C. for 5 h and then was cooled and poured onto crushed ice, extracted with ethyl acetate. The organic layer was washed with brine, dried and concentrated. The residue was purified by flash chromatography (dichloromethane as eluant) giving 5.05 g (69%) of the desired product. IR (neat) 1735 cm$^{-1}$; $^1$HNMR (CDCl$_3$) δ 1.06 (t, 3 H), 3.76 (s, 3 H), 4.07 (q, 2 H), 4.30 (s, 1 H), 6.35 (t, 2 H), 6.70–7.70 (m, 10 H).

EXAMPLE 12

(±)-α-[[2-(1H-Pyrrol-1-yl)phenyl]thio]-p-methoxyphenylacetic Acid

The (±)-α-[[2-(1H-Pyrrol-1-yl)phenyl]thio]-p-methoxyphenylacetic Acid Ethyl Ester (5.68 g, 15.4 mmol) was dissolved in 35 mL of EtOH/THF mixture (1:1), and 5% aqueous NaOH (40 mL) was slowly added. The reaction mixture was stirred at RT for 3 h, concentrated, and acidified with 4N HCl until pH 3–4. The suspension was extracted with EtOAc and the organic phase was washed with brine, dried, and concentrated. The residue was crystallized to give the acid (4.84 g, 92%) as colorless prisms. IR (KBr): 1710 cm$^{-1}$; $^1$H NMR (CDCl$_3$) d 3.58 (s, 3 H), 4.11 (s, 1 H), 6.11 (m, 2 H), 6.40–7.35 (m, 10 H), 7.67 (s, 1 H).

EXAMPLE 13

(±)-6-p-Methoxyphenylpyrrolo[2,1-d][1,5] benzthiazepin-7(6H)-one

Phosphorus pentachloride (5.48 g, 26.5 mmol) was added to a solution (±)-α-[[2-(1H-pyrrol-1-yl)phenyl]thio]-p-methoxyphenylacetic acid (9.0 g, 26.5 mmol) in dry 1,2-dichloroethane (8.5 mL) within 20 min. The reaction mixture was stirred at RT for 6 h, then was poured into crushed ice, basified with 10% NaOH solution, and extracted with chloroform. The organic layers were washed with brine, dried and evaporated. The residue was chromatographed (dichloromethane as eluant) and recrystallized to yield 3.78 g (44%) of the thiazepinone as colorless prisms; IR (CHCl$_3$) 1638 cm$^{-1}$; $^1$H NMR (CDCl$_3$) δ 3.65 (s, 3 H), 5.10 (s, 1 H), 6.51 (m, 1 H), 6.73 (m, 2 H), 6.91–7.80 (m, 8 H).

EXAMPLE 14

4-Acetoxy-5-phenylnaphto[2,3-b]pyrrolo[1,2-d][1,4] oxazepine (PBOX-3)

To a suspension of potassium hydride (0.035 g, 0.31 mmol, 35% in oil) in anhydrous THF (2.0 mL) was added the ketone (±)-5-phenylnaphto[2,3-b]pyrrolo[1,2-d][1,4] oxazepin-4(5H)-one (0.10 g, 0.31 mmol) dissolved in anhydrous THF (2 mL). The reaction mixture was stirred at rt for 2 h, and then acetyl chloride (22.5 μL, 0.31 mmol) was slowly added. After stirring for 6 h at rt, the solvent was removed in vacuo and the residue was dissolved in chloroform. The organic layer was washed with brine, dried and concentrated. The residue was chromatographed (dichloromethane and hexane 1:4) to give the PBOX-3 in 68% yield. IR (neat) 1765 cm$^{-1}$; $^1$HNMR (CDCl$_3$) δ 2.20 (s, 3 H), 6.46 (m, 1 H), 7.26 (m, 1 H), 7.38–8.20 (m, 12 H).

EXAMPLE 15

7-Acetoxy-6-(1-naphthyl)pyrrolo[2,1-d][1,5] benzoxazepine (PBOX-4)

To a suspension of potassium hydride (0.185 g, 1.65 mmol, 35% in oil) in anhydrous THF (2.0 mL) was added the ketone (±)-6-(1-naphtyl)pyrrolo[2,1-d][1,5] benzoxazepin-7(6H)-one (0.54 g, 1.65 mmol) dissolved in anhydrous THF (2 mL). The reaction mixture was stirred at rt for 2 h, and then acetyl chloride (120 μL, 1.65 mmol) was slowly added. After stirring for 12 h at rt, the solvent was removed in vacuo and the residue was dissolved in EtOAc. The organic layer was washed with brine, dried and concentrated. The residue was chromatographed (dichloromethane and hexane 1:1) to give the PBOX-4 in 73% yield. IR (neat) 1765 cm$^{-1}$; $^1$HNMR (CDCl$_3$) δ 1.83 (s, 3 H), 6.40 (m, 1 H), 6.86(m, 1 H), 7.10–8.11 (m, 12 H).

EXAMPLE 16

4-[(Dimethylcarbamoyl)oxy]-5-phenylnaphto[2,3-b] pyrrolo[1,2-d][1,4]oxazepine (PBOX-5)

To a suspension of potassium hydride (0.102 g, 0.92 mmol, 35% in oil) in anhydrous THF (2.0 mL) was added the ketone (±)-6-(1-naphtyl)pyrrolo[2,1-d][1,5]benzoxazepin-7(6H)-one (300 mg, 0.92 mmol) dissolved in anhydrous THF (2 mL). The reaction mixture was stirred at rt for 2 h, and then dimethylcarbamoyl chloride (68 µL, 0.92 mmol) was slowly added. After stirring for 5 h at 30° C., the solvent was removed in vacuo and the residue was dissolved in EtOAc. The organic layer was washed with brine, dried and concentrated. The residue was chromatographed (dichloromethane and hexane 1:5) to give the PBOX-5 in 53% yield. IR (neat) 1725 cm$^{-1}$; $^1$HNMR (CDCl$_3$) δ 2.92 (s, 3 H), 3.09 (s, 3 H), 6.46 (m, 1 H), 7.25–7.84 (m, 13 H).

EXAMPLE 17

7-((Dimethylcarbamoyl)oxy)-6-(1-naphthyl)pyrrolo [2,1-d][1,5]benzoxazepine (PBOX-6)

To a suspension of potassium hydride (0.030 g, 0.27 mmol, 35% in oil) in anhydrous THF (1.0 mL) was added the ketone (±)-6-(1-naphthyl)pyrrolo[2,1-d][1,5]benzoxazepin-7(6H) one (90 mg, 0.27 mmol) dissolved in anhydrous THF (1 mL). The reaction mixture was stirred at rt for 2 h, and then dimethylcarbamoyl chloride (20 µL, 0.27 mmol) was slowly added. After stirring for 18 h at 30° C., the solvent was removed in vacuo and the residue was dissolved in EtOAc The organic layer was washed with brine, dried and concentrated. The residue was chomatographed (dichloromethane and hexane 1:3) to give the PBOX-6 in 53% yield. IR (neat) 1725 cm$^{-1}$; $^1$HNMR (CDCl$_3$) δ 2.61 (s, 3 H), 2.71 (s, 3 H), 6.41 (m, 1 H), 6.88 (m, 1 H), 7.13–8.16(m, 12 H).

EXAMPLE 18

7-[(Methylcarbamoyl)oxy]-6-(1-naphthyl)pyrrolo[2,1-d][1,5]-benzoxazepine (PBOX-7)

To a suspension of potassium hydride (0.13 g, 1.1 mmol, 35% in oil) in anhydrous THF (1.5 mL) was added the ketone (±)-6-(1-naphthyl)pyrrolo[2,1-d][1,5]benzoxazepin-7(6H)-one (0.36 g, 1.1 mmol) dissolved in anhydrous THF (1 mL). The reaction mixture ft was stirred at rt for 2 h, and then triphosgene (102 mg, 0.34 mmol) was slowly added within 30 min. After stirring for additional 5 min at rt, methylamine (2.2 mmol) and diisopropylethylamine (2.2 mmol) were added and stirring was continued for 10 min. The reaction was quenched with 5% sodium carbonate solution and the mixture was extracted with EtOAc. The organic layer was washed with brine, dried, and concentrated. The residue was chromatographed (dichloromethane and hexanes 1:1) to give PBOX-7 as a colorless oil; IR (CHCl$_3$) 1678$^{-1}$ cm$^1$; $^1$H NMR (CDCl$_3$) δ 2.61 (s, 3 H), 5.71 (br s, 1 H), 6.41 (m, 1 H), 6.88 (m, 1 H), 7.13–8.16 (m, 12 H).

EXAMPLE 19

7-((Dimethylcarbamoyl)oxy)-6-(1-naphthyl)pyrrolo [2,1-d][1,5]benzothiazepine (PBOX-8)

To a suspension of potassium hydride (0.167 g, 1.46 mmol, 35% in oil) in anhydrous THF (4.0 mL) was added the the (±)-6-(1-naphthyl)pyrrolo[2,1-d][1,5]benzothiazepin-7(6H)-one (500 mg, 1.46 mmol) dissolved in anhydrous THF (5 mL). The reaction mixture was stirred at rt for 2 h, and then dimethylcarbamoyl chloride (0.181 g, 1.68 mmol) was slowly added. After stirring for 8 h at 30° C., the solvent was removed in vacuo and the residue was dissolved in EtOAc. The organic layer was washed with brine, dried and concentrated. The residue was chromatographed (dichloromethane) to give the PBOX-8 in 82% yield. IR (neat) 1725 cm$^{-1}$; $^1$HNMR (CDCl$_3$) δ 2.43 (s, 3 H), 2.58 (s, 3 H), 6.45 (m, 1 H), 6.64 (m, 1 H), 7.18–7.57 (m, 10 H), 7.77–7.86 (m, 2 H).

EXAMPLE 20

7-Acetoxy-6-(1-naphthyl)pyrrolo[2,1-d][1,5]benzothiazepine (PBOX-9)

To a suspension of potassium hydride (0.303 g, 2.64 mmol, 35% in oil) in anhydrous THF (5.0 mL) was added the (±)-6-(1-naphthyl)pyrrolo[2,1-d][1,5]benzothiazepin-7 (6H)-one (0.9 g, 2.64 mmol) dissolved in anhydrous THF (7 mL). The reaction mixture was stirred at rt for 2 h, and then acetyl chloride (0.239 g, 3.04 mmol) was slowly added. After stirring for 12 h at rt, the solvent was removed in vacuo and the residue was dissolved in chloroform. The organic layer was washed with brine, dried and concentrated. The residue was chromatographed (dichloromethane and hexane 1:1) to give the PBOX-9 in 86% yield. IR (neat) 1762 cm$^{-1}$; $^1$HNMR (CDCl$_3$) δ 1.70 (s, 3 H) 6.45 (m, 1 H), 6.63 (m, 1 H), 7.19–7.55 (m, 10 H), 7.78–7.87 (m, 2 H).

EXAMPLE 21

7-Acetoxy-6-(1-naphthyl)pyrrolo[1,2-d]pyrido[3,2-b][1,4]oiazepine (PBOX-12)

To a suspension of potassium hydride (0.245 g, 2.14 mmol, 35% in oil) in anhydrous THF (7.0 mL) was added the (±)-6-(1-naphthyl)pyrrolo[1,2-d]pyrido[3,2-b][1,4]oxazepin-7(6H)-one (0.7 g, 2.14 mmol) dissolved in anhydrous THF (7 mL). The reaction mixture was stirred at rt for 2 h, and then acetyl chloride (0.193 g, 2.46 mmol) was slowly added. After stirring for 12 h at rt, the solvent was removed in vacuo and the residue was dissolved in chloroform. The organic layer was washed with brine, dried and concentrated. The residue was chromatographed (dichloromethane and hexane 1:1) to give the PBOX-12 in 75% yield. IR (neat) 1760 cm$^{-1}$; $^1$HNMR (CDCl$_3$)δ 1.83 (s, 3 H), 6.43 (m, 2 H), 7.06–7.21 (m, 2 H), 7.41–7.53 (m, 4 H), 7.77–8.10 (m, 4 H), 8.26 (m, 1 H).

EXAMPLE 22

7-((Dimethylcarbamoyl)oxy)-6-(1-naphthyl)pyrrolo [1,2-d]pyrido[3,2-b][1,4]oxazepine (PBOX-13)

To a suspension of potassium hydride (0.281 g, 2.45 mmol, 35% in oil) in anhydrous THF (5.0 mL) was added the the (±)-6-(1-naphthyl)pyrrolo[1,2-d]pyrido[3,2-b][1,4]oxazepin-7(6H)-one (800 mg, 2.45 mmol) dissolved in anhydrous THF (5 mL). The reaction mixture was stirred at rt for 2 h, and then dimethylcarbamoyl chloride (0.303 g, 2.82 mmol) was slowly added. After stirring for 12 h at 30° C., the solvent was removed in vacuo and the residue was dissolved in EtOAc. The organic layer was washed with brine, dried and concentrated. The residue was chromatographed (dichloromethane and hexane 1:3) to give the PBOX-13 in 78% yield. IR (neat) 1725 cm$^{-1}$; $^1$HNMR (CDCl$_3$) δ 2.61 (s, 3 H), 2.70 (s, 3 H), 6.44 (m, 2 H), 7.10 (m, 2 H), 7.41–7.59 (m, 4 H), 7.62–7.90 (m, 3 H), 8.12 (m, 1 H), 8.25 (m, 1 H).

EXAMPLE 23

7-Hexanoyloxy-6-(1-naphthyl)pyrrolo[2,1-d][1,5]benzoisazepine (PBOX-22)

To a suspension of potassium hydride (0.105 g, 0.92 mmol, 35% in oil) in anhydrous THF (2.0 mL) was added the ketone (±)-6-(1-naphthyl)pyrrolo[2,1-d][1,5] benzoxazepin-7(6H)-one (0.30 g, 0.92 mmol) dissolved in anhydrous THF (2 mL). The reaction mixture was stirred at rt for 2 h, and then hexanoyl chloride (0.143 g, 1.06 mmol) was slowly added. After stirring for 12 h at rt, the solvent was removed in vacuo and the residue was dissolved in EtOAc. The organiuc layer was washed with brine, dried and concentrated. The residue was chromatographed (dichloromethane and hexane 1:1) to give the PBOX-22 in 73% yield. IR (neat) 1765 cm$^{-1}$; $^1$HNMR (CDCl$_3$) δ 0.74 (t, 3 H), 0.92–1.29 (m, 6 H), 2.10 (m, 2 H), 6.44 (m, 2 H), 6.93 (m, 1 H), 7.19 (m, 3 H), 7.88 (m, 2 H), 8.09 (m, 1 H).

EXAMPLE 24

7-((Diethylcarbamoyl)oxy)-6(1-naphthyl)pyrrolo[2,1-d][1,5]benzothiazepine (PBOX-23)

To a suspension of potassium hydride (0.252 g, 2.20 mmol, 35% in oil) in anhydrous THF (5.0 mL) was added the the (±)-6-(1-naphthyl)pyrrolo[2,-d][1,5]benzothiazepin-7(6H)-one (0.75 g, 2.20 mmol) dissolved in anhydrous THF (5 mL). The reaction mixture was stirred at rt for 2 h, and then diethylcarbamoyl chloride (0.343 g, 2.53 mmol) was slowly added. After stirring for 8 h at rt, the solvent was removed in vacuo and the residue was dissolved in EtOAc. The organic layer was washed with brine, dried and concentrated. The residue was chromatographed (dichloromethane) to give the PBOX-23 in 84% yield. IR (neat) 1730 cm$^{-1}$; $^1$HNMR (CDCl$_3$) δ 0.7 (m, 6 H), 2.86 (m, 4 H), 6.45 (m,: 1 H), 6.62 (m, 1 H), 7.19–7.56 (m, 10 H), 7.82 (m, 2 H).

EXAMPLE 25

7-Acetoxy-6p-tolylpyrrolo[2,1-d][1,5]benzoxazepine (PBOX-24)

To a suspension of potassium hydride (0.077 g, 0.69 mmol, 35% in oil) in anhydrous THF (2.0 mL) was added the ketone (±)-6-p-tolylpyrrolo[2,1-d][1,5]benzoxazepin-7(6H)-one (0.20 g, 0.69 mmol) dissolved in anhydrous THF (2 mL). The reaction mixture was stirred at rt for 2 h, and then acetyl chloride (50 μL, 0.65 mmol) was slowly added. After stirring for 12 h at rt, the solvent was removed in vacuo and the residue was dissolved in EtOAc. The organic layer was washed with brine, dried and concentrated. The residue was chromatographed (dichloromethane and hexane 1:5) to give the PBOX-24 in 63% yield. IR (neat) 1760 cm$^{-1}$; $^1$HNMR (CDCl$_3$) δ 2.19 (s, 3 H), 2.37 (s,3 H), 6.38 (m, 1 H), 7.14–7.39 (m, 9 H), 7.65 (m, 1 H).

EXAMPLE 26

7-[(Ethylcarbamoyl)oxy]-6-phenylpyrrolo[2,1-d][1,5]benzoxazepine (PBOX-25)

To a suspension of potassium hydride (0.13 g, 1.1 mmol, 35% in oil) in anhydrous THF (1.5 mL) was added the ketone (±)-6-phenylpyrrolo[2,1-d][1,5]benzoxazepin-7(6H)-one (0.30 g, 1,1 mmol) dissolved in anhydrous THF (1 mL). The reaction mixture was stirred at RT for 2 h, and then triphosgene (330 mg, 1.1 mmol) was slowly added within 30 min. After stirring for additional 5 min at RT, ethylamine (1 mL, 2.1 mmol) and diisopropylethylamine (2.2 mmol) were added and stirring was continued for 10 min. The reaction was quenched with 5% sodium carbonate solution and the mixture was extracted with EtOAc. The organic layer was washed with brine, dried, and concentrated. The residue was chromatographied (dichloromethane and hexane 1:1) to give PBOX-25 as a colorless prisms; mp 74–75° C.; IR (CHCl$_3$) 1697 cm$^{-1}$; $^1$H NMR (CDCl$_3$) d 1.13 (t, 3 H, J=7.35 Hz), 3.22 (q, 2 H, J=6.9 Hz), 5.16 (br s, 1 H), 6.42 (m, 1 H), 7.15–7.78 (m, 11 H).

EXAMPLE 27

7-((Diethylcarbamoyl)oxy)-6-phenylpyrrolo[1,2-d]pyrido[3,2-b][1,4]oxazepine (PBOX-26)

To a suspension of potassium hydride (0.13 g, 1.1 mmol, 35% in oil) in anhydrous THF (1.5 mL) was added the ketone (±)-6-phenylpyrrolo[1,2-d]pyrido[3,2-b][1,4]oxazepin-7(6H)-one (0.3 g, 1.1 mmol) dissolved in anhydrous THF (1 mL). The reaction mixture was stirred at RT for 2 h, and then diethylcarbamoyl chloride (148 mg, 1.1 mmol) was slowly added. After stirring for 12 h at RT, the solvent was removed in vacuo and the residue was taken up in EtOAc. The organic layer was washed with brine, dried, and concentrated. The residue was chromatographed (dichloromethane and hexane 1:1) to give 196 mg of the title compound as a colorless oil; IR(CHCl$_3$) 1765 cm$^{-1}$; $^1$H NMR (CDCl$_3$) d 1.02–1.29 (m, 6 H), 3.27–3.49 (m, 4 H), 6.40 (m, 1 H), 7.06–7.44 (m, 9 H), 7.78 (m, 2H).

EXAMPLE 28

7-[(Methylcarbamoyl)oxy]-6-phenylpyrrolo[2,1]-d[1,5]benzoxazepine (PBOX-27)

To a suspension of potassium hydride (0.11 g, 0.91 mmol, 35% in oil) in anhydrous THF (1.5 mL) was added the ketone (±)-6-phenylpyrrolo[2,1-d][1,5]benzoxazepin-7(6H)-one (0.25 g, 0.91 mmol) dissolved in anhydrous THF (1 mL). The reaction mixture was stirred at RT for 2 h, and then triphosgene (300 mg, 1 mmol) was slowly added within 30 min. After stirring for additional 5 min at RT, ethylamine (1 mL, 2.1 mmol) and diisopropylethylamine (2.2 mmol) were added and stirring was continued for 10 min. The reaction was quenched with 5% sodium carbonate solution and the mixture was extracted with EtOAc. The organic layer was washed with brine, dried, and concentrated. The residue was chromatographed (dichloromethane and hexane 1:1) to give PBOX-27 as a colorless prisms; mp 71–72° C.; IR (CHCl$_3$) 1775 cm$^{-1}$; $^1$H NMR (CDCl$_3$) δ 1.26 (s, 3 H), 6.46 (m, 2 H), 7.11–7.39 (m, 8 H), 7.72 (m, 3 H).

EXAMPLE 29

7-Isonicotinoyloxy-6-p-methoxyphenylpyrrolo[2,1-d][1,5]-benothiazepine (PBOX-28)

To a suspension of potassium hydride (0.124 g, 3.1 mmol, 35% in oil) in anhydrous THF (5.0 mL) was added the ketone (±)-6-(p-methoxyphenyl)pyrrolo[2,1-d][1,5]benzothiazepin-7(6H)-one (1.0 g, 3.1 mmol) dissolved in anhydrous THF (5 mL). The reaction mixture was stirred at rt for 2 h, and then isonicotinoyl chloride hydrochloride (0.55 g, 3.1 mmol) and TEA (0.31 g, 3.1 mmol) in 7 mL of anhydrous tetrahydrofuran was slowly added. After stirring for 12 h at rt, the solvent was removed in vacuo and the residue was dissolved in EtOAc. The organic layer was washed with brine, dried and concentrated. The residue was chromatographed (dichloromethane and hexane 1:1) to give the PBOX-28 in 95% yield (1.25 g). IR (neat) 1738 cm$^{-1}$; $^1$HNMR (CDCl$_3$) δ 3.75 (s, 3 H), 6.40 (m, 1 H), 6.62 (m, 1 H), 6.81 (m, 2 H), 7.1–9.3 (m, 11 H).

EXAMPLE 30

6-p-Methoxyphenyl-7-(3,4,5-trimethoxybenzoyloxy)pyrrolo[2,1-d][1,5]benzothiazepine (PBOX-29)

To a suspension of potassium hydride (0.152 g, 3.8 mmol, 35% in oil) in anhydrous THF (3.0 mL) was added the ketone (±)-6-(p-methoxyphenyl)pyrrolo[2,1-d][1,5] benzothiazepin-7(6H)-one (1.25 g, 3.8 mmol) dissolved in anhydrous THF (5 mL). The reaction mixture was stirred at rt for 2 h, and then 3,4,5-trimethoxybenzoyl chloride (0.88 g, 3.8 mmol) in 7 mL of anhydrous tetrahydrofuran was slowly added. After stirring for 3 h at 85° C., the mixture was cooled and the solvent was removed in vacuo and the residue was dissolved in EtOAc. The organiuc layer was washed with brine, dried and concentrated. The residue was chromatographed (chloroform) to give the PBOX-29 in 54% yield (1.09 g). IR (neat) 1730 cm$^{-1}$; $^1$HNMR (CDCl$_3$) δ 3.76 (s, 3 H), 3.84 (s, 6 H), 3.88 (s, 3 H), 6.39 (m, 1 H), 6.61 (m, 1 H), 6.80 (m, 2 H), 7.15–7.8 (m, 9 H).

EXAMPLE 31

7-(Butyryloxy)-6-(p-methoxyphenyl)pyrrolo[2,1-d][1,5]-benzothiazepine 5-Oxide (PBOX-30)

To a suspension of potassium hydride (0.37 g, 3.26 mmol, 35% in oil) in anhydrous THF (10 mL) was added the ketone (±)-6-(p-methoxyphenyl)pyrrolo[2,1-d][1,5]benzoxazepin-7(6H)-one (1.05 g, 3.26 mmol) dissolved in anhydrous THF (10 mL). The reaction mixture was stirred at rt for 1 h, and then butyryl chloride (0.37 g, 3.48 mmol) was slowly added. After stirring for 2 h at rt, the solvent was removed in vacuo and the residue was dissolved in EtOAc. The organic layer was washed with brine, dried and concentrated. The residue was chromatographed (dichloromethane and hexane 2:1) to give PBOX-30 in 44% yield as colorless prisms: mp 113–115° C., IR (neat) 1759 cm$^{-1}$; $^1$HNMR (CDCl$_3$) δ 0.75 (t, 3 H), 0.92–1.29 (m, H), 1.47 (m, 2 H), 2.17 (t, 2 H), 3.81 (s, 3 H), 6.47 (m, 1 H), 6.64 (m, 1 H), 6.90 (d, 2 H), 7.11 (d, 2 H), 7.22–7.87 (m, 5 H).

EXAMPLE 32

7-[(Ethylcarbamoyl)oxy]-6-p-tolylpyrrolo[2,1-d][1,5]benzoxazepine (PBOX-37)

To a suspension of potassium hydride (0.13 g, 1.1 mmol, 35% in oil) in anhydrous THF (1.5 mL) was added the ketone (±)-6-p-Tolylpyrrolo[2,1-d][1,5]benzoxazepin-7(6H)-one (0.31 g, 1.1 mmol) dissolved in anhydrous THF (1 mL). The reaction mixture was stirred at RT for 2 h, and then triphosgene (102 mg, 0.34 mmol) was slowly added within 30 min. After stirring for additional 5 min at RT, ethylamine (2.2 mmol) and diisopropylethylamine (2.2 mmol) were added and stirring was continued for 10 min. The Ai reaction was quenched with 5% sodium carbonate solution and the mixture was extracted with EtOAc. The organic layer was washed with brine, dried, and concentrated. The residue was chromatographed (dichloromethane and hexane 1:1) to give the title compound as a colorless oil; IR (CHCl$_3$) 1678 cm$^{-1}$; $^1$H NMR (CDCl$_{13}$) d 1.11 (t, 3 H, J=7.1 Hz), 2.36 (s, 3 H), 3.22 (q, 2 H, J=6.9 Hz), 5.06 (br m, 1 H), 6.41 (m, 2 H) 7.18 (m, 6 H), 7.35 (m, 1 H), 7.69 (m, 1 H).

EXAMPLE 33

7-((Dimethylcarbamoyl)oxy)-6-(2-naphthyl)pyrrolo[2,1-d][1,5]benzoxazepine (PBOX-42)

To a suspension of potassium hydride (0.351 g, 3.07 mmol, 35% in oil) in anhydrous THF (10 mL) was added the ketone (±)-6-(2-naphtyl)pyrrolo[2,1-d][1,5]benzoxazepin-7(6H)-one (1.0 mg, 3.07 mmol) dissolved in anhydrous THF (20 mL). The reaction mixture was stirred at rt for 2 h, and then dimethylcarbamoyl chloride (0.380 g, 3.53 mmol) was slowly added. After stirring for 3 h at rt, the solvent was removed in vacuo and the residue was dissolved in EtOAc. The organic layer was washed with brine, dried and concentrated. The residue was chromatographed (dichloromethane) to give the PBOX-42 in 87% yield. IR (neat) 1725 cm$^{-1}$; $^1$HNMR (CDCl$_3$) δ 2.94 (s, 3 H), 3.11 (s, 3 H), 6.43 (m, 2 H), 7.17–7.51 (m, 7 H), 7.84 (m, 4 H), 8.29 (m, 1 H).

EXAMPLE 34

7-((Dimethylcarbamoyl)oxy)-6-(2-naphthyl)pyrrolo[1,2-d]pyrido-[3,2-b][1,4]oxazepine (PBOX-43)

To a suspension of potassium hydride (0.211 g, 1.84 mmol, 35% in oil) in anhydrous TBF (5.0 mL) was added the the (±)-6-(2-naphthyl)pyrrolo[1,2-d]pyrido[3,2-b][1,4]oxazepin-7(6H)-one (600 mg, 1.84 mmol) dissolved in anhydrous THF (5 mL). The reaction mixture was stirred at rt for 2 h, and then dimethylcarbamoyl chloride (0.228 g, 2.12 mmol) was slowly added. After stirring for 12 h at 30° C., the solvent was removed in vacuo and the residue was dissolved in EtOAc. The organic layer was washed with brine, dried and concentrated. The residue was chromatographed (dichloromethane and hexane 1:3) to give the PBOX-43 in 76% yield. IR (neat) 1730 cm$^{-1}$; $^1$HNMR (CDCl$_3$) δ 2.92 (s, 3 H), 3.12 (s, 3 H), 6.44 (m, 2 H), 7.12 (m, 1 H), 7.47–7.55 (m, 3 H), 7.73–7.87 (m, 5 H), 8.24(m, 2H).

EXAMPLE 35

7-Mesyloxy-6-p-methoxyphenylpyrrolo[2,1-d][1,5]benzothiazepine (PBOX-44)

To a suspension of potassium hydride (0.42 g, 10.5 mmol, 35% in oil) in anhydrous THF (3.0 mL) was added the ketone (±)-6-(p-methoxyphenyl)pyrrolo[2,1-d][1,5] benzothiazepin-7(6H)-one (3.4 g, 10.5 mmol) dissolved in anhydrous THF (5 mL). The reaction mixture was stirred at rt for 2 h, and then mesyl chloride (1.2 g, 10.5 mmol) in 7 mL of anhydrous tetrahydrofuran was slowly added. After stirring for 15 h at rt, the solvent was removed in vacuo and the residue was dissolved in EtOAc. The organic layer was washed with brine, dried and concentrated. The residue was chromatographed (chloroform) to give the PBOX-44 in 20% yield (0.85 g). IR (neat) 1357 cm$^{-1}$; $^1$HNMR (CDCl$_3$) δ 2.41 (s, 3 H), 3.82 (s, 3 H), 6.47 (m, 1 H), 6.84 (m, 1 H), 6.91 (m, 2 H), 7.15–7.9(m, 7 H).

Representative compounds included in the present invention are as follows: other suitable compounds are PK11195 (1-(2-chlorophenyl)-1,3-dihydro-1-methyl-propyl) isoquinoline carboxamide) and Ro5-4864 (4'-chlorodiazepam) below:

PK11195
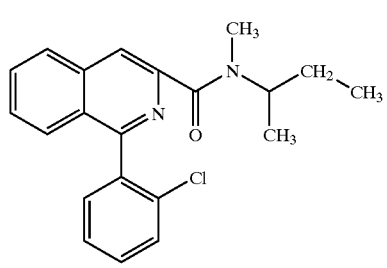
C₂₁H₂₁N₂OCl
MW 352.9
-continued
PBOX-5
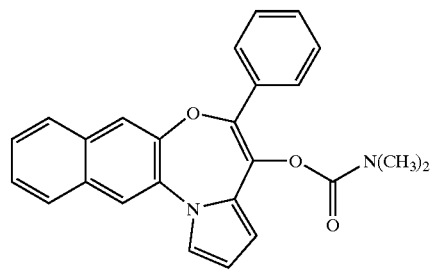
C₂₅H₂₀N₂O₃
396.4
Ro5-4864
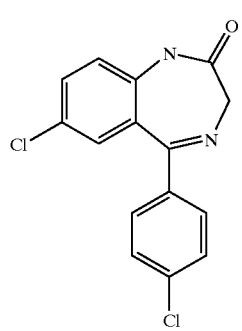
C₁₅H₉N₂OCl₂
MW 304.2
PBOX-6
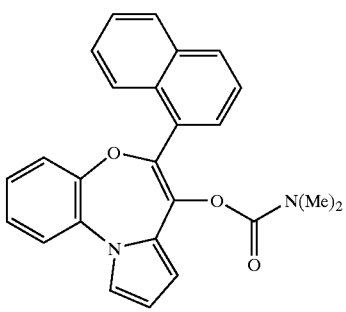
C₂₅H₂₀N₂O₃
396.4
PBOX-3
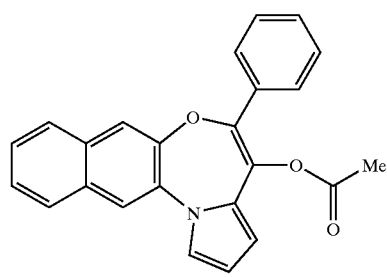
C₂₄H₁₇NO₃
367.4
PBOX-7
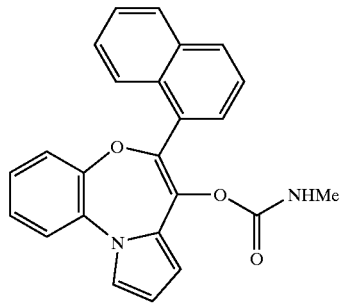
C₂₄H₁₈N₂O₃
382.4
PBOX-4
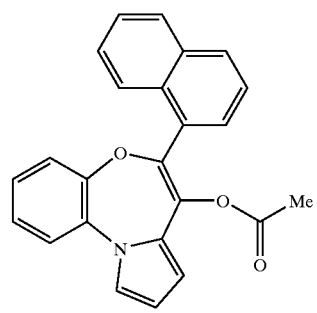
C₂₄H₁₇NO₃
367.4
PBOX-8
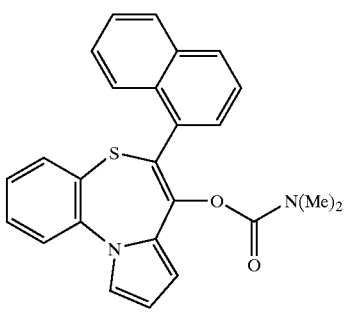
C₂₅H₂₀N₂O₂S
412.5

PBOX-9
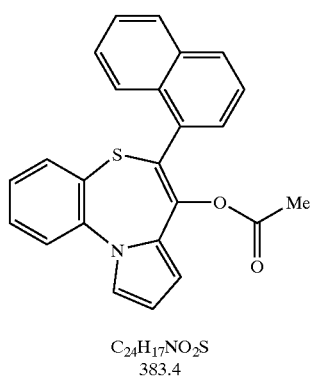
C$_{24}$H$_{17}$NO$_2$S
383.4
PBOX-12
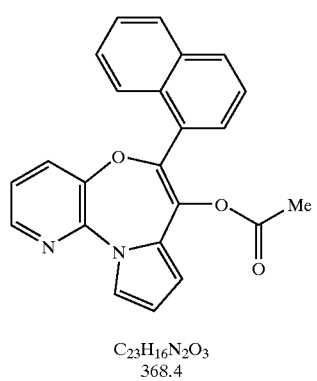
C$_{23}$H$_{16}$N$_2$O$_3$
368.4
PBOX-24
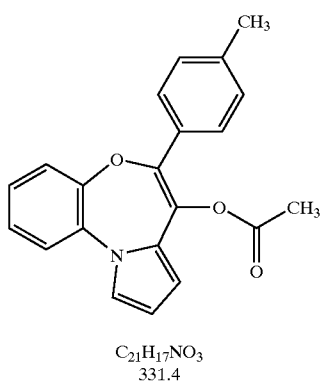
C$_{21}$H$_{17}$NO$_3$
331.4
PBOX-25
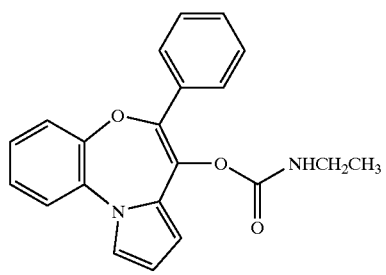
C$_{21}$H$_{18}$N$_2$O$_3$
346.4
PBOX-26
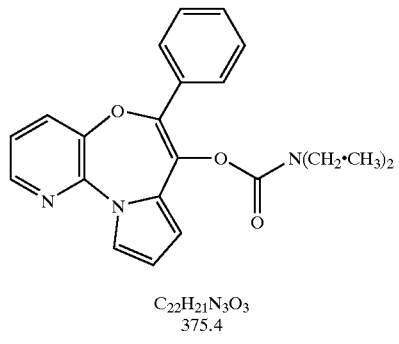
C$_{22}$H$_{21}$N$_3$O$_3$
375.4
PBOX-27
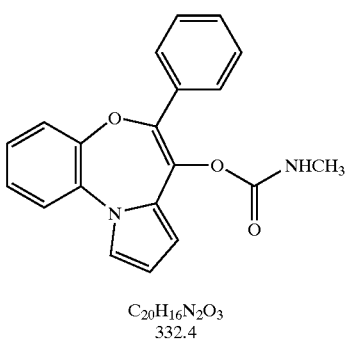
C$_{20}$H$_{16}$N$_2$O$_3$
332.4
PBOX-28
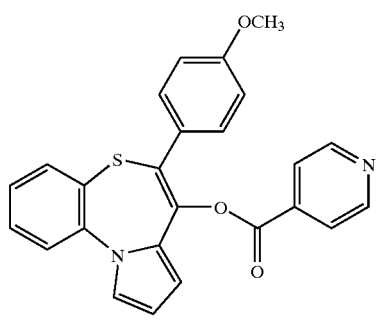
C$_{25}$H$_{18}$N$_2$O$_3$S
426.5
PBOX-30
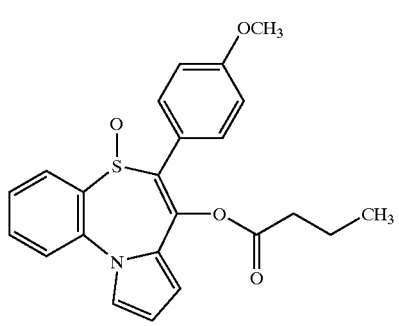
C$_{23}$H$_{21}$NO$_4$S
407.5

PBOX-1
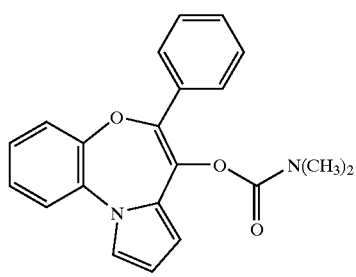
$C_{21}H_{18}N_2O_3$
346.4
PBOX-2
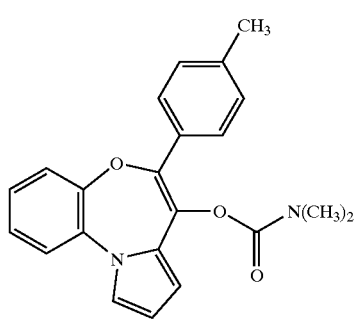
$C_{22}H_{20}N_2O_3$
360.4
PBOX-14
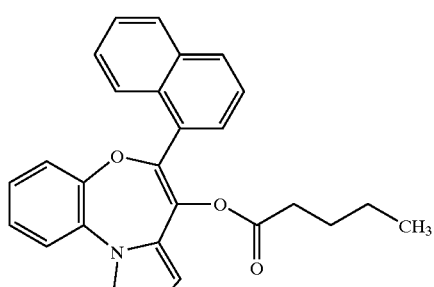
$C_{27}H_{23}NO_3$
409.5
PBOX-31
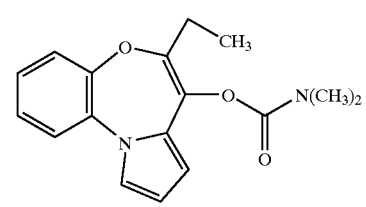
$C_{17}H_{18}N_2O_3$
298.3
PBOX-32
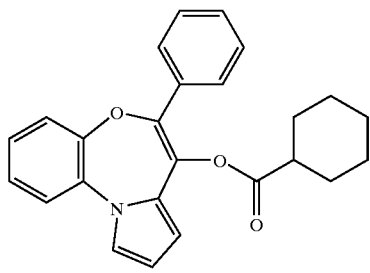
$C_{25}H_{23}NO_3$
385.4
PBOX-33
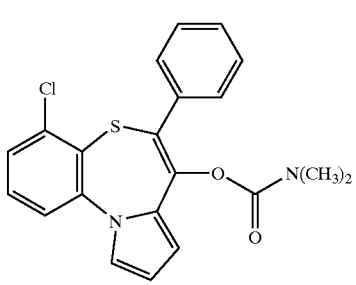
$C_{21}H_{17}ClN_2O_2S$
396.9
PBOX-34
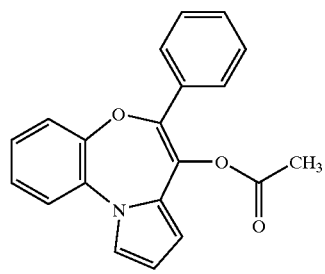
$C_{20}H_{15}NO_3$
317.3
PBOX-35
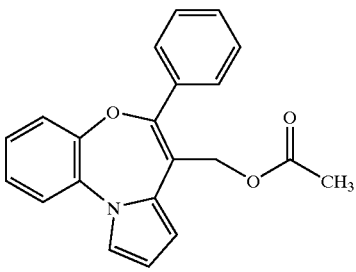
$C_{21}H_{17}NO_3$
331.4

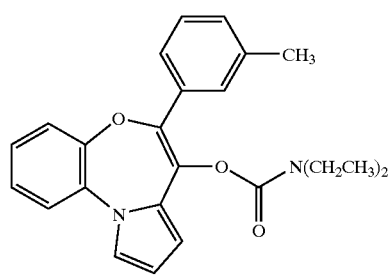
PBOX-36
C₂₄H₂₄N₂O₃
388.5
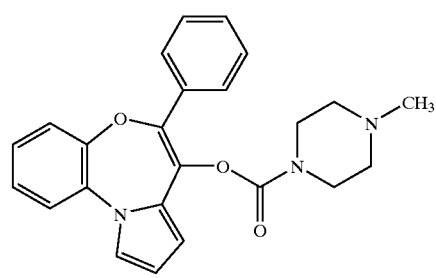
PBOX-39
C₂₄H₂₃N₃O₃
401.5
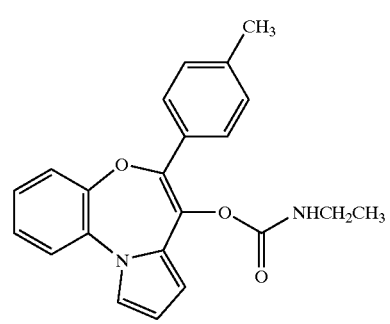
PBOX-37
C₂₂H₂₀N₂O₃
360.4
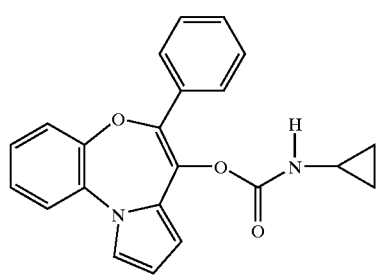
PBOX-40
C₂₂H₁₈N₂O₃
358.4
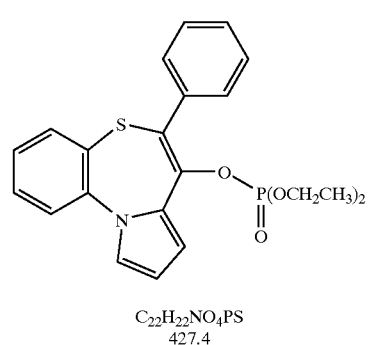
PBOX-38
C₂₂H₂₂NO₄PS
427.4
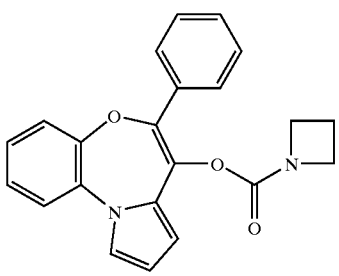
PBOX-41
C₂₂H₁₈N₂O₃
358.4
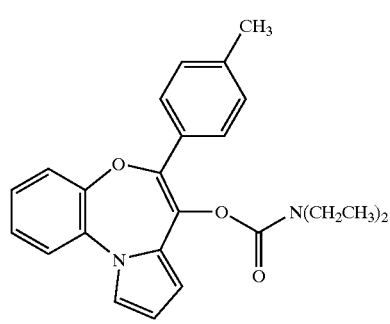
PBOX-21
C₂₄H₂₄N₂O₃
388.5
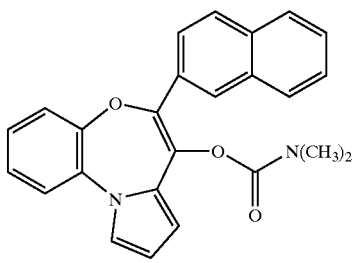
PBOX-42
C₂₆H₂₂N₂O₃
395.5

PBOX-43
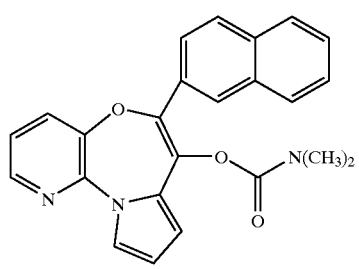
C$_{24}$H$_{19}$N$_3$O$_3$
397.5
PBOX-44
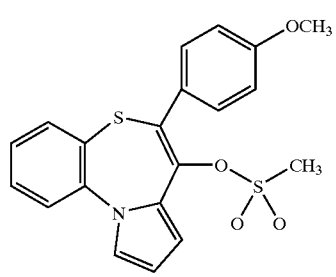
C$_{24}$H$_{19}$N$_3$O$_3$
397.5
PBOX-45
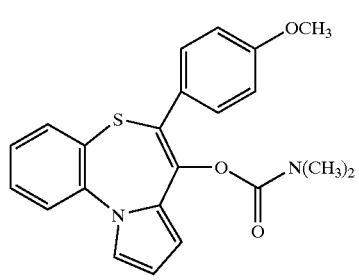
C$_{22}$H$_{20}$N$_2$O$_3$S
332.5
PBOX-29
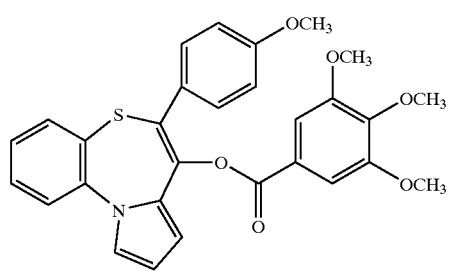
C$_{29}$H$_{25}$NO$_6$S
515.6
PBOX-46
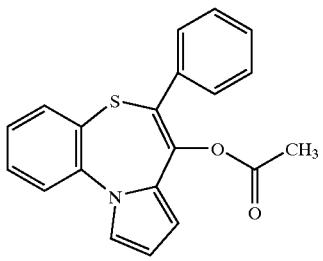
C$_{20}$H$_{15}$NO$_2$S
333.4
PBOX-47
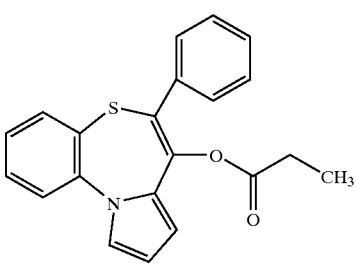
C$_{21}$H$_{17}$NO$_2$S
347.4
PBOX-48
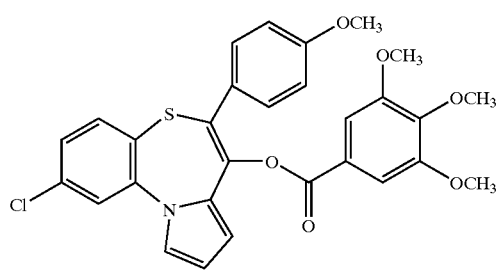
C$_{29}$H$_{24}$ClNO$_6$S
550.0
PBOX-49
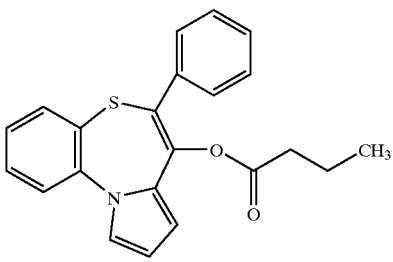
C$_{22}$H$_{19}$NO$_2$S
361.5

PBOX-50
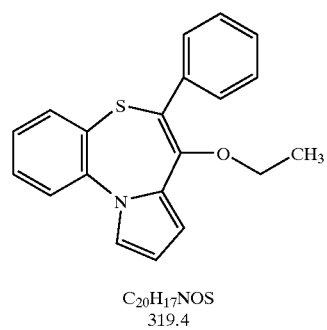
C₂₀H₁₇NOS
319.4
PBOX-51
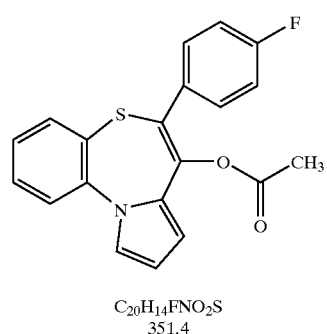
C₂₀H₁₄FNO₂S
351.4
PBOX-52
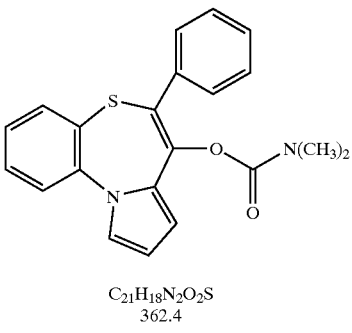
C₂₁H₁₈N₂O₂S
362.4
PBOX-22
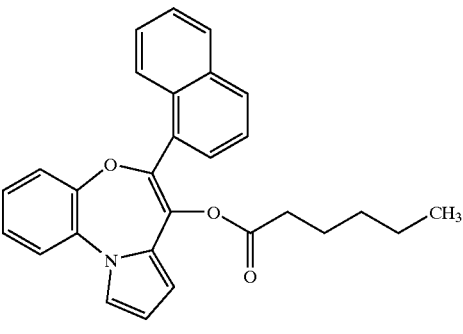
C₂₈H₂₅NO₃
423.5
PBOX-23
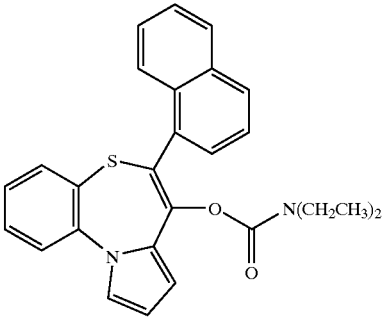
C₂₇H₂₄N₂O₂S
440.5
PBOX-10
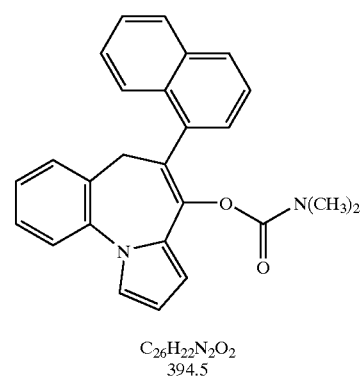
C₂₆H₂₂N₂O₂
394.5
PBOX-11
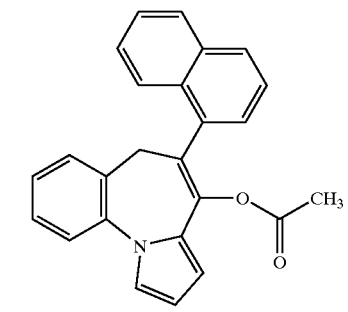
C₂₅H₁₇NO₂
363.4
PBOX-13
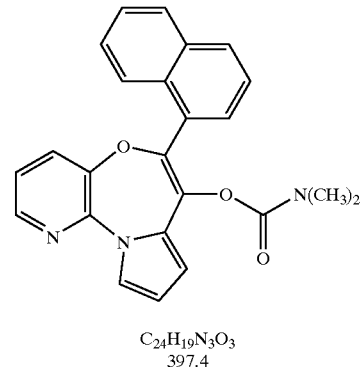
C₂₄H₁₉N₃O₃
397.4

PBOX-15
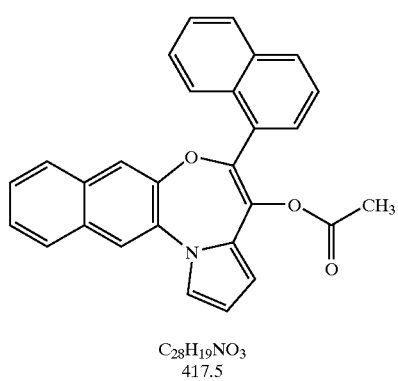
C$_{28}$H$_{19}$NO$_3$
417.5
PBOX-16
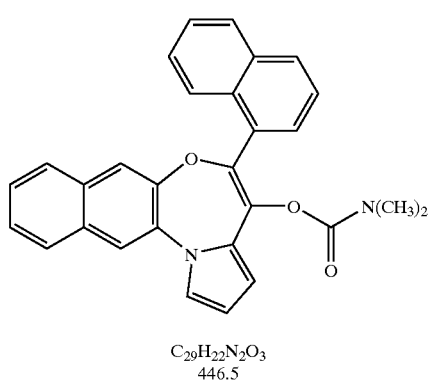
C$_{29}$H$_{22}$N$_2$O$_3$
446.5
PBOX-17
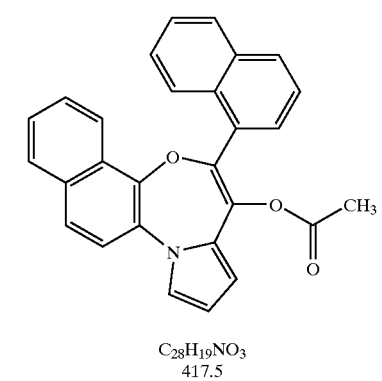
C$_{28}$H$_{19}$NO$_3$
417.5
PBOX-18
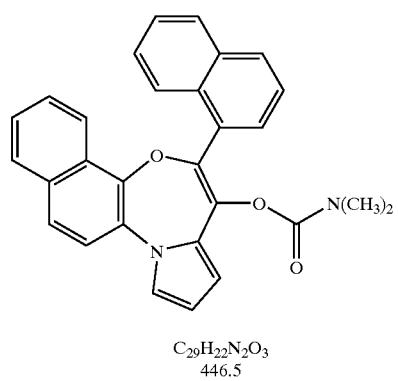
C$_{29}$H$_{22}$N$_2$O$_3$
446.5
PBOX-19
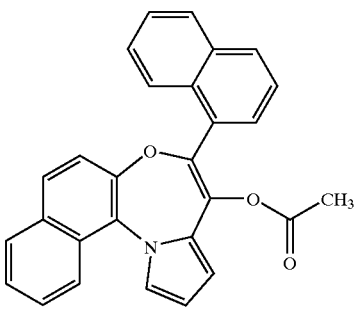
C$_{28}$H$_{19}$NO$_3$
417.5
PBOX-20
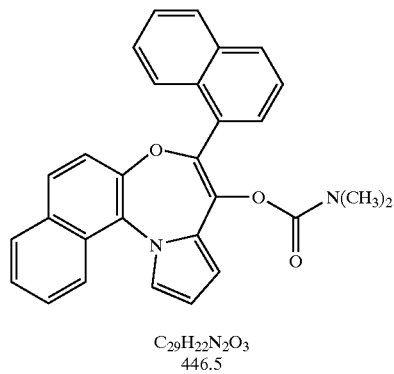
C$_{29}$H$_{22}$N$_2$O$_3$
446.5
PBOX-53
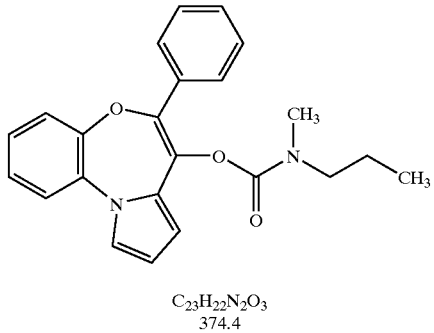
C$_{23}$H$_{22}$N$_2$O$_3$
374.4
PBOX-54
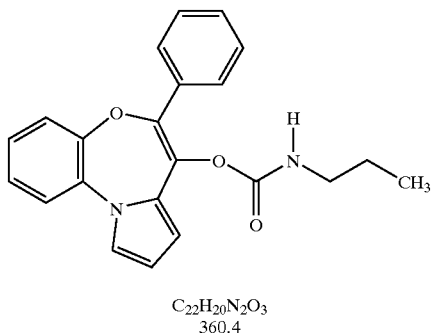
C$_{22}$H$_{20}$N$_2$O$_3$
360.4

PBOX-55
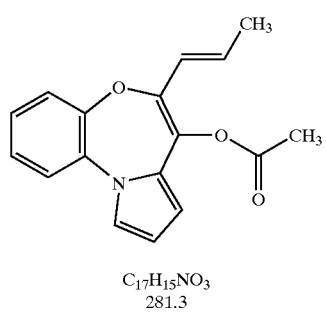
C17H15NO3
281.3
PBOX-59
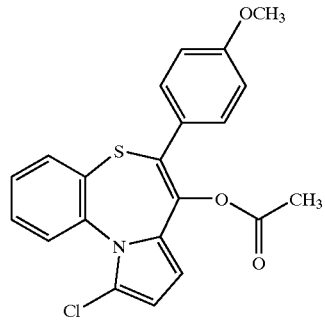
C21H24ClNO3S
397.4
PBOX-56
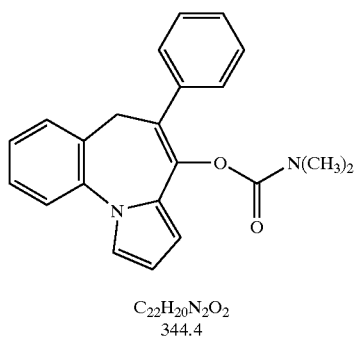
C18H18N2O3
310.3
PBOX-60
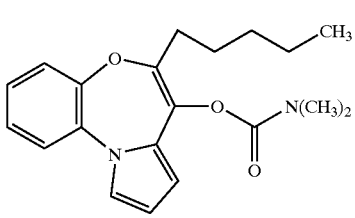
C22H24N2O3
340.4
PBOX-57
C22H20N2O2
344.4
PBOX-61
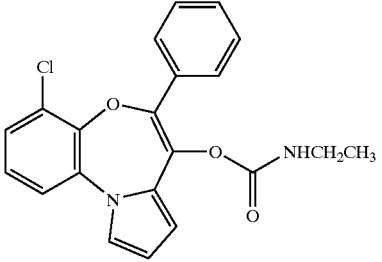
C21H17ClN2O3
380.8
PBOX-58
C21H17NO2
315.4
PBOX-62
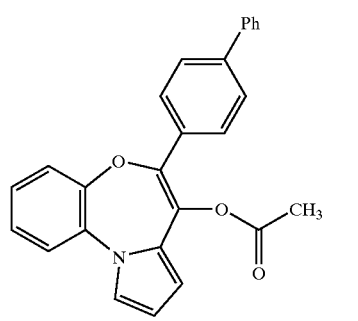
C26H19NO3
393.4

PBOX-63

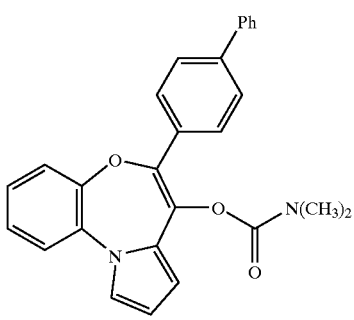

$C_{27}H_{22}N_2O_3$
422.5

PBOX-64

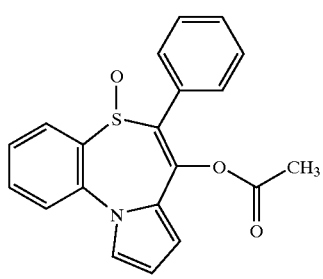

$C_{20}H_{15}NO_3S$
394.4

Materials and Methods
Materials

HL 60 (ECACC No. 881 12501), Jurkat T (ECACC No. 88042803), HUT 78 (ECACC No. 88041901), Hela (ECACC No. 85060701) and MCF-7 (ECACC No. 86012803) cells were obtained from the European Collection of Animal Cell Cultures, Porton Down, Salisbury, U.K. The LAMA 84, KYO.1 and K562 cells were the gift of Dr. Mark Lawlor of St. James' Hospital, Dublin. [$^3$H] PK 11195 (85.8 Ci/mmol) was from Amersham Pharniacia Biotech (Aylesbury, UK). CEM cells, neo and overexpressing Bcl2 were kindly provided by Dr. Seamus Martin, Dept. of Genetics, Trinity College Dublin. The benzodiazepine, Ro 5-4864 [7-chloro-5-(4-chlorophenyl)-1,3-dihydro-1-methyl-2-H-1,4-benzodiazepin-2-one] was obtained from Fluka, Chemie AG, Buchs, Switzerland. PK-11195 [1-(2-chlorophenyl)-N-methyl-N-(1-methylpropyl)-3-isoquinolinecarboxamide] was a gift from Dr. Alan Doble, Pharmuka Laboratories, Gennevilliers, France. The pyrrolobenzoxazepine derivatives (PBOX compounds) were synthesized by Prof. Giuseppe Campiani, University of Siena, Italy. The RapiDiff™ kit was obtained from Diagnostic Developments, Burscough, Lancashire, U.K. The 22 bp oligonucleotide containing the NF kappa B consensus sequence was from Promega (Madison, Wisc., USA). Anti-procaspase 3 was a monoclonal antibody against caspase 3/CPP32β, raised against a 24.7 kDa fragment corresponding to amino acids 1–219 of human caspase 3 and was obtained from Transduction Laboratories (Lexington, Ky., USA). The enhanced chemiluminescence (ECL) kit was from Amersham Corp. (U.K.). All other reagents, including RPMI 1640, fetal calf serum, TNF, staurosporine and the antioxidant compounds, were supplied from Sigma (Poole, Dorset, U.K.). Diazepam and Clonazepam, N-acetyl-cysteine and butylated hydroxyanisole, TNF alpha, PDTC pyrollodithiocarbamate) and TEMPO (TM) were obtained from Sigma (Poole, Dorset, U.K.).Tyrophostin was obtained from Calbiochem-Novabiochem, whereas, genistein, etoposide, herbimycin A, tetrapropylammonium hydroxide and [$^3$H] Thymidine were obtained from Sigma.

Hela cells were obtained from the ECACC. The caspase 3 fluorogenic substrate inhibitor, z-DEVD-fmk, and the anti c-abl antibody was supplied by Calbiochem-Novabiochem (Nottingham, UK). Anti-Cytochrome C was a mouse monoclonal antibody obtained from PharMingen (San Diego, Calif., USA). Anti-PARP antibody was a gift from Mark Dempsey, Dept. of Pharmacology, University College Dublin, Ireland. The anti-p38, anti-p42–44 and anti-JNK phospho and total antibodies were purchased from New England Biolabs. The Topo II inhibitor, ICRF 187, and the lethal toxin were all obtained from Prof L. O'Neill, Biochemistry Dept., Trinity College Dublin.

Cell Culture and Cytospin Analysis of Apoptosis

HL-60 human promyelocytic leukaemia cells were maintained as logarithmically growing cultures in 80% RPMI 1640 medium and 20% heat-inactivated fetal calf serum (FCS) in a humidified incubator with 95% air, 5% $CO_2$ at 37° C. The HUT 78 human T cell lymphoma, the Jurkat human leukaemic T cell lymphoblast cells, the CEM cells, and the three CML cells were grown under the same conditions as above with the exception of the FCS which was at 10%.

HeLa cells were maintained as logarithmically growing cultures in 90% DMEM (Sigma) and 10% FCS in a humidified incubator with 95% air and 5% $CO^2$ at 37° C. These cells adhere to the culture flask and were removed from the surface of the flask by incubation with trypsin (Sigma) (0.025% w/v) in DMEM for approximately 1 min. Growth medium (10 ml) was then added to inhibit the action of trypsin. The cells were reseeded into culture flasks at the appropriate density.

MCF-7 cells were maintained in minimum essential medium supplemented with non-essential amino acids (1% v/v), glutamine (1 mM), FCS (10%) and sub-cultured by the protocol described for Hela cells.

In all experiments performed, cells were seeded at a density of 3×10$^5$ cells/ml into 24-well plates (1 ml well) and immediately treated with the indicated compound. All drugs were diluted from freshly prepared ethanol stock solutions. The final concentration of ethanol in the wells was always 1% (vol/vol); a concentration which by itself had no effect on the cells tested. Following exposure to the appropriate drug, the cells (100 µL) were cytospun onto glass slides pre-coated with poly-L-lysine using a Cytospin 3™ cytocentrifuige (Shandon). They were then stained using the Rapi-Diff kit (eosinm ethylene blue) under the conditions described by the manufacturer. The percent apoptosis and necrosis was determined by counting approximately 300 cells under a light microscope with the aid of a graticule inserted into the eyepiece. At least 3 fields of view per slide, with an average of approximately 100 cells per field, were counted.

Assay for NF Kappa B Binding Activity

Cells were fractionated, and nuclear extracts were prepared as described by Stylianou et al. (1992). Briefly, cells were added to ice-cold phosphate-buffered saline and centrifuged using a swing out rotor at 136×g. They were washed in buffer A (10 mM Hepes, pH 7.9, 1.5 mM $MgCl_2$, 10 mM KCl, 10 mM phenylmethylsulfonyl fluoride [PMSF]) and centrifuged at 10000×g for 10 min. They were treated with buffer A+0.1% (vol/vol) Nonidet P40 on ice for 10 min. They were then centrifuged at 10000×g for 10 min and the pellet was treated with buffer C (20 mM Hepes, pH 7.9, 420 mM NaCl, 1.5 mM $MgCl_2$, 2 mM EDTA, 20% [vol/vol]

glycerol, 0.5 mM PMSF) on ice for 15 min. This material was centrifuged at 10000×g for 10 min and the supernatant was added to 75 u l of buffer D [10 mM Hepes, pH 7.9, 50 mM KCl, 0.2 mM EDTA, 20% (vol/vol) glycerol, 0.5 mM PMSF] per sample. The protein concentration in this crude nuclear extract was determined using the method of Bradford (1976). Protein (4 μg) was incubated with 10000 cpm of a $^{32}$P-labelled oligonucleotide, containing the consensus sequence for NF kappa B, with binding buffer [40% (vol/vol) glycerol, 1 mM EDTA, 10 mM Tris, pH 7.5, 100 mM NaCl, 0.1 mg/ml nuclease free BSA] and 2 μg of poly(dI-dC) at room temperature for 30 min. Samples were resolved on a 5% native polyacrylamide gel which was subsequently dried and autoradiographed at −70° C. overnight.

Assay for Caspase 3 Using Western Blotting

Whole cell extracts from approximately 1×10$^7$ cells were isolated as follows. Cells were centrifuged at 600×g for 5 min and the resulting pellet washed in sterile PBS (1 ml) and transferred into a minifuge tube. The sample was again centriftiged at 600×g for 5 min and the supernatant carefully removed. The pellet was resuspended in 0.2 ml of ice-cold RIPA [PBS, 1% (vol/vol) Nonidet P40, 0.5% (wt/vol) sodium deoxycholate, 0.1% (wt/vol) sodium dodecyl sulphate (SDS), 100 μM PMSF, 3% (vol/vol) aprotinin and 100 μM sodium orthovanadate] and incubated on ice for 30 min. The cells were then homogenised by passage through a 21 G needle (5–7 times) on ice. Following a further incubation on ice for 30 min, the sample was centrifuged in a minifuge at 4° C. for 20 min. Supernatant (150 μl) was removed into fresh minifuge tubes (whole cell lysate) and the protein concentration determined by the method of Bradford (1976). Extracts were frozen at −70° C. until use. The volume of each thawed sample was adjusted with RIPA so that equivalent amounts of protein were present in each sample. Samples were resolved on a 15% polyacrylamide gel containing 0.1% (wt/vol) SDS and immediately transferred onto nitro-cellulose membrane. The membranes were blocked overnight in PBST (PBS containing 0.05% [vol/vol] Tween-20) containing 5% (wt/vol) powdered milk (Marvel), incubated for 1 h with anti-procaspase 3 diluted (1:1000) in 5% (wt/vol) Marvel/TBST and then washed 3 times with PBST for 5 min each. This was followed by the incubation of the membranes in goat anti-mouse horseradish peroxidase-coupled secondary antibody at a dilution of 1:1000 in 5% (wt/vol) MarvelTBST, for 45 min. Enhanced chemiluminescence (ECL) was used to visualise the cross-reacting bands, following a protocol described by the manufacturer.

Measurement of Cytochrome C by Western Blot

Cells (15×10$^6$) were harvested by centrifugation at 1800 g for 10 min at 4° C. After being washed once with ice-cold phosphate-buffered saline, the cell pellet was suspended in 100 μl of ice-cold buffer A (20 mM Hepes, pH 7.5, 10 mM KCl, 1.5 mM MgCl$_2$, 1 mM sodium EDTA, 1 mM sodium EGTA, 1 mM dithiotreitol and 0.1 mM phenylmethylsulfonyl fluoride) supplemented with protease inhibitors (5 μg/ml pepstatin A, 10 μg/ml leupeptin and 2 μg/ml of aprotinin). The cells were left to sit on ice for 15 min and then centrifuged at 20,000 g for 20 min. The resulting supernatant was stored at −70° C. until measurement of cytochrome C. Protein determination was measured by using the Bradford assay. Equal amounts of protein were resolved by SDS-polyacrylamide gel electrophoresis in 15% gels and transferred onto nitro-cellulose. Membranes were blocked with phosphate-buffered saline/5% (w/v) dry milk and probed with anti-cytochrome C antibody. Blots were washed, incubated with goat anti-mouse IgG peroxidase conjugate and developed by ECL according to the manufacturer's recommendations.

Measurement of Protein Tyrosine Phosphorylation by Western Blotting

Jurkat and CML cells (5×10$^6$) were harvested by centrifuigation at 1800 g for 10 min at 4° C. After being washed once with ice-cold phosphate-buffered saline, the cell pellet was suspended in 100 μl of ice-cold lysis buffer (50 mM Tris-HCl, pH 8.0, 150 mM NaCl, 0.1%.SDS, 1% Triton X-100, 1 mM sodium 1 mM phenylmethylsulfonyl, 10 ng/ml leupeptin and 10 ng/ml of aprotinin). The cells were left to sit on ice for 10 min and then centrifuged at 20,000 g for 20 min. The resulting supernatant was stored at −70° C. until measurement of tyrosine phosphorylation. Protein determination was measured by using the Bradford assay. Equal amounts of protein were resolved by SDS-polyacrylamide gel electrophoresis in 15% gels and transferred onto polyvinylidene difluoride (PVDF) membranes. Membranes were blocked with Tris-buffered saline with Tween 20 (10 mM Tris-HCl, pH 8.0, 150 mM NaCl, 0.05% Tween 20) containing 1% w/v BSA and probed with anti-phosphotyrosine antibody. Blots were washed, incubated with goat anti-mouse IgG peroxidase conjugate and developed by ECL according to the manufacturer's recommendations.

Radioligand Binding Assays

HL-60 cells were harvested by centrifugation at 600 g for 5 min and washing in phosphate-buffered saline. The resulting cell pellet was homogenised in 50 mM Tris/HCl buffer, pH 7.4 (2 ml), using an Ultraturrax homogeniser (10 sec) and then passed 5 times through a 21 gauge needle. Cell homogenates (50 μg protein) were incubated with 0.5–50 nM [$^3$H] PK 11195 in 50 mM Tris/HCl buffer, pH 7.4 (incubation buffer), in a total volume of 0.5 ml on ice. Total and non-specific/non-saturable binding in each case was determined in the absence and presence of 10 μM unlabelled PK 11195 respectively. All samples were incubated in triplicate for 60 min. The incubation mixtures were then filtered and counted as previously described (O'Beirne, et al., 1988). When testing the potency of a compound to inhibit [$^3$H] PK 11195 binding, samples were incubated with 2 nM [3H] PK 11195 and various concentrations (0.1 nM to 1 μM) of compound and subsequently treated exactly as above. The resulting Ki values were then generated by the use of the computer programs EBDA and LIGAND.

Caspase 3 Fluorogenic Assay

Cells (5×10$^6$ cells) were harvested by centrifugation, washing in ice-cold phosphate-buffered saline and the pellets resuspended in 200 μl of harvesting buffer (20 mM Hepes, pH 7.5, 10% (w/v) sucrose, 0.1% (w/v) CHAPS, 2 mM dithiotreitol, 0.1% (v/v) Nonidet NP40, 1 mM sodium EDTA and 1 mM phenylmethylsulfonyl fluoride) supplemented with protease inhibitors (1 μg/ml pepstatin A and 1 μg/ml leupeptin). Following incubation on ice for 10 min, samples were passed up and down 10 times through a 21 gauge needle. Following a further incubation on ice for 10 min the homogenates were centrifuged at 20,000 g for 20 min and the resulting supernatants used to measure caspase 3 activity. This enzyme activity was determined by a fluorometric assay using the substrate Ac-DEVD-AMC, which is cleaved by caspase 3 to release the fluorescent leaving group, amino-4-methyl coumarin (AMC). Enzyme extracts (50 μg) were incubated with 100 mM Hepes, pH 7.5, containing 10% (w/v) sucrose, 0.1% (w/v) CHAPS, 10 mM dithiotreitol and 20 μM substrate in a total reaction volume of 3 ml. Following incubation for 60 min at 25° C., fluorescence was monitored continuously using a spectrofluorimeter (excitation wavelength 380 nm, emission wavelength 460 nm). The amount of AMC released was determined by comparison with a standard curve generated with known amounts of AMC.

Agarose Gel Electrophoresis to Detect DNA Ladders

CML cells were seeded at 1×10$^7$ cells in 20 ml of growth medium and treated with ethanol (1% v/v) or PBOX-6 for the required time period at 37° C. Cells were centrifuged at 500 g for 5 minutes and the supernatant removed. The pellet was resuspended in lysis buffer (1 ml) (20 mM EDTA, 100 mM Tris pH 8.0, 0.8% (w/v) sodium lauryl sarcosinate) and incubated at 37° C. for 1 hour. After this incubation, RNAse A was added to each tube (0.5 mg/ml), and left at 37° C. for a further 2–2.5 hrs. Proteinase K (6 mg/ml) was then added to each sample and tubes were incubated overnight at 37° C. 45 μL of each sample was mixed with 5 μl of loading dye and samples were run on a 1.5% agarose gel in TBE for 4 hours at 55V. 10 μl of Ethidium bromide (10 mg/ml) was added into 100 ml agarose. DNA ladders were visible under UV light.

Western Blot Analysis of BCR-abl

Whole cell extracts from approximately 7×10$^6$ cells were isolated as follows. Cells were centrifuged at 500 g for 5 minutes and the resulting pellet washed in 10 mls of PBS. The sample was again centrifuged at 500 g for 5 minutes. The supernatant was removed and the pellet was resuspended in 0.2 ml of harvesting buffer (20 mM Hepes pH 7.5, 10% (w/v) sucrose, 0.1% (w/v) CHAPS, 2 mM DTT, 1 mM EDTA, 1 mM PMSF, 1 μg/ml leupeptin, 1 μg/ml pepstatin) and transferred to a minifuge tube. Samples were incubated on ice for 10 min. The cells were homogenised by passing through a 21 G needle 12 times, and samples were incubated on ice for a further 5 min. Samples were then centrifuged at 20,000 g for 10 min at 4° C. The supernatant was carefully removed to a fresh tube. Protein concentration was determined by the Bradford method. Extracts were frozen at –20° C. until use. The volume of each sample was adjusted with harvesting buffer to obtain equal amounts of protein in each sample. Protein was resolved on an 8% polyacrylaride gel and transferred onto PVDF membrane overnight at 4° C. using wet transfer apparatus. Following transfer, the membrane was blocked for 2 hr at room temperature in PBS containing 5% dry milk. The membrane was then washed 2×2 min in PBST followed by 2 hr incubation at room temperature with anti-c-abl, 1:100 dilution in PBST containing 1% dry milk. The membrane was then washed for 20 min in PBST. Following washing, the membrane was incubated for 1 hr with goat anti mouse horseradish peroxidase coupled secondary antibody at 1:1000 dilution in PBST containing 1% dry milk. ECL was used to visualise cross reacting bands, following the manufacturer's instructions.

Western Blot Analysis of PARP (poly ADP-Ribose polymerase) Cleavage

CML cells were seeded at 2×10$^6$ cells in 5 mls of growth medium, and treated with 10 μM PBOX-6 for 16 and 24 hr. Hela cells were seeded at 1×10$^6$ cells per 25 cm$^2$ flask. Following a 24 hour incubation, the cells were treated with PBOX-3 for a further 48 hours and the cells were scraped up. Cells were then centrifuged at 500 g for 5 min, the supernatant was removed and the pellet was resuspended in 200 μl of PARP sample buffer (62.5 mM Tris/HCl pH 6.8, 6 M urea, 10% (w/v) glycerol, 2% (w/v) SDS, 0.00125% bromophenol blue, and 5% (v/v) β-mercaptoethanol was added immediately before use). Samples were sonicated for 15 sec before aliquoting into 15 μl volumes. Samples were stored at −20° C. until use. 10–15 μl of thawed samples were resolved directly on a 10% polyacrylamide gel and transferred onto PVDF membrane at room temperature using wet transfer apparatus. After transfer, the membrane was blocked overnight in PBS containing 5% dry milk (Marvel). After blocking, the membrane was washed in PBST for 2×2 minutes before incubating for 1 hr with anti-PARP antibody (2 μg/ml in PBST containing 1% dry milk). Following incubation the membrane was washed for 20 minutes in PBST and incubated with goat anti mouse HRP conjugated secondary antibody (1:1000 dilution in PBST containing 1% dry milk). After washing in PBST for 30 minutes, ECL was used to visualise the proteins. The full enzyme is represented by a 119 kDa band while the cleavage products are represented by 29 kDa and 87 kDa bands.

Measurement of DNA Strand Breaks

Alkaline Elution Assay to Measure DNA Strand Breaks

This assay was set up as described by Kohn et al., 1976 with the following modifications.

Cells were seeded at 0.4×10$^6$ cells/ml and were in the logarithmic phase of growth. The doubling time was approximately 16 hours. Cells harvested for the experiments were at a density of 2×10$^6$ cells/ml.

Cells (1×10$^6$) were labelled with [$^3$H] thymidine (sp. act. 2 Ci/mmol) (0.2 μCi/ml) and 1 μM unlabelled thymidine, and incubated for 20 hr. Cells were harvested by centrifugation at 500×g for 5 mins following by two washes in PBS and the pellet was resuspended in 3 ml of PBS. Cells were aliquoted into 1 ml amounts in a 24 well plate and allowed to recover for 1 hr at 37° C. before treating with indicated compounds. Following treatment, cells were washed once in PBS and resuspended in 250 μl of PBS. An aliquot of cells (200 μl) was loaded directly onto a 25 mm diameter glass fiber filter, pore size of 0.2 μM. The cells were lysed on the filter by the addition of 5 ml lysis buffer (2% (w/v) SDS, 10 mM disodium EDTA (pH 10) supplemented with 0.5 mg/ml proteinase K. The lysis buffer was allowed to flow slowly through the filter without suction. Filters were washed using 3 ml wash solution (0.02M Na$_3$EDTA pH 10) allowing it to flow without suction. Filters were eluted in the dark with an alkaline solution (0.04M EDTA plus tetrapropylammonium hydroxide (10% in H$_2$O ) added in the amount required to give pH 12.1). The elution apparatus consisted of a filter funnel with output tubing passing through a peristaltic pump to a collector. Elution took place overnight at a flow rate of 0.05 ml/min. Following elution, filters were treated with 0.4 ml HCl (1N) for 1 hr at 70° C. followed by 2.5 ml NaOH (0.4N) for 30 min at room temp. Scintillation fluid (10 ml) was added and radioactivity remaining on the filters was determined by scintillation counting.

Liquid Scintillation Counting

The [$^3$H] radioactivity was measured using either a Packard Tricarb 300 or a Packard 1500 scintillation counter. The scintillant cocktail used was the commercial scintillant Ecoscint. The average counting efficiency for [3H] counting in the Packard Tricarb 300 was calculated to be 45%, based on a quench-correction curve relating counting efficiency to channels ratio. The same counting efficiency was achieved in the 1500 model scintillation counter and this was calculated from a quench curve relating counting efficiency to the spectral index of the external standard.

Western Blot to Detect Activation of MAPK's

Cells (6×10$^6$) were harvested by centrifugation at 500×g for 5 min and pellets were washed with ice cold phosphate buffered saline containing sodium orthovanadate (Na$_3$VO$_4$) (1 mM). The pellets were resuspended in ice cold lysis buffer (150 mM NaCl, 50 mM Tris/Cl pH 8.0, 0.1% (w/v) SDS, 1% (w/v) Triton X100, 1 mM sodium orthovanadate, 1 μg/ml leupeptin, 1 mM phenylmethylsulfonyl fluoride and 10 μg/ml aprotinin). Samples were incubated on ice for 20 min followed by centrifugation at 20,000×g for 10 min at 4° C.

The resultant supernatants were removed, stored at −70° C. until use and used to measure activation of phosphorylated form of either JNK, p38 or p42–44. A Bradford assay was used to determine protein concentration, and equal amounts of protein was resolved on a 10% SDS-polyacrylamide gel. Proteins were transferred onto PVDF membrane, and blocked overnight with Tris buffered saline (10 mM Tris/Cl pH8.0, 150 mM NaCl) (TBS) containing 5% (w/v) fatty acid free BSA. Membranes were washed with TBS for 5 mins and probed with either anti-JNK phospho, anti-p38 phospho, or anti-p42–44 phospho antibodies, diluted 1:1000 in TBS containing 0.5% Tween 20 (TBST) and 5% (w/v) BSA. Membranes were washed in TBST for 30 min and incubated with goat anti-rabbit horseradish peroxidase coupled secondary antibody, diluted 1:2000 in TBST containing 5% (w/v) BSA. Membranes were washed for 1 hour and ECL was used to visualise cross-reacting bands. Membranes which were probed with anti-JNK phospho were subsequently stripped by incubating for 30 min at 50° C. in a stripping buffer (62.5 mM Tris pH 7.8, 100 nM β-mercaptoethanol and 2% SDS (w/v)). Membranes were then blocked for 1 hour and incubated with anti-JNK total antibody as a loading control.

Bone Marrow Colony Assay

Bone Marrow samples from donor patients were suspended in RPMI and heparin. Approximately 5 mls of Lympoprep was poured into a sterilin and the bone marrow sample was gently layered on top. The sample was centrifuged at 1800 g for 25 min, brake at 2. Following centrifugation, the buffy coat layer which contained the mononucleur fraction was gently removed using a sterile pasteur pipette and was transferred to a fresh tube. Approximately 10 mls of RPMI was added and the sample was centrifuged at 1800 g for 10 minutes, brake at 9. The supernatant was removed and the wash repeated. The pellet was resuspended in approximately 2 mls of RPMI. 20 $\mu$l was removed from the sample, mixed with 380 $\mu$l of ethidium bromide/acridine orange mix.(each at 100 $\mu$g/ml in PBS, 1:1 v/v). Ethidium bromide and acridine orange are fluorescent dyes which bind DNA. Acridine orange intercalates into DNA giving it a green appearance. Ethidium bromide is taken up by non-viable cells only. This dye also intercalates into the DNA, making it appear orange. The cells were counted under a fluorescent microscope and the volume of cells was adjusted to obtain 4×10$^6$ cells per ml. Cells were divided into 2 flasks and treated with 0.5% (v/v) ethanol or 10 $\mu$M PBOX-6. 100 $\mu$l was taken from each flask and added to 1.9 mls of culture media (0.58 ml methylcellulose, 0.55 ml FCS, 0.18 ml BSA, 0.21 ml RPMI, 5 U/ml of granulocytoe monocyte-colony stimulating factor (GM-CSF) and 20 U/ml of erythropoietin (EPO). Tubes were mixed by vortexing and allowed to stand for 1 min before adding 0.5 ml into each of three wells of a 4 well dish. 0.5 ml of sterile water was added to the fourth well. Plates were incubated at 37° C. for 14 days. After 14 days, colonies were scored. A colony is scored as a cluster containing >40 cells, which originates form one stem cell.

Results

A number of pyrrolobenzoxazepines tested were found to induce apoptosis in HL-60 cells (see Table 2 for a summary of apoptosis). The characteristic morphological effects of apoptosis i.e. shrinkage of cells, extensive membrane blebbing, condensation of chromatin and DNA fragmentation, were observed in these cells (FIG. 1). In order to make a direct comparison of potencies, all the PBR ligands were tested in the same experiment at a single concentration (10 $\mu$M). Of the PBOX compounds tested PBOX-3 (formerly NF223), PBOX-4 (formerly NF221), PBOX-5 (formerly NF224), PBOX-6 and PBOX-7 were found to be the most potent apoptotic inducers (FIG. 2A). After treatment of HL-60 cells for 16 hours with a final concentration of 10 $\mu$M of these drugs, the cells exhibited between 25 and 40% apoptosis. The degree of necrosis observed under the same conditions was negligible. At the same time other members of the PBOX series such as PBOX-1 and 2 elicited no effect on cell viability even at the highest concentration tested (5 mM, limits of solubility). Some of the more widely known PBR ligands, PK 11195 and Ro5-4864 also induced apoptosis in HL 60 cells, albeit at a higher concentration 10 $\mu$M (FIG. 2B). These compounds did not induce apoptosis at a concentration of 10 $\mu$M (FIG. 2B). Many of the subsequent experiments were performed using PBOX-6 as a representative "model" apoptotic pyrrolo-1,5-benzoxazepine.

PBOX-6 caused a dose-(FIG. 3A) and time-dependent (FIG. 3B) induction of apoptosis in HL-60 cells. The morphological signs of apoptosis became apparent at 6 hours and increased linearly up to 16 hours. Apoptosis was negligible below a final concentration of 5 $\mu$M of the drug. PBOX-6-induced apoptosis also resulted in DNA fragmentation. When the DNA from HL-60 cells incubated with PBOX-6 for 24 hours was analysed by agarose gel electrophoresis it generated a characteristic "ladder pattern" of discontinuous DNA fragments (FIG. 3C).

Several studies have demonstrated activation of caspases in different pathways of apoptosis (Polverino and Patterson, 1997). To directly address the involvement of caspase 3-like proteases in PBOX-6-mediated apoptosis, we studied caspase 3-like activity in HL60 cells following PBOX-6 treatment. Cytosolic extracts from HL-60 cells treated with PBOX-6 were incubated with the fluorogenic caspase 3-like substrate DEVD-AMC. As shown in FIG. 4A, treatment of cells with PBOX-6 caused a dose-dependent activation of caspase 3-like proteases. This protease activity became evident at 6 hours and increased linearly up to 16 hours (FIG. 4B). This dose-dependent and time-dependent activation of caspase 3-like proteases directly parallels the observed morphological effects of apoptosis induced by PBOX-6, as determined from cytospinning and staining of cells. This result was confirmed by Western blotting, demonstrating that PBOX-6 induces, in a dose-dependent manner, the processing of pro-caspase 3, as monitored by the disappearance of the 32 kDa form of the enzyme (FIG. 5), and this correlates with the appearance of the morphological signs of apoptosis. Caspases are specifically inhibited in vitro and in vivo by cell-permeable tetrapeptides designed to mimic cleavage sites of their respective substrates (Nicholson et al., 1995). Pre-treatment of HL-60 cells for 1 hour with a caspase 3-like protease inhibitor, z-DEVD-fmk, followed by treatment for a further 8 hours with PBOX-6, inhibited both the activity of caspase 3-like proteases (FIG. 4C), and the appearance of the morphological signs of apoptosis (FIG. 4D). This would suggest that activity of caspase 3-like proteases is an essential part of the mechanism by which PBOX-6 induces apoptosis in HL-60 cells.

Previous studies have shown that accumulation of Cytochrome C in the cytosol occurs in response to multiple apoptotic stimuli and that this released Cytochrome C in turn activates caspase 3, thus playing an important part in inducing apoptosis (Kluck et al., 1997). The effect of PBOX-6 treatment of HL-60 cells on accumulation of Cytochrome C in the cytosol was analysed. Treatment of HL-60 cells with PBOX-6 under conditions of induction of apoptosis (FIG. 6) caused an accumulation of Cytochrome C in the cytosol, suggesting that its release may be important in the mechanism by which PBOX-6 induces apoptosis.

Several observations suggest an involvement of reactive oxygen intermediates (ROI) in the signal transduction pathways leading to apoptosis, and that they lie upstream of Cytochrome C release and caspase 3 activation. (Jacobson, 1996). In order to determine whether the induction of apoptosis in HL-60 cells by PBOX-6 involved the production of ROI, these cells were pre-treated with either a commonly used antioxidant N-acetylcysteine (5 mM) or the free radical scavenger, TEMPO (1 $\mu$M), for 30 min prior to incubation with PBOX-6 for a further 8 hours (FIG. 7). Both NAC and TEMPO, at the concentrations utilised, have previously been shown to prevent the formation of ROI in HL-60 cells (Kakeya et al., 1998). Neither of these compounds were found to protect against PBOX-6 induced apoptosis, suggesting that the mechanism by which this compound causes apoptosis in HL-60 cells does not involve the production of ROI.

During apoptosis, Cytochrome C has been reported to exit the mitochondria through the mitochondrial porin channel (also called the voltage-dependent anion channel or VDAC) (Shimizu et al., 1999). As VDAC is associated with the PBR in the mitochondrial outer membrane (McEnery et al., 1992), and as all these PBOX-compounds can bind with high affinity to the PBR we examined whether this receptor was involved in the mechanism by which these compounds cause apoptosis. HL-60 cell homogenates displayed saturable, high affinity binding of [$^3$H] PK 11195, a selective ligand for the PBR, yielding Kd and Bmax values of 17.7±5.0 nM and 9.5±1.5 pmol/mg of protein, respectively. All of the PBOX compounds tested were shown to inhibit [$^3$H] PK 11195 binding to HL-60 homogenates with Ki values between 1–7 nM (table 3), yet micromolar concentrations of these compounds were required to induce apoptosis. All the ligands totally inhibit [$^3$H]PK 11195 binding at high concentrations showing them to be fully competitive inhibitors. In addition, although PBOX-1 and PBOX-2 bind to the PBR with Ki values in the nM range, these drugs did not induce apoptosis. Furthermore, the effect of PBOX compounds on a human T Jurkat cell line was examined, a cell line previously shown to the lack the PBR (Carayon el at, 1996), an observation confirmed by us by ligand binding studies (results not shown). FIG. 8 shows that apoptosis is induced in Jurkat cells treated with PBOX compounds, with similar potency to that observed in treated HL-60 cells. These results suggest that the mechanism by which these PBOX compounds induce apoptosis does not involve their interaction with the peripheral-type benzodiazepine receptor.

NFκB activation has been implicated in induction of resistance of tumour cells to apoptosis (Giri and Aggarwal, 1998). Pre-treatment of HL60 cells with TNF for 30 min, at a concentration which activated NFκB but did not induce apoptosis, followed by treatment with PBOX-6 for 16 hours, afforded no protection against PBOX-6-induced apoptosis (FIG. 9A). We then examined a human Sezary lymphoma cell line, Hut-78, which constitutively expresses NFκB, and as such reportedly causes these cells to be resistant to apoptosis (Giri and Aggarwal, 1998). The five PBOX drugs tested induced apoptosis in Hut-78 cells with similar potency to that observed in HL-60 cells (FIG. 9B). In addition, PBOX-6 had no effect on NFκB in these cells (FIG. 9D). These results would imply that activation of NFκB does not necessarily cause resistance to apoptosis by all apoptotic inducing drugs.

The activation of the transcription factor, NFκB, is initiated by a wide variety of stress stimuli such as ceramide and H$_2$O$_2$, which themselves cause apoptosis (Baeuerle and Henkel, 1994). We tested whether PBOX-6 itself could affect NFκB expression in HL-60 cells. We used TNF treatment as a positive control for activation of NFκB in these cells. Although TNF, in agreement with other reports, was shown to activate NFκB in HL-60 cells, as was demonstrated by the detection of protein-DNA complexes in nuclear extracts, PBOX-6 failed to affect NFκB expression (FIG. 9C). These results would suggest that PBOX-6 induced apoptosis employs an NFκB-independent mechanism.

The mitogen activated protein kinase family (MAPK's), which includes JNK have previously been shown to be activated during signal transduction in many cells in response to various forms of stress and has recently been implicated in apoptosis (Denhardt, 1996). In order to determine the effect of PBOX-6 on the activation of JNK, a Western blot assay was developed. Irradiation of HL-60 cells with UV light has previously been shown to activate JNK and was thus used as a positive control in this assay. HL-60 cells were treated with vehicle or PBOX-6 for various lengths of time. It was found that PBOX-6 induces a transient activation of 2 JNK isoforms, JNK1 and JNK2, which peaks at 1 hour (FIG. 10).

Bcl-2 is an integral membrane protein located mainly on the outer membrane of mitochondria. Overexpression of Bcl-2 can prevent cells from undergoing apoptosis in response to a variety of stimuli. PBOX-6 caused a dose-dependent induction of apoptosis in human CEM (T lymphoblastoid) cells, both in normal (FIG. 11) and in CEM cells overexpressing the Bcl-2 protein (FIG. 12).

Some benzoxazepine compounds were found to induce apoptosis in three CML igi cell lines, K562, KYO.1 and Lama 84. A series of these compounds were tested at 10 $\mu$M and it was found that after a 16 hour treatment PBOX-3, 4, 5, 6 and 7 were the most potent, inducing up to 50% apoptosis (FIG. 13A). Some other benzoxazepines such as PBOX-1 and 2 failed to induce apoptosis in these cells at the same concentration. It was also found that some widely known PBR ligands such as PK 11195 and Ro5-4864 failed to induce apoptosis in CML cells at a similar concentration, however, apoptosis was induced, although not to the same extent, at the higher concentration of 100 $\mu$M (FIG. 13B).

PBOX-6 induced a time (FIG. 14A) and dose-dependent (FIG. 14B) induction of apoptosis in three CML cell lines, K562, KYO.1 and Lama 84. The morphological features of apoptosis, which include cell shrinkage, chromatin condensation, DNA fragmentation and the production of apoptotic bodies were visible in all cell lines. DNA fragmentation is considered to be the hallmark of apoptosis, and produces 180–200 bp internucleosomal DNA fragments which are visible as "DNA ladders" on a gel. This DNA laddering pattern was visible on an agarose gel when DNA was extracted from all three CML cell lines following treatment with PBOX-6 (FIG. 15).

Expression of the BCR-abl fusion protein in CML cells has been suggested to be responsible for the resistance of CML cells to many apoptotic agents. To investigate the effect of PBOX-6 on BCR-abl expression, levels of BCR-abl were determined by Western analysis of protein extracts isolated from control and PBOX-6 treated CML cells. In K562 and KYO.1 cells, downregulation of BCR-abl was detected, but not until 24 hours after PBOX-6 treatment (FIG. 16A and B), where approximately 50% of cells had undergone apoptosis. Downregulation of BCR-abl was not detected in Lama 84 cells up to 72 hours after treatment with PBOX-6 (FIG. 16C). Detection of β-actin was used as a loading control. These results suggest that downregulation of BCR-abl is not involved in the initial upstream events associated with PBOX-6 induced apoptosis.

Release of cytochrome C from mitochondria has been suggested to be important in triggering apoptosis. To determine the role of cytochrome C in PBOX-6-mediated apoptosis in CML cells, K562, KYO.1 and Lama 84 cells were exposed to the compound for 16 hours, and its effect on the accumulation of cytochrome C in the cytosol was determined. Cytosolic fractions were isolated and analysed for levels of cytochrome C by Western blotting. It has previously been shown that staurosporine treatment of HL-60 cells causes the release of cytochrome C into the cytosol. Therefore, treatment of HL-60 cells with 1 $\mu$M staurosporine for 6 hours was used as a positive control in setting up the assay (FIG. 17) It was found that cytochrome C levels in the cytosol were unchanged in CML cells after a 16 hour treatment with PBOX-6 (FIG. 17B, C, D). Cytochrome C. was evident in the cytosol of untreated CML cells probably due to non-specific release during sample preparation. In order to ensure that cytochrome C was not all non-specifically released during preparation of the cytosolic fractions, the remaining pellet was solublised and analysed for Cytochrome C levels. Western blots showed that the majority of cytochrome C remained in the pellet (FIG. 18). These results indicate that the release of cytochrome C from mitochondria may be important for triggering apoptosis in some cells in response to certain agents but does not occur during PBOX-6 induced apoptosis in CML cells.

Caspase 3 is one of the most intensely studied cysteine proteases and is believed to play a role of most downstream executioner in many apoptotic pathways. Control and apoptotic cell lysates from CML cells were isolated and examined for activated caspase 3 status, using a fluorogenic assay in which active caspase 3 will cleave a substrate (z-DEVD-AMC) and release the fluorogenic group (AMC), which can subsequently be measured using a spectrofluorimeter. The amount of AMC released was calculated from a standard curve of AMC, prepared using known concentrations. In the current study it has been shown that after 16 hours treatment with PBOX-6, caspase 3 is activated in two CML cell lines, K562 and Lama 84 (FIG. 19A). Caspase 3 activation correlates with the appearance of the morphological features of apoptosis as determined using the RapiDiff kit. Caspase 3 activation was not detected in KYO. 1 cells following treatment with PBOX-6 (FIG. 19A), although apoptosis was induced to the same extent in this cell line.

Certain cell lines eg. MCF-7 human breast carcinoma cells, have been shown to lack pro-caspase 3, and thus during apoptosis caspase 3 cannot become activated. To ensure that KYO.1 cells contain pro-caspase 3, a Western blot using an antibody directed against this proenzyme was set up. Results showed the presence of this proenzyme in all three CML cell lines (FIG. 19B).

CML cells were pretreated with a caspase 3 inhibitor, z-DEVD-fmk (200 $\mu$M), for 1 hr followed by treatment with PBOX-6 for a further 8 hours. Results show that pretreatment of K562 and Lama 84 cells with the caspase 3 inhibitor prevented the activation of caspase 3, as shown using the fluorogenic assay (FIG. 20A), but failed to prevent the induction of apoptosis by PBOX-6 (FIG. 20B). These results would suggest that although during apoptosis caspase 3 activation was detected in two of the CML cell lines, this activation is not an essential step in the pathway under which PBOX-6 induces apoptosis in CML cells.

There have been conflicting reports regarding the requirement of caspase 3 to cleave various death substrates (Martins et al., 1997; McGowan et al., 1996; Janicke et al., 1998). Having established that activation of caspase 3 is not necessarily required for the induction of apoptosis in CML cells, control and apoptotic cell lysates from CML cells were examined for evidence of PARP (poly ADP-ribose polymerase) cleavage. PARP (116 kDa) is cleaved during apoptosis into its 87 kDa and 29 kDa fragments which were detected by Western blot analysis of cell lysates. Results show that PARP cleavage occurs in K562 and Lama 84 cells following treatment with PBOX-6 for 24 and 16 hours respectively (FIG. 21A and 21B). In addition, the induction of apoptosis by PBOX-6 in KYO.1 cells, which does not involve caspase 3 activation, was also shown to result in PARP cleavage after 24 hours (FIG. 21C). These results would suggest that during apoptosis induced by PBOX-6 in CML cells, caspase 3 activation is not a requirement for PARP cleavage. Treatment of Hela cells with a representative PBOX compound, PBOX-3, induced PARP cleavage, demonstrating that these PBOX compounds can also induce apoptosis in a human cervix carcinoma cell line (FIG. 21D).

Several observations suggest an involvement of reactive oxygen intermediates (ROI) in the signal transduction pathway leading to apoptosis (Jacobson, 1996). In order to determine whether the induction of apoptosis in K562 cells by PBOX-6 involved the production of ROI, cells were pretreated with Vitamin E or N-acetylcysteine for 1 hour or 24 hours respectively, prior to treatment with PBOX-6 for a further 16 hours. These compounds failed to protect against PBOX-6 induced apoptosis (FIG. 22A and B) suggesting that the production of ROI is not involved in the mechanism by which PBOX-6 induces apoptosis in K562 cells.

Tyrosine phosphorylation is involved in the regulation of some apoptotic pathways. Protein tyrpsine kinases and phosphatases jointly maintain the tyrosine phosphorylation status of cellular proteins. In order to determine the effect of PBOX-6 on the tyrosine phosphorylation status of proteins in K562 cells, a Western blot assay was set up using an antibody directed against the phosphorylated form of tyrosine residues. Whole cell extracts from K562 cells were resolved by SDS-PAGE and membranes were probed with the antibody. Tyrosine phosphorylated proteins were observed. In this study, treatment of K562 cells with PBOX-6 for 5, 15 or 30 min, had no effect on the phosphorylation status of proteins (FIG. 23A). However, an increase in the phosphorylation of two proteins was detected in K562 cells following treatment with PBOX-6 for 16 hours (FIG. 23B). These proteins, as yet unidentified, are approximately 63 kDa and 71 kDa in size.

Pretreatment of K562 cells with the broad range phosphotyrosine kinase inhibitor, genistein (100 $\mu$M in DMSO), for 1 hr prior to PBOX-6 treatment, prevented the phosphorylation of these two proteins (FIG. 24A) and completely inhibited the induction of apoptosis (FIG. 24B). Pretreatment with herbimycin A (5 $\mu$M in DMSO) and tyrophostin (200 $\mu$M in DMSO), also commonly used tyrosine kinase inhibitors, reduced levels of apoptosis induced by PBOX-6 in K562 cells (FIG. 25), although they are themselves somewhat cytotoxic to the cells. Herbimycin A and tyrophostin alone induced approximately 30% and 10% apoptosis respectively.

Etoposide and mitoxanthrone are commonly used chemotherapeutic agents. These compounds are to poisomerase II inhibitors, also know as poisons, which stabilise the Topo II-DNA complex causing the accumulation of DNA strand breaks (Ritke et al., 1995). In agreement with previous reports (Martins et al., 1997), treatment of K562 cells with these compounds does not induce apoptosis (FIG. 26). In the present study, it has been found that pretreatment of K562 cells with these compounds for 1 hour prior to treatment with PBOX-6 for a further 16 hours protects against apoptosis. (FIG. 26). It could be suggested that PBOX-6 induces apoptosis by acting as a Topo II inhibitor, and that pretreatment of cells with other Topo II inhibitors, etoposide and mitoxanthrone, reduces the amount of available target for PBOX-6, thus preventing apoptosis.

To investigate whether PBOX-6 functions as a topoisomerase II poison in these cells, an alkaline elution assay was developed which measures DNA single strand breaks. The procedure is based on a previously reported finding that DNA from mammalian cells lysed on filters is eluted only very slowly by alkaline solutions, and that substantial increases in elution rates are produced by a relatively small extent of DNA strand breaks (Kohn et al., 1974). Values obtained from control cells which had undergone alkaline elution were taken as 100% and values obtained from the treatment of cells with various compounds was compared directly to this. As a positive control for the development of the assay to measure DNA strand breaks, Jurkat cells were treated with etoposide for 1 hour and cell extracts were lysed and eluted overnight with an alkaline solution. Results showed that etoposide induced a significant increase in DNA strand breaks (FIG. 27A). It was found that K562 cells, treated with PBOX-6 for 3 hours, did not show any significant increase in DNA strand breaks (FIG. 27B). These results would suggest that PBOX-6 does not function as a Topo II poison in K562 cells.

A series of compounds called ICRF compounds, including ICRF 154 and its derivative ICRF 193, have been shown to inhibit DNA topoisomerase II activity, but without intercalation into the DNA or the induction of cleavable complexes. These are catalytic inhibitors of Topo II as opposed to Topo II poisons which were described earlier (Ishida et al., 1991). It has been reported that these ICRF compounds inhibited Topo II mediated DNA breaks induced by etoposide (Tanabe et al., 1991) by reducing the amount of available target for etoposide. In the present study, pretreatment of Jurkat cells with ICRF 187 (200 $\mu$M) prevented etoposide induced DNA strand breaks (FIG. 28A) and also inhibited apoptosis induced by etoposide, as shown by RapiDiff staining (FIG. 28B). Pretreatment of K562 cells with ICRF 187 (200 $\mu$M) for 1 hour followed by PBOX-6 (10 $\mu$M) for a further 16 hours reduced but did not completely inhibit PBOX-6 induced apoptosis (FIG. 29). In order to determine if PBOX-6 operates in a similar way to these ICRF compounds, Jurkat cells were pretreated with a sub-cytotoxic concentration of PBOX-6 (0.5 $\mu$M) for 1 hour followed by treatment with etoposide (2.5 $\mu$M) for a further hour. Results showed that PBOX-6 did not prevent the induction of DNA strand breaks by etoposide (FIG. 30A). Jurkat cells were pretreated with PBOX-6 for 1 hour prior to treatment with etoposide for a further 16 hours and cells were spun onto a slide. Results from RapiDiff staining showed that PBOX-6 does not protect against etoposide induced apoptosis (FIG. 30B). These results suggest that PBOX-6 does not function in a manner similar to the topo II poisons or the catalytic inhibitors of topo II, however, results suggest that PBOX-6 may require topo II to function.

The mitogen activated protein kinase family (MAPK's), which includes p42–44, JNK and p38 have been shown to be activated during signal transduction in many cells in response to mitogens, growth factors, and various forms of stress (Denhardt, 1996). In order to determine the effect of PBOX-6 on the activation of MAPK's, a Western blot assay was developed. K562 cells were treated with vehicle or PBOX-6 for various lengths of time. It was found that PBOX-6 induces a transient activation of 2 JNK isoforms, JNK1 and JNK2, which first becomes visible after 15 min and peaks at 30–45 min (FIG. 31A). A gradual decrease in JNK activation was visible from 1 hour up to 8 hours after PBOX-6 treatment (FIG. 31B).

In Lama 84 and KYO.1 cells treated with PBOX-6 for 45 minutes, JNK1 and JNK2 were also found to be activated (FIG. 32).

A Western blot assay to detect activation of p38 was set up in which K562 cells were treated with vehicle or PBOX-6 and whole cell extracts were prepared. UV treatment of Jurkat cells was previously shown to activate p38, so was used as a positive control. Results showed that PBOX-6 failed to activate p38 following treatment periods of 5 min up to 8 hours (FIG. 33A and B). A similar time course was set up to determine whether the induction of apoptosis by PBOX-6 involved the activation of pt42–44. K562 cells treated with PMA for 30 minutes was used as a positive control, and results showed that P42–44 was not activated in response to PBOX-6 treatment (FIG. 34A and B).

The small GTP-binding proteins Rac1 and Cdc42 have been implicated in the regulation of the JNK signalling pathway (Coso et al., 1995). In an attempt to investigate events upstream of JNK activation a western blot was set up in which K562 cells were pretreated for 1 hour with a lethal toxin which inhibits the activity of Rac 1, and cells were then treated with PBOX-6 for a further 45 minutes. Results showed that pretreatment with the lethal toxin did not inhibit PBOX-6 induced JNK activation (FIG. 35A) and failed to inhibit the induction of apoptosis as determined by RapiDiff staining (FIG. 35B).

In the present study, it has been shown that the induction of apoptosis in K562 cells by PBOX-6 involves the transient activation of two JNK isoforms, JNK1 and JNK2. It has also been shown that pretreatment of these cells with the Topo II inhibitors, etoposide and ICRF 187 either prevents or reduces the extent of apoptosis induced by PBOX-6. Results suggest that PBOX-6 may require active Topo II to function. In order to determine whether a possible requirement for Topo II lies upstream of JNK activation, a western blot assay was set up in which K562 cells were pretreated with either etoposide or ICRF 187 prior to treatment with PBOX-6 and extracts were prepared and analysed for levels of JNK activation. Results show that pretreatment with etoposide (FIG. 36A) or ICRF 187 (FIG. 36B) failed to prevent against PBOX-6 induced activation of JNK, suggesting that a requirement for Topo II lies downstream of JNK activation in the pathway by which PBOX-6 induces apoptosis in K562 cells.

In order to determine the effect of PBOX-6 on normal bone marrow cells, samples were obtained from donors and cultures were set up to detect CFU-GM progenitors. Cells were treated with vehicle (0.5% ethanol, v/v) or PBOX-6 (10 $\mu$M) for 72 hours. Mean results from colony assays performed on 10 normal bone marrow samples was 16.9 for ethanol treated and 17 for PBOX-6 treated samples (Table 4). Statistical analysis of these data gave a p value of 0.9578, which is considered not significant.

PBOX-6 also induced apoptosis in MCF-7 cells, a human breast carcinoma cell line, in a dose-dependent manner. The morphological features of apoptosis as identified by cytospinning and staining of cells, was first observed and at a concentration of 5 $\mu$M (FIG. 37).

Discussion

The inventors have demonstrated that a new class of apoptotic agents, pyrrolo-1,5-benzoxazepines, induce cell death in a number of human cancerous cell lines, HL-60, Jurkat, Hut-78, LAMA 84, KYO.1, K562, CEM, Hela and MCF-7 cells. The morphological characteristics associated with apoptosis using previously defined criteria (Kerr et al., 1972) such as cell shrinkage, chromatin condensation, membrane blebbing and DNA fragmentation was observed. Of all these compounds screened in cells PBOX-3, 4, 5, 6 and 7 were found be most potent (much more potent than PK 11195 or Ro5-4864) whereas PBOX-1 and 2 had no effect.

PBOX-6 induces a time-and dose-dependent induction of apoptosis in HL-60 cells and in the 3 chronic myeloid leukaemia cells. Apoptosis was first observed after 4 hrs and with 5 $\mu$M PBOX-6. The induction of apoptosis by PBOX-6 was confirmed in all 4 cell lines by demonstrating the appearance of DNA Ladders, after a 48 hr treatment. DNA laddering is a hallmark of apoptosis and is a result of internucleosomal DNA degradation. The ultimate DNA fragments are multiples of 180–200 bp nucleosomal units which give the appearance of DNA laddering in standard agarose gels.

Multiple lines of evidence indicate that apoptosis can be triggered by the activation of a set of death effector cysteine proteases called caspases with specificity for Asp-X bonds. Some experimental observations would however suggest that a caspase-independent mechanism for commitment to cell death also exists. For example, overexpression of a proapoptotic protein such as Bax in mammalian cells can induce DNA condensation and membrane alterations leading to apoptosis, without any caspase activation (Xiang et al., 1996). In the present study we determined whether caspase-3 like proteases were involved in cell death induced by PBOX-6 in HL-60 cells. PBOX-6 caused a dose- and time-dependent activation of caspase 3-like proteases which directly correlated with the observed morphological effects of apoptosis induced by this compound. The caspase 3-like protease inhibitor, z-DEVD-fmk, prevented both the activity of caspase 3-like proteases and the appearance of the morphological signs of apoptosis. This would suggest the involvement of caspase 3-like proteases in the mechanism by which PBOX-6 induces apoptosis in HL 60 cells. In CML cells, caspase 3 was activated in response to PBOX-6 in only two out of the three cell lines whereas PBOX-6 induced apoptosis to a similar extent in all 3 cell lines. Pre-treatment of CML cells with a caspase 3 inhibitor, DEVD-fmk, did not protect against PBOX-6-induced apoptosis. This would indicate that activation of caspase 3 is not necessarily required for induction of apoptosis by PBOX-6 in these CML cells.

Overexpression of Bcl-2 can prevent cells from undergoing apoptosis in response to a variety of stimuli (Adams & Cory, 1998). PBOX-6 caused a dose-dependent induction of apoptosis in human CEM (T lymphoblastoid) cells, both in normal and in CEM cells overexpressing the Bcl-2 protein. This suggests that this pro-survival protein cannot protect against PBOX-6 induced apoptosis.

Cytochrome C is a mitochondrial protein that induces apoptosis when accumulated in the cytosol in response to diverse stress inducers (Kluck et al., 1997; Yang et al., 1997). This protein has also been shown to cause apoptosis when added to cell free extracts (Liu et al., 1996). In some cell lines however, such as multiple myeloma cells, there are at least two different pathways that lead to apoptosis, one involving and one not involving Cytochrome C release from mitochondria (Chauhan et al., 1997). These workers studied the role of Cytochrome C in dexamethasone-, anti-Fas mAb- and ionizing radiation-induced apoptosis and demonstrated that while ionizing radiation-induced apoptosis is associated with an increase in cytosolic Cytochrome C levels, apoptosis induced by the two other agents had no detectable effect on Cytochrome C release. In addition, there are many reports that during apoptosis, accumulation of Cytochrome C in the cytosol results in the activation of caspase 3-like proteases (Kluck el aL, 1997; Chu et al., 1997) although pathways leading to caspase 3 activation without Cytochrome C release have also been described (Chauhan et al., 1997). In the present study, PBOX-6-induced apoptosis in HL 60 cells was associated with an accumulation of Cytochrome C in the cytosol. This result indicates that release of Cytochrome C from the mitochondria may be important for triggering apoptosis in response to PBOX-6. This was not the case with the CML cells. PBOX-6 did not cause an increase in the release of cytochrome C into the cytosol of CML cells. This would suggest that cytochrome C is not involved in the mechanism in which PBOX-6 induces apoptosis in CML cells.

Apoptosis is sometimes associated with increases in intracellular ROI levels and addition of exogenous antioxidants such as N-acetylcysteine (NAC) and vitamin E can inhibit apbptosis (Butke and Sandstrom, 1994). The specific molecular mechanisms involved however remain to be elucidated. In the present work it has been shown that PBOX-6-induced apoptosis in HL60 cells and in K562 cells was unaffected by the presence of a number of antioxidants. This would suggest that PBOX-6-induced apoptosis is not mediated by ROI. This is in agreement with recent reports which have indicated that ROI are not necessarily a requirement for apoptosis. For example, programmed cell death induced by the Fas ligand or by staurosporine do not appear to require the generation of ROI, and are not inhibited by the use of antioxidants (Jacobson and Raff, 1995).

Recently there has been some suggestion that the PBR may be involved in apoptosis. A group of workers have shown that PK 11195, a prototypic ligand of the PBR, facilitates the induction of apoptosis by a variety of stimuli in a number of cell types including thymocytes and the T-cell leukaemia CEM cells (Hirsch et al., 1998). However, PK 11195 by itself had no apoptotic effect. In addition, it has been recently reported that during apoplosis Cytochrome C can exit the mitochondria through VDAC (Shimizu et al., 1999), which is itself associated with the PBR in the mitochondrial outer membrane (McEnery et al., 1992). In the present study we describe how PK 11195 and some PBOX compounds induce apoptosis by themselves, independently of other apoptosis-inducing stimuli. It is unlikely however that the PBR is involved in the mechanism by which these PBOX compounds induce apoptosis. Much higher concentrations of the compounds were required to induce apoptosis than were necessary to saturate the receptor. Furthermore, some of the compounds e.g. PBOX-1 and PBOX-2, did not induce apoptosis, yet all of these compounds bind to the receptor with similar affinity. Finally, we have shown that some PBOX compounds induce apoptosis in Jurkat cells which have previously been shown to be devoid of the PBR (Carayon et al., 1996). These studies demonstrate that the apoptotic effects of the PBR ligands are incompatible with PBR involvement.

Several recent papers have shown that activation of the transcription factor NFκB is linked to apoptosis (Beg and Baltimore, 1996; Giri and Aggarwal, 1998). There have been some suggestions that this factor once activated plays an anti-apoptotic role, most likely by inducing expression of gene products, such as cIAP2 (cellular inhibitor for apoptosis) (Chu et al., 1997), that inhibit the apoptotic pathway. However, a general role for NFκB as a transcription factor that prevents apoptosis is far from established.

The activation of NFκB is initiated by a wide variety of stress stimuli, such as TNF, ceramide and daunorubicin, which themselves cause apoptosis (Boland et al., 1997). In this case NFκB activation may then cause cell death. Thus the role of NFκB as a promoter or inhibitor of cell death may depend on both the cell type fit and the apoptosis-inducing stimulus.

In the present study we have shown that while PBOX-6 induced apoptosis in both HL-60 and Hut-78 cells, this compound did not affect NFκB levels. Hut-78 cells constitutively express NFκB and as such have been reported to be resistant to a range of stress stimuli including TNF, lipopolysacharide, $H_2O_2$, ceramide and okadaic acid (Giri and Aggarwal, 1998). In this work the PBOX compounds induced apoptosis in both HL-60 and Hut-78 cells, with similar potency. Furthermore, pre-treatment of HL-60 cells with TNF at a concentration which activates NFκB, afforded no protection against PBOX-6-induced apoptosis. It can thus be concluded that PBOX-6-induced apoptosis most likely employs an NFκB-independent mechanism. Furthermore this study argues against a general role for NFκB as a transcription factor that prevents cell death.

Several anti-cancer drugs such as camptothecin (Piret and Piette, 1996), etoposide (Perez el at., 1997) and the anthracycline antibiotics, daunorubicin and doxorubicin (Das and White, 1997), activate NFκB in addition to inducing cell death. Daunorubicin is widely used in cancer chemotherapy and although its mechanism of anti-tumour action has not been fully elucidated, it ultimately induces apoptosis in cells. The concomitant activation of NFκB may counteract the therapeutic effects of these chemotherapeutic compounds. Therefore anti-cancer drugs which do not activate NFκB may result in more effective anti-cancer treatments.

It is evident that apoptosis can be induced by a variety of drugs with diverse chemical structure and different mechanism of action. Among the list of apoptosis inducing agents are a wide range of anti-cancer drugs including inhibitors of the mitotic spindle apparatus, such as vinca alkaloids, inhibitors of DNA synthesis such as aphidicolin and drugs like campothecin that cause protein-associated DNA strand breaks mediated by DNA topoisomerase I (Sen and D'Incalci, 1992). All these drugs have been shown to induce apoptosis in cancerous cells derived from the haemopoietic system such as HL-60 cells (Sen and D'Incalci, 1992). We propose that these pyrrolo-1,5-benzoxazepines may be potential anti-cancer drugs. The observation that these compounds do not activate NFκB may also result in them being more effective anti-cancer agents.

The BCR-abl fusion gene transcribes a novel 8.6 kb mRNA which in turn encodes a p210 kDa protein which, unlike normal c-abl protein, is phosphorylated on tyrosine residues and has increased intrinsic tyrosine kinase activity. It has been suggested that p210 bcr-abl tyrosine kinase may have an important role in the pathogenesis of CML (Clarkson et al., 1997). The BCR-abl fusion gene is probably the usual sole causative event and is responsible for all the manifestations of the early chronic phase of the disease (Clarkson et al., 1997). In this study, it has been shown that BCR-abl is down regulated in two of the three CML cell lines after treatment with PBOX-6. However, down regulation was not detected before 24 hr treatment with 10 μM PBOX-6 at which time apoptotic levels reach approximately 50%. Therefore, it is unlikely that downregulation of the BCR-abl fusion protein is the initial target of the drug.

The cleavage of PARP in all three CML cell lines was demonstrated after treatment with PBOX-6 for 24 hr. During apoptosis PARP has been suggested to be cleaved by caspases 3 and/or 7 (Cohen, 1997). The induction of PARP cleavage in the KYO.1 cells, where caspase 3 is not activated, would suggest that caspase 3 is not required for PARP cleavage in these cells upon induction of apoptosis by PBOX-6. These results are in agreement with a recent report in which it was shown that MCF-7 breast carcinoma cells, which lack caspase 3, underwent PARP cleavage after treatment with the apoptotic inducer staurosporine (Janicke et al., 1998).

Phosphorylation and dephosphorylation of cellular proteins is implicated in many biologically important processes such as cell growth and differentiation (Weng et al., 1998). Protein tyrosine kinases (PTK's) and phosphatases (PTPases) jointly maintain the tyrosine phosphorylation of cellular proteins in homeostasis (Yousefi et al., 1994). Alteration in the tyrosine phosphorylation status of proteins has previously been implicated in apoptotic cell death (Uckun et al., 1992). There also appears to be conflicting reports as to whether an increase or decrease in the tyrosine phosphorylation status of proteins results in apoptosis (Bergamaschi et al., 1993; Johnson et al., 1996). In this study it has been shown that treatment of K562 CML cells with PBOX-6 induces an increase in the tyrosine phosphorylation status of two proteins, approximately 63 kDa and 71 kDa in size. Pretreatment of cells with the general tyrosine kinase inhibitor, genistein, blocked the phosphorylation of these proteins by PBOX-6 and also prevented the induction of apoptosis. In conclusion, an increase in the tyrosine phosphorylation of two, as yet unidentified proteins, has been observed in K562 cells following treatment with PBOX-6. This increased phosphorylation did not become apparent until 16 hours following the addition of PBOX-6 where approximately 40–50% of cells had undergone apoptosis. Therefore, from these results it can be suggested that increased tyrosine phosphorylation of these two proteins, following treatment with PBOX-6, does not trigger the induction of apoptosis but rather accompanies apoptosis induced in K562 cells. Treatment of Jurkat cells with PBOX-6 causes a time and dose-dependent decrease in protein tyrosine phosphorylation which correlates with the appearance of the morphological signs of apoptosis. As this downregulation does not precede the appearance of the morphological signs of apoptosis, it is unlikely that it is an upstream event in the apoptotic pathway in which PBOX-6 causes cell death.

The DNA binding protein, topoisomerase II, is a target for several clinically effective anticancer drugs, among which are mitoxanthrone and etoposide. These compounds stabilise the DNA-Topo II complex preventing the religation of cleaved DNA strands which results in the accumulation of strand breaks (Perez et al., 1997). In the present study it has been demonstrated that treatment of K562 cells with these Topo II inhibitors protects against PBOX-6 induced apoptosis. It could possibly be suggested that PBOX-6 also acts as a Topo II poison and that pretreatment of cells with another poison such as etoposide reduces the amount of available target for PBOX-6, thus reducing the extent of apoptosis. However, it is unlikely that PBOX-6 functions in a similar manner to these Topo II poisons as demonstrated by its failure to induce DNA strand breaks.

Another series of compounds, Bis 2,6-dioxopiperazine derivatives, which include ICRF 154 and ICRF 193 have been shown to be new anti-tumour agents and are currently under clinical trial. These drugs inhibit topoisomerase II activity, but not topoisomerase I. They do not intercalate into the DNA or induce the cleavable complex, but rather block the catalytic activity of the enzyme by directly intercalating with the enzyme and not with DNA (Tanabe et al., 1991). They are thus called catalytic Topo II inhibitors. ICRF-193 has also been shown to inhibit DNA stand breaks induced by other cleavable complex-forming agents. Thus ICRF-193 antagonized etoposide or amsacrine-stimulated DNA strand cleavage, and the resulting apoptosis suggesting that ICRF-193 and related compounds block at some earlier step in the catalytic cycle of the enzyme reaction (Tanabe et al., 1991). These observations were confirmed in the present study by the demonstration that ICRF 187 prevented etoposide-induced apoptosis in Jurkat cells and prevented etoposide-mediated DNA strand breaks. Although ICRF 187 caused a reduction in levels of PBOX-6 induced apoptosis in K562 cells, results suggest that PBOX-6 does not function in a manner similar to these ICRF compounds as it does not protect against etoposide-induced DNA strand breaks or etoposide-induced apoptosis in Jurkat cells.

In agreement with previous reports (Ritke et al., 1994) it was observed that the treatment of K562 cells with etoposide (25 μM) induced DNA strand breaks. However, unlike Jurkat cells, K562 cells failed to undergo apoptosis up to 24 hours following treatment with etoposide. A possible explanation may be the ability of K562 cells to repair DNA damage induced by etoposide. Further studies need to be carried out to investigate a possible DNA repair mechanism in K562 cells.

Receptor tyrosine kinases (RTKs) have been shown to activate a number of intracellular signaling pathways during signal transduction. Three kinases, p38, p42–44, and JNK, known as MAPK's, are found in the nucleus upon activation and serve to link signals from the cell surface to cytoplasmic and nuclear events.

Many reports suggest a role for MAPK's, including JNK and p38, in the cellular response to various extracellular stimuli and in the induction of apoptosis. For example, in Jurkat cells, JNK and p38 activation have been coupled to Fas-induced apoptosis (Juo et al., 1997). The induction of apoptosis in U937 cells by etoposide or camptothecin resulted in the transient activation of JNK1 which in turn led to transient expression of c-jun (Seimiya et al., 1997). However, a number of reports suggest that the specific signal transduction pathways activated during apoptosis may vary in response to different stimuli and between cell types (Osborn and Chambers, 1996). Similar observations have been reported for p38 activation. For example, in human neutrophils, apoptosis induced by stress stimuli resulted in activation of p38, but not JNK, within 30 minutes following stimulation. In contrast, apoptosis induced by Fas ligation failed to activate either p38 or JNK in the same cells (Frasch et al., 1998). In the present study, transient activation of JNK was observed in K562 cells following a 15 minute treatment with PBOX-6 and induction of apoptosis followed. JNK activation peaked following 30–45 minutes treatment with PBOX-6 and levels of activation slowly declined over an 8 hour period. Transient activation of JNK was also observed in HL-60 cells following treatment with PBOX-6. Induction of apoptosis by PBOX-6, in K562 cells, failed to activate p38 or p42–44 up to 8 hours after treatment. In an attempt to identify proteins activated upstream of JNK, K562 cells were pretreated with a lethal toxin which inhibits Rac 1. Rac 1, a member of a group of small GTP-binding proteins, has previously been implicated upstream of JNK (Coso et al., 1995). However, inhibition of Rac 1 failed to prevent PBOX-6 induced activation of JNK in K562 cells indicating that activation of Rac 1 does not lie upstream of JNK in the pathway in which PBOX-6 induces apoptosis in K562 cells.

In the present study it has been shown that PBOX-6 induces transient activation of two JNK isoforms, JNK 1 and JNK 2 during apoptosis in K562 cells. It has also been shown that pretreatment of K562 cells with the Topo II inhibitors, etoposide and ICRF 187 either inhibited or reduced the extent of apoptosis induced by PBOX-6. These results suggest that PBOX-6 requires active Topo II for the induction of apoptosis. Using western blot analysis it has been shown that activation of JNK lies upstream of a requirement for Topo II in the pathway by which PBOX-6 induces apoptosis in K562 cells.

In the present study it has been shown that K562 cells, which are resistant to most anti-cancer agents, readily undergoes apoptosis when treated with this novel anti-cancer agent. To ensure that PBOX-6 does not elicit a general toxic effect, normal bone marrow samples were received from 10 donors. Mononucleur cells were isolated from the samples and subsequently treated with PBOX-6. Stem cell progenitor cultures were prepared and results indicated that PBOX-6 has no significant effect on normal bone marrow stem cells.

Whether other components acting in parallel pathways are also required, in addition to the activation of JNK and caspase 3-like proteases, for the induction of apoptosis by PBOX-6 has not been determined. The mechanism(s) of activation of the caspase(s) and the potential targets involved in this process will need to be identified. In conclusion, it has been demonstrated that the compounds of the present invention can induce apoptosis in cancerous cell lines, indicating the potential of these compounds as anti-tumour drugs.

Summary

A range of pyrrolobenzoxazepine derivatives (PBOX compounds) have been shown to induce apoptosis, with various potencies, in the following nine human cancer cell lines: HL 60 (promyelocytic leukaemia), HUT 78 (T cell Lymphoma), Jurkat (leukaemic T cell Lymphoblast) and LAMA 84, KYO.1, K562 (chronic myeloid leukemia cells), Hela (cervix carcinoma) CEM (T lymphoblastoid) and MCF-7 (breast carcinoma) cells. The induction is both dose and time-dependent. It does not appear to involve the specific interaction of these ligands with the peripheral-type benzodiazepine receptor (PBR), to which they bind with high affinity, as much higher concentrations of these compounds were required to induce apoptosis than were necessary to saturate the receptor. In addition, some of the PBOX compounds induce apoptosis in Jurkat cells, which have previously been reported to lack the PBR.

PBOX compound-induced apoptosis was unaffected by the presence of antioxidants such as N-acetylcysteine, suggesting that the mechanism by which these compounds cause apoptosis does not involve the production of reactive oxygen intermediates.

Activation of the transcription factor NF kappa B has previously been suggested to protect against apoptosis. Five selected PBOX compounds induced apoptosis in HUT 78 cells which contain constitutively active NF kappa B, albeit with reduced potency to that observed in HL 60 cells. In addition, activation of NF Kappa B by the cytokine TNF-alpha in HL 60 cells prior to the addition of PBOX-6 did not protect these cells against apoptosis. Furthermore, PBOX-6-induced apoptosis did not effect the levels of NF kappa B activity in either HUT 78 or HL 60 cells. These results would suggest that PBOX-6-induced apoptosis employs an NF kappa B-independent mechanism.

Caspases are a closely related family of cysteine proteases that play a key role in apoptosis. In this study it was shown that caspase 3 becomes activated during PBOX-6-induced apoptosis in HL60 cells. In addition, pre-treatment of HL 60 cells with a specific inhibitor of caspase 3, z-DEVD-fmk, inhibits apoptosis induced by PBOX-6. These results indicate that caspase 3 plays an important role in apoptosis in response to PBOX-6 in HL60 cells.

PBOX-6-induced apoptosis in HL60 cells was associated with an accumulation of the mitochondrial protein cytochrome C in the cytosol, which may be important for triggering apoptosis. This was not the case with the CML cells. Results would indicate that activation of caspase 3 and release of cytochrome C is not required for induction of apoptosis by PBOX-6 in these CML cells.

PBOX-6 caused a dose-dependent induction of apoptosis in human CEM (T lymphoblastoid) cells, both in normal and in CEM cells overexpressing the Bcl-2 protein. This suggests that this pro-survival protein cannot protect against PBOX-6 induced apoptosis.

The BCR-abl fusion protein is probably responsible for the manifestation of CML. It is unlikely, however, that the BCR-abl fusion protein is the initial target of the PBOX-6, as its down regulation in response to PBOX-6 in two of the CML cell lines does not occur until after 24 hours.

Recent reports suggest that signalling through protein tyrosine phosphorylation is required for the induction and/or inhibition of apoptosis. Treatment of Jurkat cells and the CML cells with PBOX-6 resulted in changes in protein tyrosine phosphorylation levels.

Pre-treatment of Jurkat cells and K562 cells with the topoisomerase II inhibitors etoposide, genisten and mitoxantrone reduced the levels of apoptosis by PBOX-6. This may suggest that PBOX-6 could also be working at the level of the DNA and that the topoisomerase II inhibitors and PBOX-6 are competing with one another for binding to the DNA. It was found that both Topo II poisons and catalytic inhibitors of Topo II either reduced or completely inhibited PBOX-6 induced apoptosis in K562. However, it seems unlikely that PBOX-6 functions in a manner similar to either the Topo II poisons or catalytic inhibitors, but that PBOX-6 requires active Topo II to function.

PBOX-6 induced apoptosis in CML and HL-60 cells involved the transient activation of JNK. The small GTP-binding protein Rac 1 does not seem to be activated upstream of JNK.

Activation of JNK lies upstream of a requirement for Topo II in the pathway by which PBOX-6 induces apoptosis in K562 cells.

The induction of apoptosis in K562 cells did not involve the activation of the MAPK's p38 or p42–44 following up to 8 hours treatment with PBOX-6.

Finally PBOX-6 was found to have no effect on normal myeloid cells.

The words "comprises/comprising" and the words "having/including" when used herein with reference to the present invention are used to specify the presence of stated features, integers, steps or components but does not preclude the presence or addition of one or more other features, integers, steps, components or groups thereof.

References

Adams, J. M. and Cory, S. (1998) Science 281, 1322–1325.
Baeuerle, P. A. and Henkel, T. (1994) Ann. Rev. Immunol. 12, 141–179.
Baichwal, V. R. and Baeuerle, P. A. (1997) Current Biology 7, R94–R96.
Beg, A. A. and Baltimore, D. (1996) Science 274, 782–784.
Beidler, D. R., Tewari, M., Friesen, P. D., Poirier, G. and Dixit, V. M. (1995) J. Biol. Chem. 270, 16526–16528.
Bergamaschi, G., Rosti, V., Danova, M., Ponchio, L., Lucotti, C. & Cazzola, M. (1993) Leukemia 7, 2012–2018.
Boland, M. P., Foster, S. J. and O'Neill L. A. J. (1997) J Biol Chem 272, 12952–12960.
Bradford, M. M. (1976) Anal. Biochem. 73, 248–254.
Braestrup, L. and Squires, R. F. (1977) Proc. Natl. Acad. Sci. U.S.A. 74, 1839–1847.
Buttke, T. M. and Sandstrom, P. A. (1994) Immunol. Today 15, 7.
Burden, D. A. and Oserhoff, N. (1998) Biochimica Biophysica Acta, 1400, 139–154.
Camins, A., Diez-fernandez, C., Pujadas, E., Camarasa, J. and Escubedo, E. (1995) Eur. J. Pharmacol. 272, 289–292.
Campiani, G., Nacci, V., Fiorini, I., De Filippis, M. P., Garofalo, A., Ciani, S. M., Greco, G., Novellino, E., Williams, D. C., Zisterer, D. M., Woods, M. J., Mihai, C., Manzoni, C. and Mennini, T. (1996) J. Med. Chem. 39, 3435–3450.
Carayon, P., Portier, M., Dussossay, D., Bord, A., Petitpretre, G., Canat, X., Le Fur, G. and Casellas, P. (1996) Blood 86, 3170–3178.
Chauhan, D., Pandey, P., Ogata, A., Teoh, G., Krett, N., Halgren, R., Rosen, S., Kufe, Clarkson, B. D., Strife A., Wisniewski D., Lambek C., Carpino N. (1997) Leukemia 11, 1404–1428.
Chu, Z-L., McKnisey, T. A., Liu, L., Gentery, J., Malim, M. H., and Ballard, D. W. (1997) Proc Natl Acad Sci USA 94, 10057–10062.
Clarkson, B. D., Strife, A., Wisniewski, D., Lambek, C. & Carpino, N. (1997) Leukemia 11, 1404–1428.
Cohen, G. M. (1997) Biochem J. 326, 16–20.
Cosa, O. A., Chiariello, M., Yu, C., Teramoto, H., Crespo, P., Xu, N., Miki, T. & Gutkind, J. S. (1995) Cell 81, 1137–1146.
Costa, E. and Guidotti, A. (1979) Ann. Rev. Pharmacol. Toxicol. 19, 531–545.
Das, K. C. and White, C. W. (1997) J. Biol. Chem. 272, 14914–14920.
Denhardt, D.T. (1996) J. Biochem. 318, 729–747.
Eischen, C. M., Christopher D. J. and Leibson P. J. (1994) Journal of Immunology 153, 1947–1950.
Frasch, S. C., Nick, J. A., Fadok, V. A., Bratton, D. L., Worthen, G. S. & Henson, P. M. (1998) J. Biol. Chem. 273, 8389–8397.
Giri, D. K. and Aggarwal, B. B. (1998) J Biol Chem. 273, 14008–14014.
Gorman, A. M. C., OBeirne, G. B., Regan C. M. and Williams, D. C. (1989) J. Neurochem. 53, 849–855.
Grilli, M., Pizzi, M., Memo, M. and Spano, P. F. (1996) Science 274, 1383–1385.
Hirsch, T., Decaudin, D., Susin, S. A., Marchetti, P., Larochetter, N., Resche-Rigon, M. and Kroemer, G. (1998) Exp Cell Res 241, 426–434.
Hunter, T. (1995) Cell 80, 225–236.
Ikezaki, K. and Black, K. L. (1990) Cancer Lett. 49, 115–120.
Ishida, R., Miki, T., Narita, T., Yui, R., Sato, M., Utsumi, K. R., Tanabe, K. & Andoh, T. (1991) Can. Res. 51, 4909–4916.
Jacobson, M. D. and Raff, M. C. (1995), Nature 374: 814–816.
Janicke, R. U., Patrick N, Sprengart, M. L., Alan G. Porter, A. G. (1998) J. Biol. Chem. 273, 15540–15545.
Johnson, K. L., Vaillant, F. & Lawen, A. (1996) FEBS Lett. 383, 1–5.
Juo, P., Kuo, C. J., Yuan, J. & Blenis, J. (1998) Curr. Biol. 8, 1001–1008.
Kakeya, H., Onose, R. and Osada, H. (1998) Can. Res. 58, 4888–4894.

Kerr, J. F. R., Wylie, A. H. and Currie, A. R. (1972) *Br. J. Cancer* 26, 239–257.

Kharbanda, S. and Anderson, K. (1997) *J. Biol. Chem.* 272, 29995–29997.

Kluck, R. M., Bossy-Wetzel, E., Green, D. R. and Newmeyer, D. D. (1997) *Science* 275, 1132–1136.

Kohn, K. W., Friedman, C. A., Ewig, R. A. G. & Iqbal, Z. M. (1974) *Biochemistry* 13, 4134–4139.

Lumelsky, N. L. and Schwartz, B. S. (1996) *Cancer Research* 56, 3909–3914.

Liu, Z.-G., Hsu, H. Goeddel, D. and Karin, M. (1996) *Cell* 87, 565–576.

Martin, S. J., Newmeyer, D. D., Mathias, S., Farschon, D. M., Wang, H., Reed, J. C. and Green, D. R. (1995) *EMBO J.* 14, 5191–5200.

McEnery, M. W., Snowman, A. M., Trifiletti, R. R. and Snyder, S. H. (1992) *Proc. Natl. Acad. Sci. USA* 89, 3170–3174.

McGowan, A. J., Ruiz-Ruiz, M. C., Gorman, A. M., Lopez-Rivas, A. & Cotter, T. G. (1996)i FEBS Lett. 392, 299–303.

Munson, P. J. and Rodbard, D. (1980) *Anal. Biochem* 107, 220–239.

Nicholson, D. W. and Thornbury, N. A. (1997) *Trends Biochem. Sci.* 22, 299–306.

Nicholson, D. W., Ali, A., Thombenry, N. A., Vaillancourt, J. P., Ding, C. K. Gallant, M., Gareau, Y., Griffin, P. R, Labelle, M., Lazebnik, Y. A., Munday, N. A., Raju, A. M., Smulson, M. E., Yamin, T.-T., Yu, V. L. and Miller, D. K. (1995) *Nature* 376, 37–43.

O'Beirne, G. B. and Williams, D. C. (1988) *Euro. J. Biochem.* 177, 413–421.

O'Connell, M. A., Cleere, R., Long, A., O'Neill, L. A. J. and Kelleher, D. (1995) *J. Biol. Chem.* 270, 7399–7404.

Osborn, M. T. & Chambers, T. C. (1996) *J. Biol. Chem.* 271, 30950–30955.

Perez, C., Vilaboa, N. E., Garcia-Bermejo, L., de Blas, E., Creighton, A. M. and Aller, P. (1997) *J. Cell Sci.* 110, 337–343.

Piret, B. and Piette, J. (1996) *Nucleic Acids Res.* 24, 4242–4248.

Polverino, A. J. and Patterson, S. D. (1997) *J. Biol. Chem.* 272, 7013–7021.

Ritke, M. K., Murray, N. R., Allan, W. P., Fields, A. P. & Yalowich. J. C. (1995) *Mol. Pharmacol.* 48, 798–805.

Sabbatini, P., Han, J. H., Chiou, S.-K., Nicholson, D. and White, E. (1997) *Cell Growth and Diff. (in press).*

Seimiya, H., Mashima, T., Toho, M. & Tsuruo, T. (1997) *J. Biol. Chem.* 272, 4631–4636.

Sen, S. and D'Incalci, M. (1992) *FEBS Letts* 307, 122–127.

Shimizu, S., Narita, M. and Tsujimoto, Y. (1999) *Nature* 399, 483–487.

Shoemaker, H., Bliss, M. and Yamamura, H. I. (1981) *Eur. J. Pharmac.* 71, 173–175.

Stylianou, E., O'Neill, L. A. J., Rawlinson, L., Edbrooke, M. R., Woo, P. and Saklatvala, J. (1992) *J. Biol. Chem.* 267, 15836–15841.

Tanabe, K., Ikegami, Y., Ishida, R & Andoh, T. (1991) *Can. Res.* 51, 4903–4908.

Tewari, M., Quan, L. T., O'Rourke, K., Desnoyers, S., Zeng, Z., Beidler, D. R., Poirier, G. G., Salvesen, G. S. and Dixit, V. M. (1995) *Cell* 81, 801–809.

Uckun, F. M., Tuel-Ahigren, L., Song, C. W., Waddick, K., Myers, D. E., Kirihare, J., Ledbetter, J. A. & Schieven, G. L. (1992) *Med. Sci.* 89, 9005–9009.

Usami, I., Kubota, M., Bessho Y., Kataoka, A. Koishi, S., Watanabe, K-I., Sawada, M., Lin, Y. W., Akiyama, Y. and Furusho, K. (1998) *Biochem. Pharmacol.* 55, 185–191.

Van Antwerp, D. J., Martin, S. J., Kafri, T., Green, D). and Verma, I. M. (1996) *Science* 274, 787–789.

Wang, C.-Y., Mayo, M. W. and Baldwin, A. S. Jr. (11996) *Science,* 274, 784–787.

Wang, J. K. T., Morgan, J. I. and Spector, S. (1984a) *Proc. Natl. Acad. Sci. USA.* 81, 3770–3772.

Wang, J. K. T., Morgan, J. I. and Spector, S. (1984b) *Proc. Natl. Acad Sci. USA.* 81, 753–756.

Weng, L. P., Yuan, J. & Yu, Q. (1998) *Curr. Biol.* 8, 247–256.

Wu, M., Lee, H., Bellas, R. E., Schauer, S. L., Arsura, M., Katz, D., FitzGerald, M. J., Rothstein, T. L., Sherr, D. H. and Sonenshein, G. E. (1996) *EMBO J.* 15, 4682–4690.

Xiang, J., Chao, D. T. and Korsmeyer, S. J. (1996) *Proc. Natl. Acad Sci. U.S.A.,* 93, 14559–14563.

Yang, J., Kiu, X., Bhalla, K., Kim, C.N., Ibrado, A-M, Cai, J., Peng, T-I, Jones, D. P. and Wang, (1997) *Science* 275, 1129–1132.

Yousefi, S., Green, D. R., Blaser, K. & Simon, H. (1994) *Proc. Natl. Acad. Sci. USA.* 91, 10868–10872.

Yuan, J., Shaham, S., Ledoux, S., Ellis, H. M. and Horvitz, H. R. (1993) *Cell* 75, 641–652.

Zisterer, D. M. and Williams, D. C. (1997) *Gen. Pharmac.* 29, 305–314.

Zisterer, D. M., Hance, N., Campiani, G., Garofalo, A., Nacci, V. and Williams, D. C. (1998) *Biochem. Pharmacol.* 55, 397.

TABLE 1

Summary of peripheral-type and central-type benzodiazepine receptor characteristics

|  | Peripheral-type | Central-type |
|---|---|---|
| Tissue distribution | Ubiquitously distributed in peripheral tissues (especially steroidogenic) as well as in glia of CNS | Neuronal |
| Subcellular localisation | Mitochondrial outer membrane | Plasma membranes |
| Synthetic ligands | Isoquinolines (e.g. PK 11195), benzodiazepines-(e.g. Ro5-4864, species-dependent, GABA-insensitive) | Benzodiazepines-(e.g. clonazepam, GABA-sensitive) |
| Endogenous ligands | diazepam binding inhibitor (DBI) | DBI |
| Molecular components | Isoquinoline binding protein (18 kDa), mitochondrial VDAC (32 kDa), ANC (30 kDa) | Heterogenous $\alpha$, $\gamma$ subunits of GABA$_A$ receptor |
| Effector mechanism | cholesterol transport? | Regulates chloride flux by modulating GABA binding to GABA$_A$ receptor |

TABLE 2

Effect of PBOX compounds on apoptosis in HL-60 cells

| Compound | % Apoptosis |
|---|---|
| Control | 1.1 ± 1.2 |
| PBOX 3 | 23.5 ± 2.1 |
| PBOX 4 | 42.1 ± 0.6 |
| PBOX 5 | 27.6 ± 4.2 |
| PBOX 6 | 38.6 ± 4.6 |
| PBOX 7 | 40.7 ± 2.5 |
| PBOX 8 | 38.6 ± 3.1 |
| PBOX 9 | 40.4 ± 3.0 |
| PBOX 12 | 27.1 ± 2.7 |
| PBOX 24 | 7.0 ± 1.2 |
| PBOX 25 | 19.2 ± 3.0 |
| PBOX 26 | 7.8 ± 2.3 |

TABLE 2-continued

Effect of PBOX compounds on apoptosis in HL-60 cells

| Compound | % Apoptosis |
|---|---|
| PBOX 27 | 11.8 ± 3.2 |
| PBOX 28 | 31.1 ± 1.7 |
| PBOX 30 | 33.1 ± 1.6 |

HL-60 cells were seeded at a density of 3 × 10$^5$ cell/ml into 24-well plates and treated for 16 h with the various PBOX compounds (10 μM) listed above. Control wells contained 1% (v/v) ethanol. Percent apoptosis was determined after cytospinning and staining the cells. The values represent the mean ± range of two experiments.

TABLE 3

High affinity binding f pyrrolobenzoxazepines to homogenates of HL-60 cells

| Compound | Inhibition of [$^3$H]PK 11195 binding to the PBR, Ki value (nM) |
|---|---|
| PBOX-1 | 3.4 ± 0.2 |
| PBOX-2 | 1.2 ± 1.1 |
| PBOX-3 | 6.0 ± 1.9 |
| PBOX-4 | 1.9 ± 2.3 |
| PBOX-5 | 1.1 ± 0.9 |
| PBOX-6 | 6.7 ± 1.7 |
| PBOX-7 | 1.7 ± 0.7 |

Homogenates (50 μg of protein) of HL-60 cells were assayed for specific binding of [$^3$H]PK 11195 binding (2 nM) in the presence and absence of the indicated unlabelled displacing compound 0–1 μM. The amount of radioactivity bound in the presence of the displacer was expressed as a percentage of control bonding and the values represent the mean±SEM of triplicate determinations from one representative experiment performed at least twice. The Ki values were obtained as described in Methods section.

| Normal Bone Marrow | 0.5% Ethanol | 10 μM PBOX 6 |
|---|---|---|
| 1 | 10 | 10 |
| 2 | 13 | 16 |
| 3 | 17 | 16 |
| 4 | 22 | 22 |
| 5 | 22 | 19 |
| 6 | 15 | 11 |
| 7 | 16 | 20 |
| 8 | 14 | 17 |
| 9 | 24 | 18 |
| 10 | 17 | 20 |
| Mean | 17 | 16.9 |
| SD | 4.45 | 3.87 |

Table 4 PBOX-6 has no significant effect on normal bone marrow progenitor cells. Mononucleur cells were isolated as described in materials and methods and treated with either ethanol (0.5% v/v) or PBOX-6 (10 μM for 72 hours. Cells were plated in triplicate onto semi-solid medium at 1×10$^5$ cells per sample and incubated at 37° C. After 14 days incubation, colonies were scored. A colony was scored as a cluster containing >40 cells, which originate from one stem cell.

What is claimed is:
1. A compound having the general formula (I):

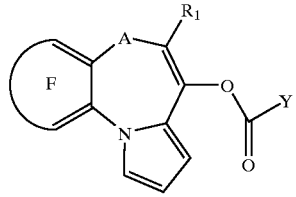

wherein:
(i) R$_1$ represents an unsubstituted C$_6$ or C$_{10}$ aryl group; or a C$_6$ aryl group substituted with Me or OMe;
(ii) A represents O, S or a sulfur atom oxidized to a sulfoxide;
(iii) the cyclic group labeled F represents an unsubstituted C$_6$ or C$_{10}$ aryl or a C$_5$ heteroaryl group having nitrogen as a heteroatom or a phenyl group substituted with ethoxycarbonyl function; and
(iv) Y represents the group

wherein R$_2$ and R$_3$ are independently hydrogen; or methyl or ethyl;
or Y represents the group CH$_3$, or (CH$_2$)$_2$CH$_3$ or an unsubstituted C$_5$ heteroaryl group having nitrogen as a heteroatom.

2. The compound of claim 1 wherein R$_1$ is an unsubstituted 1-naphthyl group.

3. The compound of claim 1 wherein F is an unsubstituted phenyl group or an unsubstituted naphthyl or 2,3-pyridine.

4. The compound of claim 1 wherein R$_1$ and F represent a 1-naphthyl group and a 2,3-naphto-fused group, respectively.

5. The compound of claim 1 wherein Y is selected from the group consisting of CH$_3$ or N(Me)$_2$, NHMe or a 4-pyridine group.

6. A compound of claim 1 selected from the group consisting of:
4-Acetoxy-5-phenylnaphto[2,3-b]pyrrolo[1,2-d][1,4]oxazepine,
7-Acetoxy-6-(1-naphthyl)pyrrolo[2,1-d][1,5]benzoxazepine,
4[(Dimethylcarbamoyl)oxy]-5-phenylnaphto[2,3-b]pyrrolo[1,2-d][1,4]oxazepine,
7-[(Dimethylcarbamoyl)oxy]-6-(1-naphthyl)pyrrolo[2,1-d][1,5]benzoxazepine,
7-[(Methylcarbamoyl)oxy]-6-(1-naphthyl)pyrrolo[2,1-d][1,5]-benzoxazepine,
7-[(Dimethylcarbamoyl)oxy]-6-(1-naphthyl)pyrrolo[2,1-d][1,5]benzothiazepine,
7-Acetoxy-6-(1-naphthyl)pyrrolo[2,1-d][1,5]benzothiazepine,
7-Acetoxy-6-(1-naphthyl)pyrrolo[1,2-d]pyrido[3,2-b][1,4]oxazepine,
4-Acetoxy-5-(1-naphthyl)naphtho[2,3-b]pyrrolo[1,2-d][1,4]oxazepine,
4-[(Dimethylcarbamoyl)oxy]-5-(1-naphthyl)naphtho[2,3-b]pyrrolo[1,2-d][1,4]oxazepine, 7-[(Ethylcarbamoyl)oxy]-6-phenylpyrrolo[2,1-d][1,5]benzoxazepine, 7-[(Methylcarbamoyl)oxy]-6-phenylpyrrolo[2,1-d][1,5] benzoxazepine,
7-Isonicotinoyloxy-6-(p-methoxyphenyl)pyrrolo[2,1-d][1,5]benzothiazepine, or
7-(Butyryloxy)-6-(p-methoxyphenyl)pyrrolo[2,1-d][1,5] benzothiazepine 5-oxide.

7. A pharmaceutical composition comprising the compound of any one of claims 1–6 and a pharmaceutically acceptable carrier.

8. A method for selective apoptosis in cancerous conditions selected from the group consisting of leukemia, lymphoma, cervical cancer and breast cancer, comprising:
   administering to a subject in need thereof, a pharmaceutically effective amount of a compound of formula I

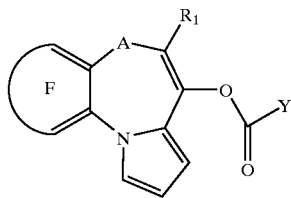

wherein:
(i) $R_1$ represents an unsubstituted $C_6$ or $C_{10}$ aryl group; or a $C_6$ aryl group substituted with Me or OMe;
(ii) A represents O, S; or a sulfur atom oxidized to sulfoxide;
(iii) the cyclic group labeled F represents an unsubstituted $C_6$ or $C_{10}$ aryl or a $C_5$ heteroaryl group having nitrogen as a heteroatom or a phenyl group substituted with ethoxycarbonyl function; and
(iv) Y represents the group

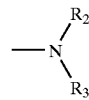

wherein $R_2$ and $R_3$ are independently hydrogen; or methyl or ethyl;

or Y represents the group $CH_3$; or $(CH_2)_2CH_3$ or an unsubstituted $C_5$ heteroaryl group having nitrogen as a heteroatom; and assessing the affects of the administration.

9. The method of claim 8 wherein the subject is a human or animal.

10. A method of claim 8 wherein the subject is administered a pharmaceutically effective amount of a compound selected from the group consisting of:
4-Acetoxy-5-phenylnaphto[2,3-b]pyrrolo[1,2-d][1,4] oxazepine,
7-Acetoxy-6-(1-naphthyl)pyrrolo[2,1-d][1,5] benzoxazepine,
4[(Dimethylcarbamoyl)oxy]-5-phenylnaphto[2,3-b]pyrrolo[1,2-d][1,4]oxazepine,
7-[(Dimethylcarbamoyl)oxy]-6-(1-naphthyl)pyrrolo[2,1-d][1,5]benzoxazepine,
7-[(Methylcarbamoyl)oxy]-6-(1-naphthyl)pyrrolo[2,1-d][1,5]-benzoxazepine,
7-[(Dimethylcarbamoyl)oxy]-6-(1-naphthyl)pyrrolo[2,1-d][1,5]benzothiazepine,
7-Acetoxy-6-(1-naphthyl)pyrrolo[2,1-d][1,5] benzothiazepine,
7-Acetoxy-6-(1-naphthyl)pyrrolo[1,2-d]pyrido[3,2-b][1,4] oxazepine,
4-Acetoxy-5-(1-naphthyl)naphtho[2,3-b]pyrrolo[1,2-d][1,4] oxazepine,
4-[(Dimethylcarbamoyl)oxy]-5-(1-naphthyl)naphtho[2,3-b]pyrrolo[1,2-d][1,4]oxazepine, 7-[(Ethylcarbamoyl)oxy]-6-phenylpyrrolo[2,1-d][1,5]benzoxazepine,
7-[(Methylcarbamoyl)oxy]-6-phenylpyrrolo[2,1-d][1,5] benzoxazepine,
7-Isonicotinoyloxy-6-(p-methoxyphenyl)pyrrolo[2,1-d][1,5]benzothiazepine,
7-(Butyryloxy)-6-(p-methoxyphenyl)pyrrolo[2,1-d][1,5] benzothiazepine 5-Oxide.

* * * * *